United States Patent
Mounce et al.

(10) Patent No.: US 8,137,314 B2
(45) Date of Patent: Mar. 20, 2012

(54) INFUSION MEDIUM DELIVERY DEVICE AND METHOD WITH COMPRESSIBLE OR CURVED RESERVOIR OR CONDUIT

(75) Inventors: R. Paul Mounce, Burbank, CA (US); Paul F. Bente, IV, Los Angeles, CA (US); Ian B. Hanson, Northridge, CA (US); William H. Stutz, Jr., Eagle Rock, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 481 days.

(21) Appl. No.: 11/588,847

(22) Filed: Oct. 27, 2006

(65) Prior Publication Data

US 2008/0051709 A1 Feb. 28, 2008

Related U.S. Application Data

(60) Provisional application No. 60/839,832, filed on Aug. 23, 2006.

(51) Int. Cl.
*A61M 1/00* (2006.01)
(52) U.S. Cl. .......................................... 604/151; 604/131
(58) Field of Classification Search .................. 604/131, 604/133, 151, 153, 890.1, 891.1
See application file for complete search history.

(56) References Cited

U.S. PATENT DOCUMENTS

| | | | |
|---|---|---|---|
| 3,963,151 A | 6/1976 | North, Jr. | |
| 4,044,764 A | 8/1977 | Szabo et al. | |
| 4,089,624 A | 5/1978 | Nichols et al. | |
| 4,487,603 A * | 12/1984 | Harris | 604/152 |
| 4,525,164 A | 6/1985 | Loeb et al. | |
| 4,619,652 A | 10/1986 | Eckenhoff et al. | |
| 4,685,902 A | 8/1987 | Edwards et al. | |
| 4,793,239 A | 12/1988 | Eickmann | |
| 4,838,857 A | 6/1989 | Strowe et al. | |
| 4,976,696 A | 12/1990 | Sanderson et al. | |
| 5,002,527 A | 3/1991 | Reller et al. | |
| 5,053,001 A | 10/1991 | Reller et al. | |
| 5,062,834 A | 11/1991 | Gross et al. | |
| 5,090,963 A | 2/1992 | Gross et al. | |

(Continued)

FOREIGN PATENT DOCUMENTS

BE 685 301 1/1967

(Continued)

OTHER PUBLICATIONS

Partial PCT Search Report dated Mar. 26, 2008 for PCT/US2007/076471.

(Continued)

*Primary Examiner* — Jackie Ho
*Assistant Examiner* — Emily Schmidt
(74) *Attorney, Agent, or Firm* — Foley & Lardner LLP

(57) ABSTRACT

A delivery device includes a durable housing portion and a separable disposable portion that selectively engage and disengage from each other. The disposable housing portion secures to the patient-user and may be disposed of after it has been in use for a prescribed period. Components that normally come into contact with a patient-user or with infusion media are supported by the disposable housing portion for disposal after the prescribed use, while the durable housing portion supports other components such as electronics for controlling delivery of infusion media from the reservoir and a drive device and drive linkage.

34 Claims, 21 Drawing Sheets

U.S. PATENT DOCUMENTS

| | | |
|---|---|---|
| 5,156,591 A | 10/1992 | Gross et al. |
| 5,176,502 A | 1/1993 | Sanderson et al. |
| 5,186,805 A | 2/1993 | Gross et al. |
| 5,190,522 A | 3/1993 | Wojcicki et al. |
| 5,203,506 A | 4/1993 | Gross et al. |
| 5,232,449 A | 8/1993 | Stern et al. |
| 5,242,406 A | 9/1993 | Gross et al. |
| 5,242,408 A | 9/1993 | Jhuboo et al. |
| 5,246,147 A | 9/1993 | Gross et al. |
| 5,254,096 A | 10/1993 | Rondelet et al. |
| 5,259,732 A | 11/1993 | Stern |
| 5,261,884 A | 11/1993 | Stern et al. |
| 5,266,013 A | 11/1993 | Aubert et al. |
| 5,295,966 A | 3/1994 | Stern et al. |
| 5,295,967 A | 3/1994 | Rondelet et al. |
| 5,356,632 A | 10/1994 | Gross et al. |
| 5,425,706 A | 6/1995 | Gross et al. |
| 5,431,634 A | 7/1995 | Brown |
| 5,527,288 A | 6/1996 | Gross et al. |
| 5,704,520 A | 1/1998 | Gross |
| 5,800,420 A | 9/1998 | Gross et al. |
| 5,807,375 A | 9/1998 | Gross et al. |
| 5,820,622 A | 10/1998 | Gross et al. |
| 5,840,069 A * | 11/1998 | Robinson .................. 604/131 |
| 5,848,991 A | 12/1998 | Gross et al. |
| 5,851,549 A | 12/1998 | Svec |
| 5,858,001 A | 1/1999 | Tsals et al. |
| 5,871,125 A | 2/1999 | Gross |
| 5,951,523 A | 9/1999 | Osterlind et al. |
| 5,957,889 A | 9/1999 | Poulsen et al. |
| 5,984,894 A | 11/1999 | Poulsen et al. |
| 5,997,501 A | 12/1999 | Gross et al. |
| 6,003,736 A | 12/1999 | Ljunggren |
| 6,033,377 A | 3/2000 | Rasmussen et al. |
| 6,099,504 A | 8/2000 | Gross et al. |
| 6,186,982 B1 | 2/2001 | Gross et al. |
| 6,203,296 B1 | 3/2001 | Ray et al. |
| 6,261,272 B1 | 7/2001 | Gross et al. |
| 6,275,717 B1 | 8/2001 | Gross et al. |
| 6,312,409 B1 | 11/2001 | Gross |
| 6,314,317 B1 | 11/2001 | Willis |
| 6,346,095 B1 | 2/2002 | Gross et al. |
| 6,364,865 B1 | 4/2002 | Lavi et al. |
| 6,406,455 B1 | 6/2002 | Willis et al. |
| 6,440,096 B1 | 8/2002 | Lastovich et al. |
| 6,474,219 B2 | 11/2002 | Klitmose et al. |
| 6,478,771 B1 | 11/2002 | Lavi et al. |
| 6,485,461 B1 | 11/2002 | Mason et al. |
| 6,490,483 B2 | 12/2002 | Willis |
| 6,508,788 B2 | 1/2003 | Preuthun |
| 6,537,251 B2 | 3/2003 | Klitmose |
| 6,585,707 B2 | 7/2003 | Cabiri et al. |
| 6,589,229 B1 | 7/2003 | Connelly et al. |
| 6,595,956 B1 | 7/2003 | Gross et al. |
| 6,607,513 B1 | 8/2003 | Down et al. |
| 6,613,019 B2 | 9/2003 | Munk |
| 6,616,627 B2 | 9/2003 | Willis et al. |
| 6,641,565 B1 | 11/2003 | Lavi et al. |
| 6,645,181 B1 | 11/2003 | Lavi et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,723,068 B2 | 4/2004 | Lavi et al. |
| 6,723,072 B2 | 4/2004 | Flaherty et al. |
| 6,740,059 B2 | 5/2004 | Flaherty |
| 6,749,587 B2 | 6/2004 | Flaherty |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,808,506 B2 | 10/2004 | Lastovich et al. |
| 6,830,558 B2 | 12/2004 | Flaherty et al. |
| 6,830,560 B1 | 12/2004 | Gross et al. |
| 6,899,699 B2 | 5/2005 | Enggaard |
| 6,936,006 B2 | 8/2005 | Sabra |
| 6,939,324 B2 | 9/2005 | Gonnelli et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 2002/0040208 A1 | 4/2002 | Flaherty et al. |
| 2002/0062105 A1 | 5/2002 | Tanner et al. |
| 2002/0072733 A1 | 6/2002 | Flaherty |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0229310 A1 | 12/2003 | Flaherty et al. |
| 2004/0010207 A1 | 1/2004 | Flaherty et al. |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116862 A1 | 6/2004 | Ray |
| 2004/0116866 A1 | 6/2004 | Gorman et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0022274 A1 | 1/2005 | Campbell et al. |
| 2005/0177108 A1 | 8/2005 | Paul et al. |
| 2005/0238512 A1 | 10/2005 | Luharuka et al. |
| 2006/0173419 A1* | 8/2006 | Malcolm .................. 604/246 |
| 2006/0264835 A1 | 11/2006 | Nielsen et al. |
| 2006/0271020 A1* | 11/2006 | Huang et al. ............. 604/890.1 |

FOREIGN PATENT DOCUMENTS

| | | |
|---|---|---|
| DE | 272700 | 3/1913 |
| DE | 35 17 927 C1 | 7/1986 |
| EP | 0 980 690 A2 | 2/2000 |
| EP | 0 988 868 A1 | 3/2000 |
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| WO | WO 81/01658 | 6/1981 |
| WO | WO 01/76684 A1 | 10/2001 |
| WO | WO 02/20073 A2 | 3/2002 |
| WO | WO 02/28454 A2 | 4/2002 |
| WO | WO 02/40083 A2 | 5/2002 |
| WO | WO 02/49509 A2 | 6/2002 |

| | | | |
|---|---|---|---|
| WO | WO 02/068015 A2 | 9/2002 |
| WO | WO 03/024504 A2 | 3/2003 |
| WO | WO 03/033051 A1 | 4/2003 |
| WO | WO 03/059372 A2 | 7/2003 |
| WO | WO 03/059372 A3 | 7/2003 |
| WO | WO 03/074121 A1 | 9/2003 |
| WO | WO 03/090509 A2 | 11/2003 |
| WO | WO 03/090819 A2 | 11/2003 |
| WO | WO 03/090838 A1 | 11/2003 |
| WO | WO 03/103758 A1 | 12/2003 |
| WO | WO 03/103763 A1 | 12/2003 |
| WO | WO 2004/006981 A2 | 1/2004 |
| WO | WO 2004/006982 A2 | 1/2004 |
| WO | WO 2004/030716 A2 | 4/2004 |
| WO | WO 2004/030717 A2 | 4/2004 |
| WO | WO 2004/032994 A2 | 4/2004 |
| WO | WO 2004/060436 A2 | 7/2004 |
| WO | WO 2004/093648 A2 | 11/2004 |
| WO | WO 2004/098390 A2 | 11/2004 |
| WO | WO 2004/098454 A2 | 11/2004 |
| WO | WO 2005/002649 A1 | 1/2005 |
| WO | WO 2005/037350 A2 | 4/2005 |
| WO | WO 2005/072795 A2 | 8/2005 |
| WO | WO 2006/015301 A2 | 2/2006 |
| WO | WO 2006/015922 A1 | 2/2006 |
| WO | WO 2006/018425 A2 | 2/2006 |
| WO | WO 2006/018425 A3 | 2/2006 |
| WO | WO 2006/018447 A2 | 2/2006 |
| WO | WO 2006/018447 A3 | 2/2006 |
| WO | WO 2006/024671 A1 | 3/2006 |
| WO | WO 2006/024672 A1 | 3/2006 |
| WO | WO 2006/042811 A2 | 4/2006 |
| WO | WO 2006/042811 A3 | 4/2006 |
| WO | WO 2006/072416 A2 | 7/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/084464 A1 | 8/2006 |
| WO | WO 2006/086980 A1 | 8/2006 |
| WO | WO 2006/089547 A1 | 8/2006 |
| WO | WO 2006/089548 A1 | 8/2006 |
| WO | WO 2006/089965 A1 | 8/2006 |
| WO | WO 2006/096746 A1 | 9/2006 |
| WO | WO 2006/097453 A1 | 9/2006 |
| WO | WO 2006/104806 A2 | 10/2006 |
| WO | WO 2006/108775 A2 | 10/2006 |
| WO | WO 2006/108809 A1 | 10/2006 |
| WO | WO 2006/116997 A1 | 11/2006 |
| WO | WO 2006/120253 A2 | 11/2006 |
| WO | WO 2006/125692 A1 | 11/2006 |
| WO | WO 2006/127905 A2 | 11/2006 |
| WO | WO 2007/000425 A2 | 1/2007 |
| WO | WO 2007/000426 A2 | 1/2007 |
| WO | WO 2007/000427 A1 | 1/2007 |
| WO | WO 2007/052277 A1 | 5/2007 |

OTHER PUBLICATIONS

PCT Search Report dated Jun. 5, 2008 for PCT/US2007/076471.
Office Action date May 27, 2009 from related U.S. Appl. No. 11/645,993.
US Office Action dated Mar. 23, 2010 from related U.S. Appl. No. 11/636,384.
US Office Action for U.S. Appl. No. 11/636,384 dated Jun. 15, 2009.
US Office Action for U.S. Appl. No. 11/636,384 dated Nov. 26, 2008.
US Office Action for U.S. Appl. No. 11/636,384 dated Oct. 19, 2009.
US Office Action for U.S. Appl. No. 11/645,993 dated Jul. 9, 2008.
US Office Action for U.S. Appl. No. 11/645,993 dated Jan. 8, 2009.
US Office Action for U.S. Appl. No. 11/645,993 dated Dec. 2, 2009.

* cited by examiner

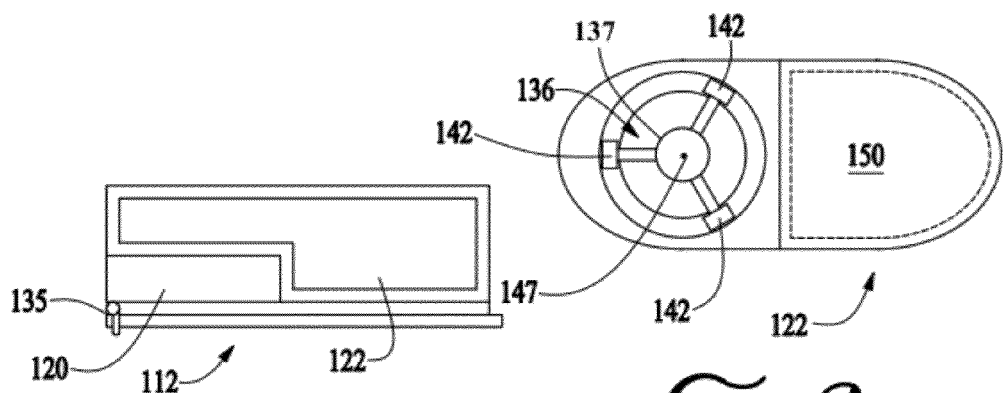
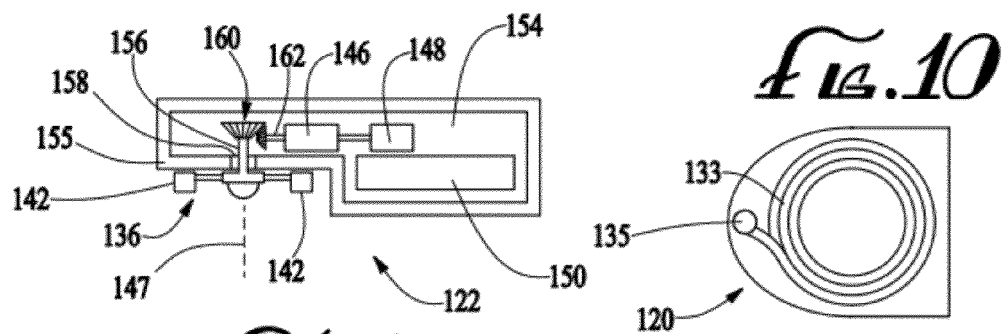
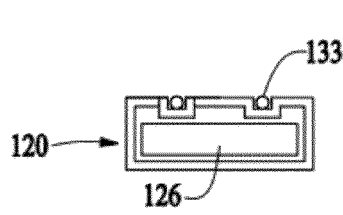
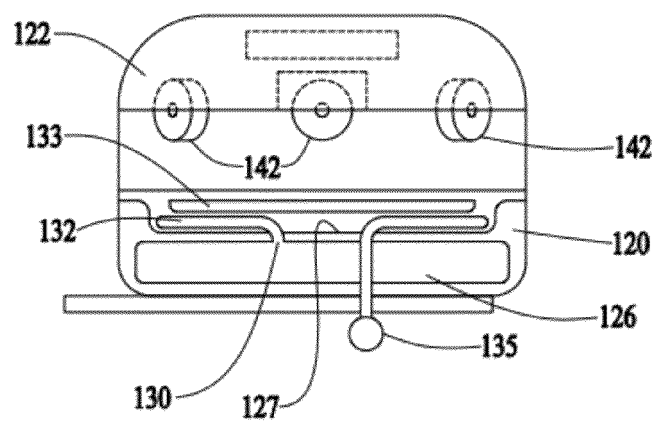

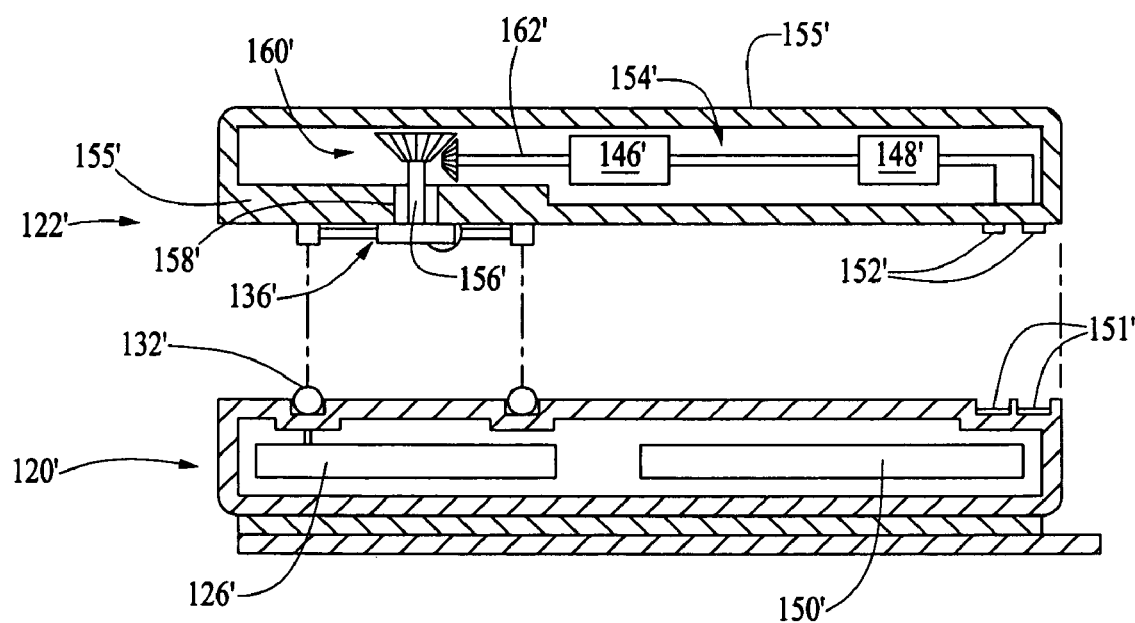

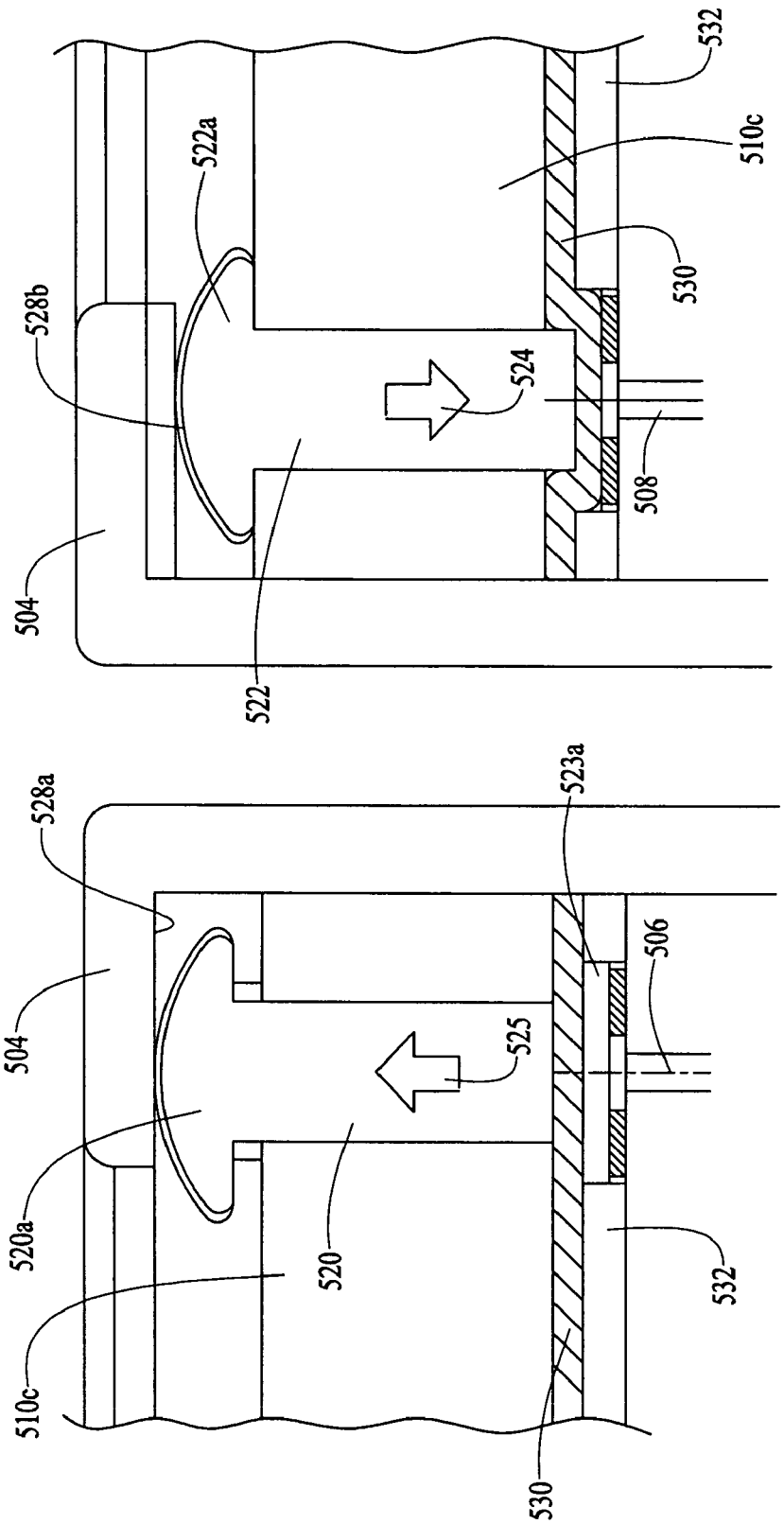

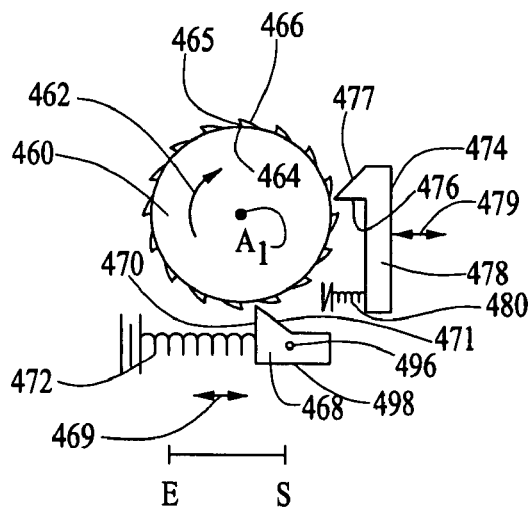
fig. 24A
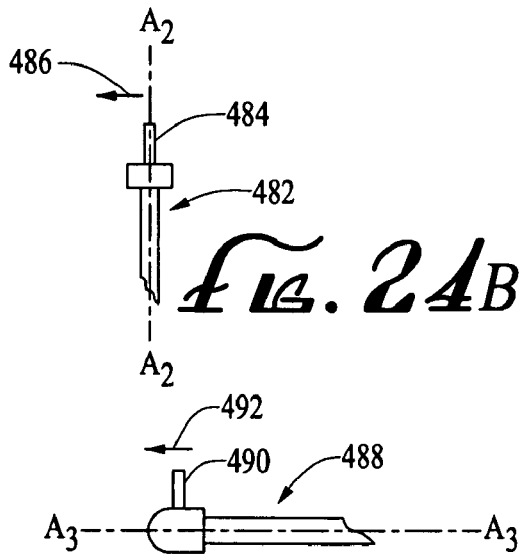
fig. 24B
fig. 24C
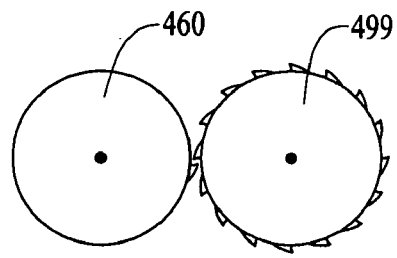
fig. 24D

INFUSION MEDIUM DELIVERY DEVICE AND METHOD WITH COMPRESSIBLE OR CURVED RESERVOIR OR CONDUIT

CROSS-REFERENCE TO RELATED PATENT APPLICATIONS

The present invention relates to U.S. Provisional Patent Application 60/839,832, filed Aug. 23, 2006, titled Infusion Medium Delivery Device And Method With Compressible Or Curved Reservoir Or Conduit," which is incorporated herein by reference in its entirety and from which a priority filing date is claimed. The present invention also relates to U.S. Patent Application 60/678,290, filed May 6, 2005 and U.S. patent application Ser. No. 11/211,095, filed Aug. 23, 2005, titled "Infusion Device And Method With Disposable Portion," each of which is incorporated herein by reference in its entirety. The present invention also relates to application No. 60/839,821, filed Aug. 23, 2006, titled "Systems And Methods Allowing For Reservoir Filling And Infusion Medium Delivery", application No. 60/839,822, filed Aug. 23, 2006 titled "Infusion Medium Delivery Device And Method For Driving Plunger In Reservoir"; application No. 60/839,840, filed Aug. 23, 2006, titled "Infusion Medium Delivery System, Device And Method With Needle Inserter And Needle Inserter Device Method"; and application No. 60/839,741, filed Aug. 23, 2006, titled "Infusion Pumps And Methods And Delivery Devices And Methods With Same", the contents of each of which is incorporated herein by reference, in its entirety. Embodiments of the present invention also relate to: (i) U.S. patent application Ser. No. 11/588,832, filed Oct. 27, 2006, entitled "Infusion Medium Delivery Device and Method with Drive Device for Driving Plunger in Reservoir"; (ii) U.S. patent application Ser. No. 11,588,875, filed Oct. 27, 2006, entitled "Systems And Methods Allowing For Reservoir Filling And Infusion Medium Delivery"; (iii) U.S. Provisional Patent Application Ser. No. 60/864,829, filed Oct. 27, 2006, entitled "Infusion Medium Delivery System, Device and Method with Needle Inserter and Needle Inserter Device and Method"; and (iv) U.S. patent application Ser. No. 11,589,323, filed Aug. 23, 2006, entitled "Infusion Pumps and Methods and Delivery Devices and Methods with Same", the contents of each of which are incorporated by reference herein, in their entirety.

FIELD OF THE INVENTION

Embodiments of the present invention relate to an infusion medium delivery device for delivering an infusion medium to a patient-user, wherein the delivery device includes a base portion and a durable portion connectable to the base portion, and wherein the base portion can be separated from the durable portion and disposed of after one or more specified number of uses. The base portion supports a compressible reservoir or conduit, while the durable portion supports a rotor or moveable track that is operatively coupled to a drive device for selective compression of the reservoir or conduit, to drive fluid out of the reservoir. In further embodiments, the reservoir may comprise a curved channel in which a plunger head is moveable in response to movement of a moveable track.

BACKGROUND OF THE INVENTION

Certain chronic diseases may be treated, according to modern medical techniques, by delivering a medication or other substance to a patient-user's body, either in a continuous manner or at particular times or time intervals within an overall time period. For example, diabetes is a chronic disease that is commonly treated by delivering defined amounts of insulin to the patient-user at appropriate times. Some common modes of providing an insulin therapy to a patient include delivery of insulin through manually operated syringes and insulin pens. Other modern systems employ programmable pumps to deliver controlled amounts of insulin to a patient.

Pump type delivery devices have been configured in external devices (that connect to a patient-user) or implantable devices (to be implanted inside of a patient-user's body). External pump type delivery devices include devices designed for use in a generally stationary location (for example, in a hospital or clinic), and further devices configured for ambulatory or portable use (to be carried by a patient-user). Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula.

In contexts in which the hollow tubing is connected to the patient-user through a hollow needle that pierces the patient-user's skin, a manual insertion of the needle into the patient-user can be somewhat traumatic to the patient-user. Accordingly, insertion mechanisms have been made to assist the insertion of a needle into the patient-user, whereby a needle is forced by a spring to quickly move from a retracted position into an extended position. Examples of insertion mechanisms that are built into a delivery device are described in U.S. patent application Ser. No. 11/211,095, filed Aug. 23, 2005, titled "Infusion Device And Method With Disposable Portion" (assigned to the assignee of the present invention), which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. As the needle is moved into the extended position, the needle is quickly forced through the patient-user's skin in a single, relatively abrupt motion that can be less traumatic to a patient-user as compared to a slower, manual insertion of a needle.

As compared to syringes and insulin pens, pump type delivery devices can be significantly more convenient to a patient-user, in that accurate doses of insulin may be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patient-users become more familiar with such devices, the popularity of external medical infusion pump treatment increases and is expected to increase substantially over the next decade.

SUMMARY OF THE DISCLOSURE

Embodiments of the present invention relate to an infusion medium delivery device for delivering an infusion medium to a patient-user, wherein the delivery device includes a first (or durable) housing portion and a second (or disposable) housing portion that selectively, engage and disengage from each other, for example, by manual force. One or both of the first and second housing portions secures to the patient-user. The disposable housing portion may be disposed of after it has been in use for a prescribed period. Components that normally come into contact with a patient-user and/or with infusion media may be supported by the disposable housing portion for disposal after the prescribed use, while the durable housing portion supports other components such as electronics for controlling the delivery of infusion media.

In some example embodiments, the disposable housing portion supports a compressible reservoir or conduit, while the durable housing portion supports a rotor or moveable track that is operatively coupled to a drive device for selective compression of the reservoir or conduit, to drive fluid out of the reservoir or through the conduit. In further embodiments, the reservoir may comprise a curved channel in which a plunger head is moveable in response to movement of a moveable track.

According to an example embodiment, a delivery device includes first and second housing portions as described above and a rotatable rotor that supports at least one pad or roller for movement in an annular path with the rotation of the rotor. In that embodiment, a conduit is supported by the first housing portion and has a flexible portion arranged within at least a portion of the annular path of the pad(s) or roller(s) to be engaged at locations along the annular path by the pad(s) or roller(s) when the second housing portion and the first housing portion are engaged. The flexible portion of the conduit is resiliently collapsible at the locations of engagement of the pad(s) or roller(s) to provide a pumping action as the rotor rotates the pad(s) or roller(s) along the annular path while the second housing portion and first housing portion are engaged. Also, the conduit is connectable in fluid flow communication with an injection site.

In the above-described example embodiment, the delivery device further includes a reservoir that has an interior volume for containing a fluid. The interior volume of the reservoir is provided in fluid flow communication with the conduit. In addition, a drive device is supported by the second housing portion and is operatively coupled to the rotor for selectively rotating the rotor.

In the same or a further example embodiment, the rotatable rotor is supported for rotation by the second housing portion. The rotor may be disposed within a recess in a wall of the second housing portion.

In the same or a further example embodiment, the second housing portion has a housing structure with an internal volume and the rotor is supported by the second housing portion, but is disposed outside of the internal volume of the second housing portion. In such an embodiment, the delivery device includes a rotor shaft that has a longitudinal axis. The rotor shaft is coupled to the rotor and extends into the internal volume of the second housing portion and is operatively coupled to the drive device. The rotor shaft may extend through an aperture in a wall of the second housing portion. A seal may be disposed around the aperture in the wall of the second housing portion.

In one example embodiment, the rotor comprises at least two wheels, including a drive wheel that is operatively coupled to a drive device to receive rotational drive force. In that example embodiment, a belt-like structure extends in an annular path around the two (or more) wheels, and at least one pad or roller is supported on the belt. Alternatively, the rotor may include a rotary wheel with the pad(s) or roller(s) supported by the rotary wheel. For example, the rotary wheel may be supported for rotation about a first axis of rotation with at least one rotatable roller supported for rotation on the rotary wheel about a second axis of rotation that is orthogonal to the first axis of rotation.

In any of the above-described embodiments, the flexible portion of the conduit may be supported on a flat support surface. Alternatively, the flexible portion of the conduit may be supported on a curved support surface. In any of the above-described embodiments, the reservoir may include a rigid container structure and the support surface may be a surface of the reservoir.

In a further example embodiment, the flexible portion of the conduit that is arranged within at least a portion of the annular path of the pad(s) or roller(s) includes a conduit portion arranged in at least a partial coil around a generally annular path. In such further example embodiment, the rotor is rotatable about a first axis of rotation and one or more rollers may be supported on the rotor, with each roller supported for rotation about a respective axis of rotation that is transverse to the first axis of rotation and/or along a path that aligns with the annular path of the conduit, when the first and second housing portions are engaged.

Further embodiments relate to methods of making a delivery device. In one example embodiment, a method includes providing a first housing portion and providing a second housing portion configured to selectively engage with and disengage from the first housing portion. The method according to that example embodiment further includes supporting a rotatable rotor for rotation, where the rotor has at least one pad or roller for movement in an annular path with the rotation of the rotor. The method according to that example embodiment also includes providing a conduit that has a flexible portion and coupling an interior volume of a reservoir in fluid flow communication with the conduit, where the interior volume of the reservoir is for containing a fluid.

The above example method embodiment further includes supporting the flexible portion of the conduit on the first housing portion and arranging the flexible portion of the conduit within at least a portion of the annular path of the pad(s) or roller(s) to be engaged at locations along the annular path by the pad(s) or roller(s) when the second housing portion and the first housing portion are engaged. The flexible portion of the conduit is resiliently collapsible at the locations of engagement of the pad(s) or roller(s) to provide a pumping action as the rotor rotates while the first and second housing portions are engaged. In addition, the conduit is connectable in fluid flow communication with an injection site.

In addition, the above example method embodiment further includes supporting a drive device on the second housing portion and operatively coupling the drive device to the rotor for selectively rotating the rotor to provide the pumping action while the first and second housing portions are engaged. In the above example embodiment, supporting a rotatable rotor may include supporting at least two wheels and extending a belt-like structure in an annular path around the at least two wheels, and wherein the at least one pad or roller is supported on the belt. Alternatively, supporting a rotatable rotor may include supporting a rotary wheel, where the pad(s) or roller(s) is(are) supported by the rotary wheel. In yet a further method embodiment, supporting a rotatable rotor includes supporting a rotary wheel for rotation about a first axis of rotation, and at least one rotatable roller is supported for rotation on the rotary wheel about a second axis of rotation that is orthogonal to the first axis of rotation.

A further example method embodiment includes arranging a portion of the conduit in at least a partial coil around a generally annular path. That further example method embodiment also includes supporting a rotor for rotation about a first axis and supporting one or more rollers on the rotor, each for rotation about a respective axis of rotation that is transverse to the first axis of rotation and/or along a path that aligns with the annular path of the conduit, when the first and second housing portions are engaged.

According to another example embodiment, a delivery device includes first and second housing portions as described above and a compressible reservoir located in the first housing portion. The reservoir has an interior volume for containing a fluid and an outlet connectable in fluid flow communication with an injection site. The interior volume of the reservoir is compressible to reduce the interior volume and increase fluid pressure within the interior volume to drive fluid from the interior volume to the injection site. A compression mechanism is operable on the reservoir and a drive device is supported by the second housing portion and operatively connectable to at least one of the reservoir and the compression mechanism when the first and second housing portions are engaged, to selectively cause relative movement between the reservoir and compression mechanism for selective compression of the reservoir.

A delivery device according to the above embodiment may further include a moveable track operatively coupled to the drive device to be selectively moved along a track path. In such an embodiment, the compression mechanism includes at least one roller or pad supported by the moveable track for engaging and compressing the reservoir as the track is moved along the track path.

In a delivery device according to one example of the above embodiment, the moveable track may be connected to the reservoir to move the reservoir as the track is moved along the track path. In such an example embodiment, the compression mechanism includes a pair of compression surfaces between which a portion of the reservoir is moved as the track is moved along the track path. The compression surfaces impart a compression force on the reservoir as the portion of the reservoir is moved between the compression surfaces. The pair of compression surfaces may include a pair of rollers.

In a delivery device according another example of the above embodiment, the compression mechanism comprises a plunger head supported for movement within the interior volume of the reservoir. In that example embodiment, the delivery device further includes a moveable track operatively coupled to a drive device to be selectively moved along a track path. The moveable track is operatively connectable to the plunger head to move the plunger head within the reservoir when the track is moved along the track path and when the first and second housing portions are engaged. In a further example of that example embodiment, the reservoir includes a curved channel having a radius of curvature and the track has a radius of curvature approximating the radius of curvature of the curved channel.

In any of the above-described embodiments, the delivery device may further include electrical control circuitry contained in the second housing portion. The electrical control circuitry controls the drive device for delivery of infusion media from the reservoir to the user when the second housing portion and the first housing portion are engaged.

Also in any of the above describe embodiments, one of the first and second housing portions may include a base portion that has a bottom surface and an adhesive material on the bottom surface for securing that housing portion to the skin of the user.

According to another example embodiment, the delivery device may include a moveable track coupled to one of the compression mechanism or the reservoir. In that example embodiment, the drive device is operatively coupled to the moveable track for moving the moveable track and one of the compression mechanism or the reservoir relative to the other of the compression mechanism and reservoir. In that example embodiment, a linkage structure may be provided for operatively coupling the drive device to the moveable track, to transfer drive force from the drive device to the moveable track.

Further embodiments of the present invention relate to methods of making delivery devices. According to one embodiment, a method includes providing a first housing portion and providing a second housing portion configured to selectively engage with and disengage from the first housing portion. That method embodiment further includes supporting a compressible reservoir on the first housing portion. The reservoir has an interior volume for containing a fluid and an outlet connectable in fluid flow communication with an injection site. The reservoir is compressible to reduce the interior volume and increase fluid pressure within the interior volume to drive fluid from the interior volume to the injection site.

That method embodiment further includes supporting a compression mechanism in a position to selectively compress the reservoir and supporting a drive device supported on the second housing portion in a position to operatively connect to at least one of the reservoir and the compression mechanism when the first and second housing portions are engaged, to selectively cause relative movement between the reservoir and compression mechanism for selective compression of the reservoir.

According to one example, the above method embodiment further includes operatively coupling a moveable track to the drive device to be selectively moved along a track path. In such example embodiment, supporting a compression mechanism comprises supporting at least one roller or pad on the moveable track for engaging and compressing the reservoir as the track is moved along the track path.

According to another example, the above method embodiment also further includes operatively coupling a moveable track to the drive device to be selectively moved along a track path. However this other example embodiment includes connecting the moveable track to the reservoir to move the reservoir as the track is moved along the track path. According to this other example embodiment, supporting a compression mechanism comprises supporting a pair of compression surfaces between which a portion of the reservoir is moved as the track is moved along the track path. The compression surfaces are supported in a position to impart a compression force on the reservoir as the portion of the reservoir is moved between the compression surfaces. In such an embodiment, supporting a pair of compression surfaces may include supporting a pair of rollers on the first housing portion.

In another example method embodiment, supporting a compression mechanism includes supporting a plunger head for movement within the interior volume of the reservoir. According to such other example embodiment, the method further includes operatively coupling a moveable track to the drive device to be selectively moved along a track path and operatively coupling the moveable track to the plunger head to move the plunger head within the reservoir when the track is moved along the track path and when the first and second housing portions are engaged. In such an embodiment, the reservoir may include a curved channel having a radius of curvature and the track may have a radius of curvature approximating the radius of curvature of the curved channel.

Any of the above-described method embodiments may further include containing electrical control circuitry in the second housing portion, where the electrical control circuitry controls the drive device for delivery of infusion media from the reservoir to the user when the second housing portion and the first housing portion are engaged. Also, any of the above-described embodiments may include providing one of the first and second housing portions with a base portion having a bottom surface and an adhesive material on the bottom surface for securing that housing portion to the skin of the user.

Another example method embodiment may include operatively coupling a moveable track to one of the compression mechanism or the reservoir. This other example embodiment also includes operatively coupling the drive device to the moveable track for moving the moveable track and one of the compression mechanism or the reservoir relative to the other of the compression mechanism and reservoir. This other example embodiment may also include operatively coupling linkage structure to the drive device and to the moveable track, to transfer drive force from the drive device to the moveable track.

According to another example embodiment, a delivery device includes first and second housing portions as described above and a reservoir located in the first housing portion. The reservoir has a selectively variable, first interior volume for containing a fluid and an outlet connectable in fluid flow communication with the first interior volume and an injection site. The delivery device according to this example embodiment also includes a volume varying mechanism defines a border of the first interior volume and is supported for motion in a curved path to selectively vary the first interior volume of the reservoir, to selectively reduce the first interior volume and increase fluid pressure within the interior volume to drive fluid from the interior volume to the injection site. The delivery device according to this example embodiment also includes a drive device supported by the second housing portion and operatively connectable to the volume varying mechanism when the first and second housing portions are engaged, to selectively drive the volume varying mechanism in the curved path of motion.

In the above-described example embodiment, the volume varying mechanism may include a rotary arm supported for rotation about a rotary axis within the reservoir. In such an embodiment, the first interior volume is located on one side of the rotary arm. In addition, a drive linkage may be operatively coupled to the drive device and the rotary arm, for conveying drive force from the drive device to the rotary arm when the first and second housing portions are engaged.

In one example embodiment, the drive linkage includes a shaft extending from one of the first and second housing portions and a receptacle located on the other of the first and second housing portions, where the shaft and receptacle each have a mating shape that engages and mates with the mating shape on the other of the shaft and receptacle when the first and second housing portions are engaged. In such an example embodiment, one of the shaft and the receptacle is operatively coupled to the drive device for rotation by the drive device and the other of the shaft and the receptacle is operatively coupled to the rotary arm to selectively rotate the rotary arm relative to the reservoir, to selectively vary the first interior volume of the reservoir.

In a further example embodiment, the drive linkage includes a shaft that extends from the second housing portion and is operatively coupled to the drive device for rotation by the drive device. In such further example embodiment, a receptacle is coupled to the rotary arm on the first housing portion. The shaft and the receptacle each have a mating shape that engages and mates with the mating shape on the other of the shaft and receptacle when the first and second housing portions are engaged.

In any of the above-described embodiments, the reservoir may have a disk-shaped interior and the first interior volume of the reservoir is a portion of the disk-shaped interior. In that embodiment, the disk-shaped interior may have a central axis and the rotary arm may be supported for rotation about the central axis of the disk-shaped interior. The rotary arm may have one end supported at the central axis of the disk shaped interior.

The reservoir may include a pair of walls within the disk-shaped interior, defining a wedge-shaped volume that is outside of the first interior volume of the reservoir. In such an embodiment, the reservoir outlet may be provided through one of the walls defining the wedge-shaped volume. Also, such an embodiment may further include an air vent through one of the walls defining the wedge-shaped volume and provided in air-flow communication with the disk-shaped interior of the reservoir.

In any of the above-described embodiments that have a disk-shaped reservoir interior, an air vent provided in air-flow communication with the disk-shaped interior of the reservoir. In such an embodiment, the air vent may be located in a wall of the reservoir on a side of the rotary arm opposite to the side of the first interior volume. Also in any of the above-described embodiments, the reservoir may have an overall interior volume in which the first interior volume is included; and the delivery device may further include an air vent provided in air-flow communication with the interior volume of the reservoir.

Further embodiments of the present invention relate to methods of making a delivery device for delivering a fluidic medium to or from a patient. In one embodiment, the method includes providing a first housing portion and providing a second housing portion configured to selectively engage with and disengage from the first housing portion. That method embodiment further includes providing a reservoir in the first housing portion. The reservoir has a first, selectively variable, interior volume for containing a fluid and an outlet connectable in fluid flow communication with the first interior volume and an injection site.

The above-described method embodiment further includes supporting a volume varying mechanism adjacent a border of the first interior volume for motion in a curved path to selectively vary the first interior volume of the reservoir, to selectively reduce the first interior volume and increase fluid pressure within the interior volume to drive fluid from the interior volume to the injection site. In addition, the above-described method embodiment includes supporting a drive device on the second housing portion in a position to operatively connect to the volume varying mechanism when the first and second housing portions are engaged, to selectively drive the volume varying mechanism in the curved path of motion.

In the above-described method embodiment, supporting a volume varying mechanism may include supporting a rotary arm for rotation about a rotary axis within the reservoir, wherein the first interior volume is located on one side of the rotary arm. Such an embodiment may further include operatively coupling a drive linkage to the drive device and the rotary arm for conveying drive force from the drive device to the rotary arm when the first and second housing portions are engaged.

In one example, operatively coupling a drive linkage includes extending a shaft from one of the first and second housing portions and providing a receptacle on the other of the first and second housing portions. In such an embodiment, the shaft and receptacle each have a mating shape that engages and mates with the mating shape on the other of the shaft and receptacle when the first and second housing portions are engaged. Such an embodiment further includes operatively coupling one of the shaft and the receptacle to the drive device for rotation by the drive device and operatively coupling the other of the shaft and the receptacle to the rotary arm to selectively rotate the rotary arm relative to the reservoir, to selectively vary the first interior volume of the reservoir.

In another example, operatively coupling a drive linkage includes operatively coupling a shaft to the drive device for rotation by the drive device and extending the shaft from the second housing portion. This embodiment further includes coupling a receptacle to the rotary arm on the first housing portion. The shaft and receptacle each have a mating shape that engages and mates with the mating shape on the other of the shaft and receptacle when the first and second housing portions are engaged.

In any of the above-described method embodiments, the reservoir may have a disk-shaped interior and the first interior volume of the reservoir may be a portion of the disk-shaped interior. In such embodiments, the disk-shaped interior may have a central axis and the method may include supporting a rotary arm for rotation about the central axis of the disk-shaped interior. Such an embodiment may include supporting one end of the rotary arm at the central axis of the disk shaped interior.

Any of the above-described embodiments may include providing an air vent in air-flow communication with the interior of the reservoir. Such an embodiment may include providing an air vent in a wall of the reservoir on a side of the rotary arm opposite to the side of the first interior volume. These and other embodiments of the present invention are described below, with reference to the accompanying drawings.

BRIEF DESCRIPTION OF THE DRAWINGS

FIG. 7 is a side view of a delivery device according to another embodiment of the invention.

FIG. 8 shows a top view of the durable housing portion of the delivery device of FIG. 7.

FIG. 9 shows a side cross-section view of the durable housing portion of the delivery device of FIG. 7.

FIG. 10 shows a bottom view of the disposable housing portion of the delivery device of FIG. 7.

FIG. 11 shows a side cross-section view of the disposable housing portion of the delivery device of FIG. 7.

FIG. 12 shows another side view of the delivery device of FIG. 7, with the disposable and durable housing portions separated.

FIG. 13 is a side cross section view of another embodiment of a delivery device, with the disposable and durable housing portions separated.

FIG. 21 is a partial cross-sectional view of a cam follower adjacent an inlet of the embodiment of FIG. 20.

FIG. 22 is a partial cross-sectional view of a cam follower adjacent an outlet of the embodiment of FIG. 20.

FIGS. 24a-24d are schematic views of various escapement wheel arrangements and components thereof that may be used with drive devices in various embodiments described herein.

DETAILED DESCRIPTION

Figure 1:
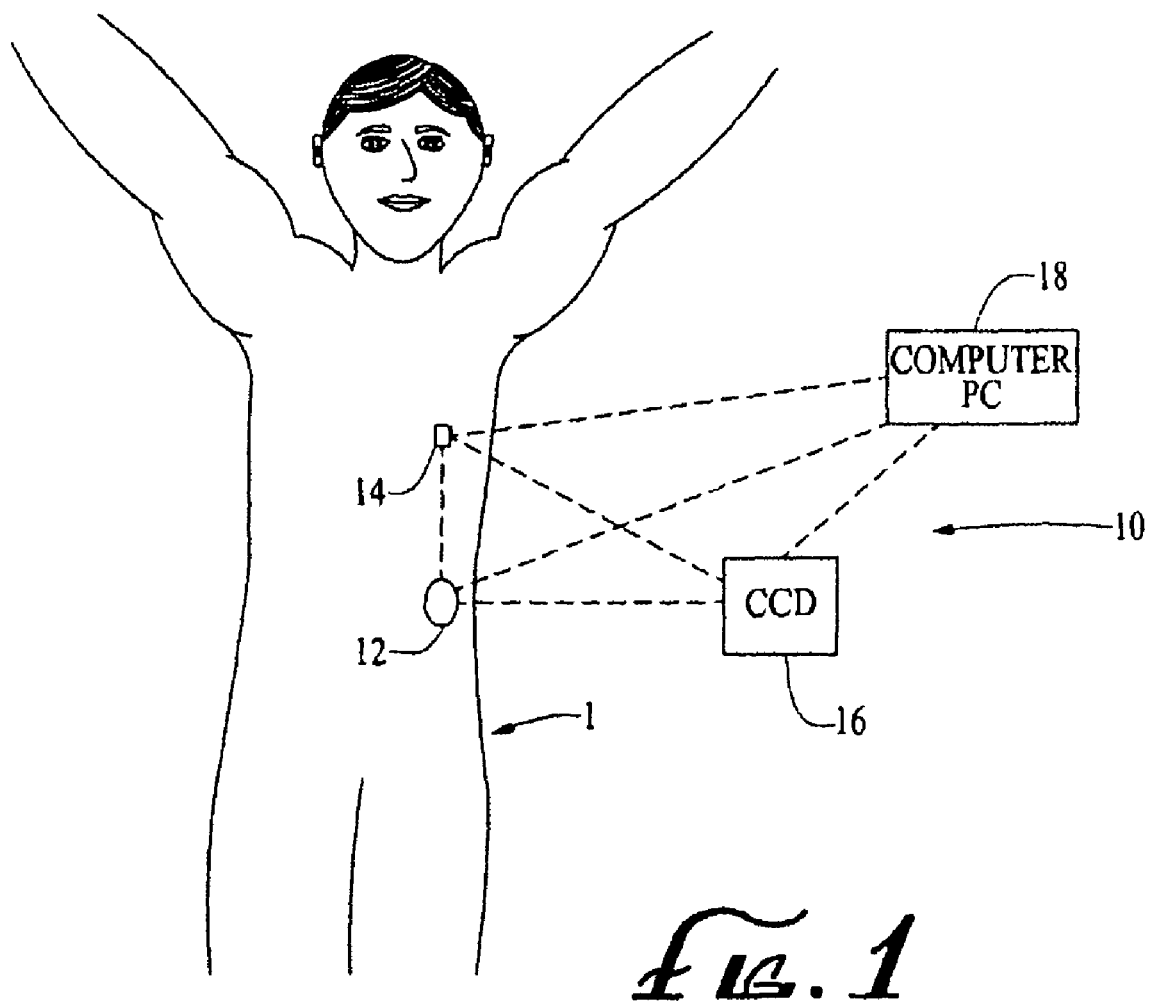
FIG. 1 is a generalized diagram of a delivery system in relation to a human patient-user.

The present invention relates, generally, to delivery devices, systems and methods for delivering an infusion medium, such as a drug, to a recipient, such as a medical patient-user. In particular embodiments, a delivery device includes first and second housing portions (referred to herein as a durable housing portion and a disposable housing portion, respectively) that are configured to engage and attach to each other for operation. The disposable housing portion may contain or otherwise support an infusion medium reservoir and other components that come into contact with the infusion medium and/or the patient-user during operation. The disposable housing portion may be disengaged and separated from the durable housing portion, such that the disposable housing portion may be readily disposed of after it has been in use for a period of time, or after one or a prescribed number of uses. After disengagement and separation from a disposable housing portion, the durable housing portion may be engaged and operatively connected to another disposable housing portion (such as a new, refurbished, refilled or re-manufactured disposable housing portion) for further operation. The durable housing portion may contain or otherwise support components that do not come into contact with the infusion medium or the patient-user during normal operation of the delivery device, including, but not limited to, a drive device, drive linkage, electronic circuits and, in some embodiments, a power source.

Delivery device embodiments described herein include a compressible reservoir or conduit that is acted upon by a compression structure. A rotor or moveable track provides relative motion between the compression structure and the reservoir or conduit, to selectively compress the reservoir or conduit and selectively drive fluid out of the reservoir to an injection site. Embodiments described herein employ various manners of supporting a drive device with the durable housing portion for driving the rotor or moveable track, while supporting a flexible reservoir or conduit with a the disposable housing portion, and to allow operative connection of the drive device and/or rotor or track to the flexible reservoir or conduit when the durable housing portion and disposable housing portion are engaged, yet also allow the durable housing portion and disposable housing portion to be disengaged and separated from each other, for replacement or servicing of the disposable housing portion.

For example, various embodiments employ a peristaltic pump arrangement, in which a rotor imparts a compression force on a flexible conduit, to draw fluid from the reservoir, through the conduit, when the disposable housing portion and durable housing portion are engaged. Further embodiments employ a flexible reservoir structure that is compressed by a compression structure, upon relative movement between the compression structure and the flexible reservoir. In further embodiments, the reservoir may comprise a curved channel in which a plunger head is moveable in response to movement of a moveable track. Various structures are described herein that allow the reservoir and certain other components to be supported by a disposable housing portion, while a drive device and other components may be supported in the durable housing portion for operable connection with the reservoir when the disposable housing portion and durable housing portion are engaged. Such embodiments may be configured to provide a reliable, user-friendly mechanism to secure the delivery device to a patient-user for delivery of fluidic an infusion medium to the patient-user and also provide a cost effective manner of replacing or servicing depleted or used reservoirs.

While embodiments of the present invention are described herein with reference to an insulin delivery example for treating diabetes, other embodiments of the invention may be employed for delivering other infusion media to a patient-user for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like. Also, while embodiments of the present invention are described herein for delivering or infusing an infusion medium to a patient-user, other embodiments may be configured to draw a medium from a patient-user.

Furthermore, while embodiments of the present invention refer to the housing portions of disclosed delivery devices as disposable or durable, and may be configured to allow the disposable housing portion to be disposed of and replaced in an economically efficient manner, it will be understood that, in further embodiments, the disposable housing portion embodiments described herein may be re-used and need not be disposed of. Similarly, the durable housing portion embodiments described herein may be disposed of after one or more uses, if desired. However, embodiments are configured to allow certain components (for example, those that contact the infusion medium or the patient-user during operation) to be housed in a first housing portion that may be readily disposable, while other components (for example, those that do not contact the infusion medium or the patient-user during operation and that have a replacement cost that is of a relatively significant level) may be housed in a second housing portion that may be re-used with one or more new, refilled, refurbished or remanufactured disposable first housing portions.

A generalized representation of an infusion medium delivery system 10 is shown in FIG. 1, wherein the system includes a delivery device 12 configured according to an embodiment of the invention described herein. The system 10 may also include other components coupled for communication with the delivery device 12, including, but not limited to, a sensor or monitor 14, a command control device (CCD) 16 and a computer 18. Each of the CCD 16, the sensor or monitor 14, the computer 18 and the delivery device 12 may include receiver or transceiver electronics that allow communication with other components of the system. The delivery device 12 may include electronics and software for analyzing sensor data and for delivering an infusion medium according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the system 10 may comprise delivery device 12 that operates without any one or more of the other components of the system 10 shown in FIG. 1. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

In the generalized system diagram of FIG. 1, the delivery device 12 and sensor or monitor 14 are secured to a patient-user 1. The locations at which those components are secured to the patient-user 1 in FIG. 1 are provided only as a representative, non-limiting example. The delivery device 12 and sensor or monitor 14 may be secured at other locations on the patient-user 1, and such locations may depend upon the type of treatment to be administered by the system 10. Such other locations may include, but are not limited to, other locations on the patient-user's body, locations on the patient-user's clothing, belt, suspenders, straps, purse, tote or other structure that may be carried by the patient-user.

As described in further detail below, the delivery device 12 contains a reservoir of an infusion medium and delivers the infusion medium, such as, but not limited to an insulin formulation, into the patient-user's body in a controlled manner. Control instructions and/or data may be communicated between the delivery device 12, the sensor or monitor 14, the CCD 16 and the computer 18. The delivery device 12 may be configured to secure to the skin of a patient-user 1, in the manner of a patch, at a desired location on the patient-user. In such embodiments, it is desirable that the delivery device 12 have relatively small dimensions for comfort and ability to conceal the device, for example, under a garment.

Examples of patch-like delivery devices are described in U.S. patent application Ser. No. 11/211,095, filed Aug. 23, 2005, which is incorporated herein, in its entirety. Delivery devices described in U.S. patent application Ser. No. 11/211, 095 employ a reservoir structure having a moveable plunger for selectively driving fluid from the reservoir. An example of a patch-like delivery device 12 that employs a peristaltic pumping arrangement, instead of a reservoir-plunger arrangement is shown in FIGS. 2-5 herein. The delivery device 12 in FIG. 2 includes a base housing portion 20 that, in some embodiments, may be disposable after one or a number of specified uses, and a further housing portion 22. For convenience, but without limitation, the base portion 20 is referred to herein as a disposable housing portion or disposable portion, while the further housing portion 22 is referred to herein as a durable housing portion or durable portion. However, as noted above, in operation, either or both housing portions 20 or 22 may be disposed of or re-used, depending upon the context of use.

The disposable housing portion 20 may support structural elements that ordinarily contact the patient-user's skin or the infusion medium, during operation of the delivery device 12. On the other hand, the durable housing portion 22 may support elements (including electronics, motor components, linkage components, and the like) that do not ordinarily contact the patient-user or the infusion medium during operation of the delivery device 12. Thus, elements in the durable housing portion 22 of the delivery device 12 are typically not contaminated from contact with the patient-user or the infusion medium during normal operation of the delivery device 12.

In the illustrated embodiment, the disposable housing portion 20 of the delivery device 12 comprises a base 21 that includes or otherwise supports a reservoir retaining portion 24 that houses a reservoir. The durable housing portion 22 may comprise a housing that secures onto the base 21 adjacent the reservoir retaining portion 24. The durable housing portion 22 may house a suitable drive device, such as an electrically operated motor (not shown in FIG. 2), and drive linkage components (not shown in FIG. 2) for driving fluid out of the reservoir. The durable housing portion 22 also may house suitable control electronics (not shown in FIG. 2) for controlling the operation of the drive device to drive fluid from the reservoir in a controlled manner. Further embodiments may include other electronics within the durable housing portion 22, such as, but not limited to communication electronics (not shown in FIG. 2) for communicating with the sensor or monitor 14, the CCD 16, the computer 18 and/or other components of the system 10 shown in FIG. 1.

The base 21 of the disposable housing portion 20 has a bottom surface (facing downward and into the page in FIGS. 2 and 3) that is configured to secure to a patient-user's skin at a desired location on the patient-user. A suitable adhesive may be employed at the interface between the bottom surface of the base 21 and the patient-user's skin, to adhere the base 21 to the patient-user's skin. The adhesive may be provided on the bottom surface of the base 21, with a peelable cover layer 23 covering the adhesive material. In this manner, a patient-user may peel off the cover layer 23 to expose the adhesive material and then place the adhesive side of the base 21 against the patient-user's skin.

The disposable portion 20 may include a button or other operator 25 for operating a needle inserter device located within the reservoir retaining portion 24. Alternatively, or in addition, reference number 25 may represent an opening, through which an external needle inserter device may operate. Alternatively, or in addition to an operator or opening 25, the needle inserter device may be activated, through a wireless link, from an external controller, such as the CCD 16, sensor or monitor 14 or computer 18. For such embodiments, the CCD 16, sensor or monitor 14 or computer 18 includes a wireless signal transmitter, while the delivery device includes a receiver for receiving a wireless actuation signal and an electronic actuator that is controlled to actuate the needle inserter device, upon receipt of an actuation signal from the CCD 16, sensor or monitor 14 or computer 18. Examples of suitable needle inserter devices are described in U.S. patent application Ser. No. 11/211,095, filed Aug. 23, 2005, and U.S. Patent Application No. 60/839,840, filed Aug. 23, 2006, titled "Infusion Medium Delivery System, Device And Method With Needle Inserter And Needle Inserter Device Method", each of which is incorporated herein by reference in its entirety. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653. filed Dec. 9, 2002, and entitled "Insertion Device For Insertion Set and Method of Using the Same," both of which are incorporated herein by reference in their entirety. Alternatively, the reservoir retaining portion may include a suitable opening or port for connecting one end of a hollow tube to the reservoir, while the other end of the hollow tube is connected to a hollow needle for piercing the patient-user's skin and conveying the infusion medium from the reservoir into the patient-user, for example, as described with reference to FIG. 2 of U.S. patent application Ser. No. 11/211, 095, filed Aug. 23, 2005.

The durable housing portion 22 of the delivery device 12 includes a housing shell configured to mate with and secure to the disposable housing portion 20. The durable housing portion 22 and disposable housing portion 20 may be provided with correspondingly shaped grooves, notches, tabs or other suitable features that allow the two parts to easily snap together, by manually pressing the two portions together in a manner well known in the mechanical arts. In a similar manner, the durable housing portion 22 and disposable housing portion 20 may be separated from each other by manually applying sufficient force to unsnap the two parts from each other. In further embodiments, a suitable seal, such as an annular seal, may be placed along the peripheral edge of the disposable housing portion 20 and/or the durable housing portion 22, so as to provide a liquid, hermetic, or air-tight seal between the disposable housing portion 20 and the durable housing portion 22.

The durable housing portion 22 and disposable housing portion 20 may be made of suitably rigid materials that maintain their shape, yet provide sufficient flexibility and resilience to effectively snap together and apart, as described above. The base 21 material may be selected for suitable compatibility with the patient-user's skin. For example, the disposable housing portion 20 and the durable housing portion 22 of the delivery device 12 may be made of any suitable plastic, metal, composite material or the like. The disposable housing portion 20 may be made of the same type of material or a different material relative to the durable housing portion 22. The disposable and durable housing portions may be manufactured by injection molding or other molding processes, machining processes or combinations thereof.

The base 21 may be made of a relatively flexible material, such as a flexible silicone, plastic, rubber, synthetic rubber or the like. By forming the base 21 of a material capable of flexing with the patient-user's skin, a greater level of patient-user comfort may be achieved when the base is secured to the patient-user's skin. Also, a flexible base 21 can result in an increase in the site options on the patient-user's body at which the base 21 may be secured.

The disposable housing portion 20 and/or the durable housing portion 22 may include an internal sensor (not shown in FIGS. 2 and 3) for connection to a patient-user, for example, through a needle (not shown in FIGS. 2 and 3) for piercing a patient-user's skin when the disposable housing portion 20 is secured to a patient-user's skin. In such embodiments, a suitable aperture (not shown in FIGS. 2 and 3) may be formed in the base 21, to allow the passage of the sensor needle, when the sensor needle to pierce a patient-user's skin. Alternatively, the durable housing portion 20 of the delivery device 12 may be connected to an external sensor 14, through a sensor lead, as described with respect to FIG. 2 of U.S. patent application Ser. No. 11/211,095, filed Aug. 23, 2005. The sensor may comprise any suitable biological sensing device, depending upon the nature of the treatment to be administered by the delivery device 12. For example, in the context of delivering insulin to a diabetes patient-user, the sensor 14 may comprise a blood glucose sensor. Alternatively, or in addition, one or more environmental sensing devices may be included in or on the delivery device 12, for sensing one or more environmental conditions. In further alternatives, the sensor may be included with as a part or along side the infusion cannula and/or needle, such as for example as shown in U.S. patent Ser. No. 11/149,119 filed Jun. 8, 2005, and entitled "Dual Insertion Set," which is incorporated herein by reference in its entirety.

As described above, by separating disposable elements of the delivery device 12 from durable elements, the disposable elements may be arranged on the disposable portion 20, while durable elements may be arranged within a separable durable portion 22. In this regard, after one (or a prescribed number) of uses of the delivery device 12, the disposable portion 20 may be separated from the durable portion 22, so that the disposable portion 20 may be disposed of in a proper manner. The durable portion 22 may, then, be mated with a new (user-filled, pre-filled, un-used, refilled, refurbished or re-manufactured) disposable portion 20 for further delivery operation with a patient-user.

A reservoir 26 is located in the reservoir retaining portion 24. The reservoir 26 may comprise a container having an internal volume for containing a fluidic infusion medium, such as, but not limited to an insulin formulation. The reservoir 26 may be made of any material suitably compatible with the infusion medium, including, but not limited to suitable metal, plastic, ceramic, glass, composite material or the like. For example, the canister may be formed of a plastic material referred to as TOPAS (cyclic olefin copolymer)(Topas is a trademark of Ticona, a subsidiary of Celanese Corporation), such as described in U.S. patent application Ser. No. 11/100, 188, filed Apr. 5, 2005 (Publication No. 2005/0197626), the contents of which is incorporated herein in its entirety. Examples of needle/septum connectors used in reservoirs can be found in U.S. patent application Ser. No. 10/328,393 filed Dec. 22, 2003, and entitled "Reservoir Connector," which is incorporated herein by reference in its entirety. In other alternatives, non-septum connectors for use with reservoirs such as Luer locks, or the like may be used.

The reservoir 26 may be supported by the reservoir retaining portion 24 of the disposable portion 20 in any suitable manner. For example, the reservoir 26 may be supported on a surface of the base 21 and held in place by one or more projections, walls or other stop surfaces 28. The projections, walls or other stop surfaces 28 may be formed or molded on or otherwise connected in a fixed manner to the base 21 or other structure of the disposable housing portion 20, in locations adjacent and abutting one or more sides of the reservoir 26. As described below, in some embodiments, the reservoir 26 may be configured to be removable and replaceable with respect to the disposable housing portion 20. In other embodiments, the reservoir 26 may be secured to the disposable housing portion 20 in a manner intended to inhibit removal of the reservoir 26 from the disposable housing portion 20. For example, an adhesive material may be employed to adhere a surface of the reservoir 26 to the base 21 or other structure of the disposable housing portion 20.

In yet other embodiments, the reservoir 26 may be formed unitarily with the reservoir retaining portion 24, for example, as a hollow chamber provided within an otherwise solid portion of the reservoir retaining portion 24. In such embodiments, the hollow interior of the reservoir retaining portion 24 may be coated or otherwise lined with a suitable metal, plastic, plastic, TOPAS (cyclic olefin copolymer)(Topas is a trademark of Ticona, a subsidiary of Celanese Corporation), ceramic, glass, composite material or the like. Alternatively, or in addition, the retaining portion 24, itself, may be made of a suitable metal, plastic, plastic, TOPAS (cyclic olefin copolymer)(Topas is a trademark of Ticona, a subsidiary of Celanese Corporation), ceramic, glass, composite material or the like.

Figure 4:
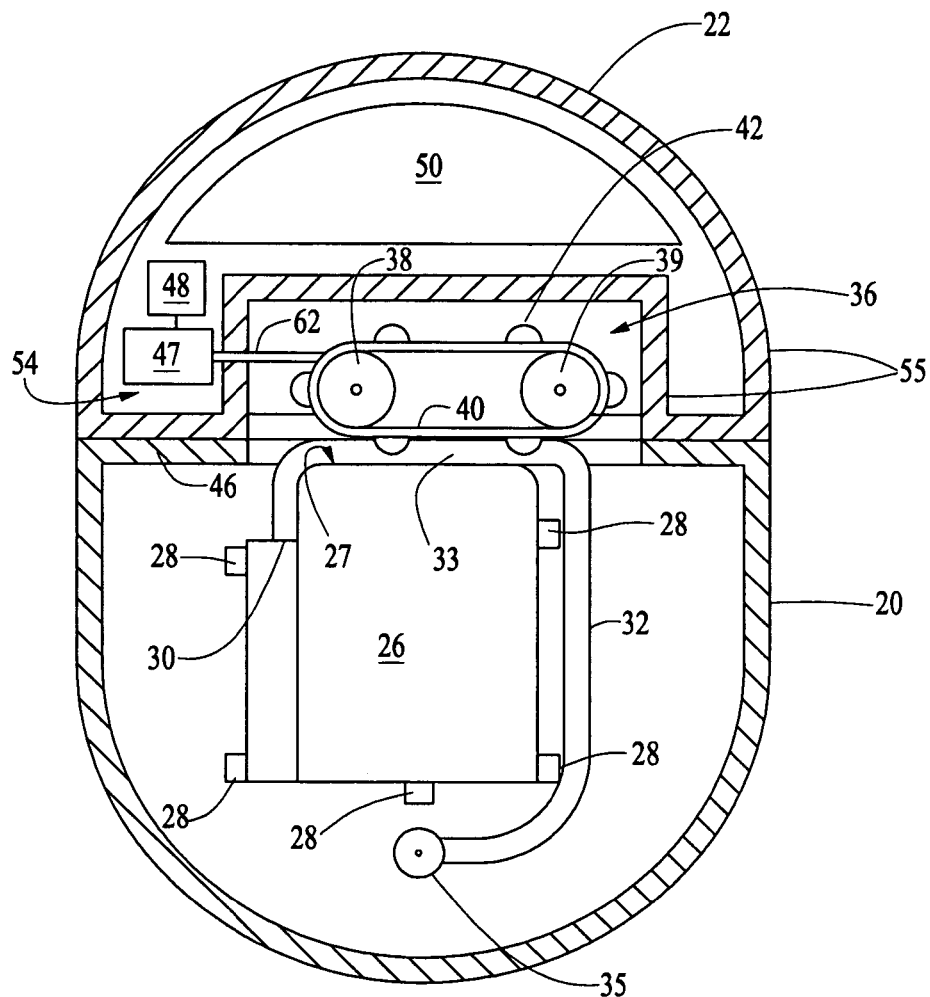
FIG. 4 is a schematic, cross-sectional view of a delivery device according to an embodiment of the invention.

In the embodiment shown in FIG. 4, the reservoir 26 has a generally rectangular-cube shape. In other embodiments, the reservoir 26 may have other shapes, including, but not limited to a disk or partial-disk shape, tube shape, curved tube shape or other shape that maximizes the internal volume of the reservoir, yet allows the dimensions of the reservoir retaining portion 24 to be minimized. As described below, in some embodiments, the reservoir 26 has a support surface 27 that may be formed as a flat surface (FIG. 4) or a curved surface (FIG. 6) for supporting a flexible tube against the action of a peristaltic pump rotor.

The reservoir 26 has an outlet port 30, through which the infusion medium contained within the interior of the reservoir 26 may be communicated out of the reservoir. The outlet port 30 is open to the interior of the reservoir 26 and may include suitable tube-connection structure. A tube-shaped conduit 32 having an internal fluid flow path is connected, at a first end, in fluid-flow communication with the outlet port 30. The conduit 32 may be made of any suitable material, including, but not limited to silicone or other plastic, metal, ceramic or composite material. At least a portion 33 of the length of the conduit 32 is made of a resilient, flexible material, such as, but not limited to a silicone or other plastic material suitable for repeated contact with pads or rollers of a peristaltic rotor, as described below, to repeatedly compress and return the fluid flow path within the length portion 33 of the conduit 32. In some embodiments, the entire length of the conduit 32 is made of the resilient, flexible material.

A second end of the conduit 32 is connected in fluid flow communication with an injection site 35 located on the disposable housing portion 20. The injection site 35 may comprise an insertion mechanism to assist the insertion of a needle or cannula into the patient-user and connection of the needle or cannula in flow communication with the conduit 32. Examples of such insertion mechanisms that are built into a delivery device are described in U.S. patent application Ser. No. 11/211,095, filed Aug. 23, 2005, titled "Infusion Device And Method With Disposable Portion" (assigned to the assignee of the present invention), which is incorporated herein by reference in its entirety. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Figure 6:
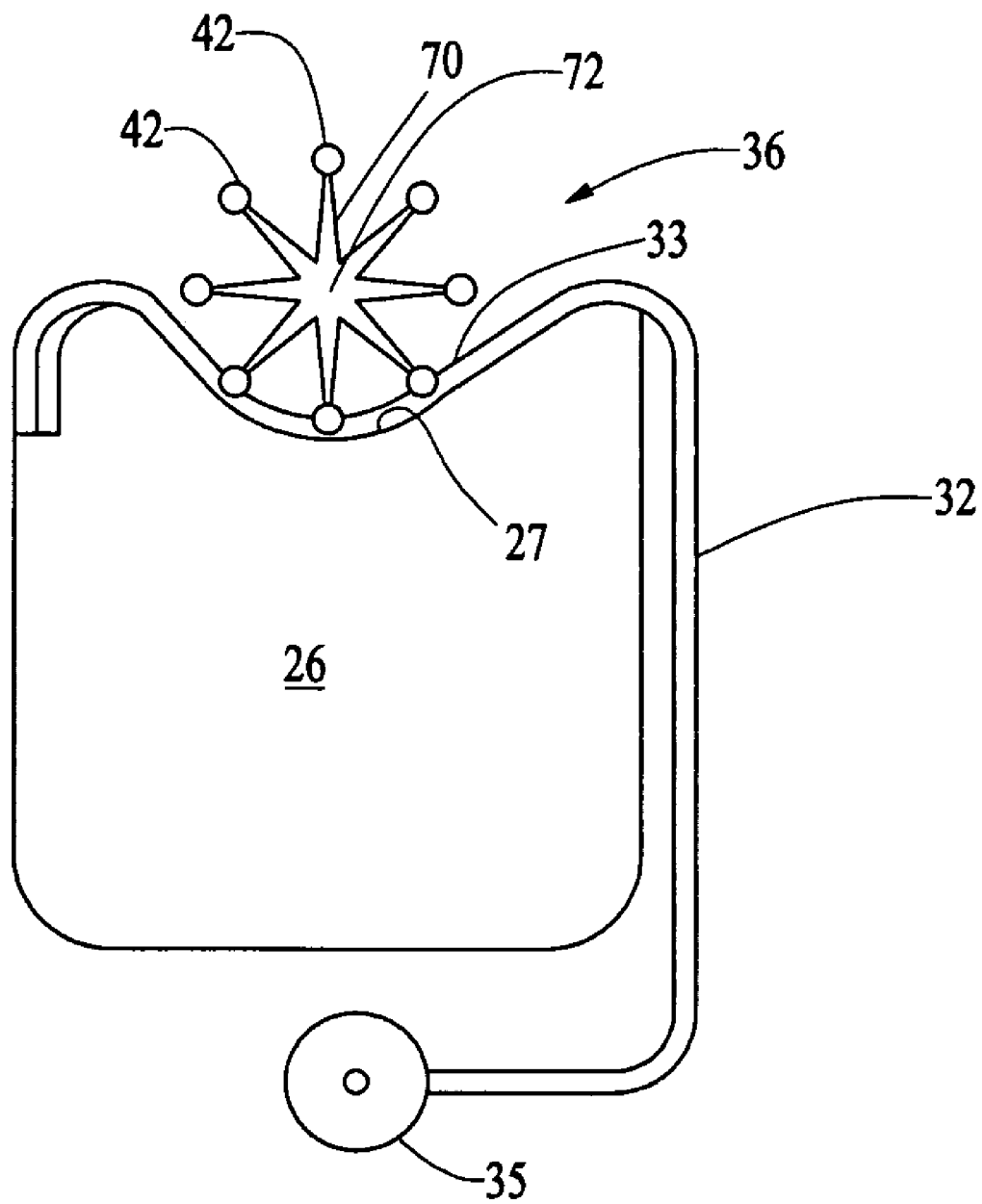
FIG. 6 is a schematic view of another reservoir, conduit and rotor arrangement that may be employed in a delivery device of FIG. 4, in place of the reservoir, conduit and rotor arrangement shown in FIG. 4.

In the embodiment shown in FIG. 4, the length portion 33 of the conduit 32 is supported on a surface 27 of the reservoir 26, at a location arranged to be contacted and compressed by one or more pads or rollers of a peristaltic rotor, when the durable housing portion 22 is engaged with the disposable housing portion 20. The conduit support surface 27 in FIG. 4 is a generally flat, outer surface of the reservoir 26. In other embodiments, such as shown in FIG. 6, the conduit support surface may comprise a curved surface, for increased length. While embodiments shown in FIGS. 4 and 6 show the conduit support surface 27 as an outer surface of the reservoir 26, in other embodiments, the conduit support surface may comprise a flat or curved surface of a wall or other structural portion of the disposable housing portion 20.

A rotor 36 for a peristaltic pump arrangement is supported by the durable housing portion 22. In the embodiment of FIG. 4, the rotor 36 comprises first and second wheels 38 and 39, supported for rotation about their central axes. A belt, ribbon, chain or similar structure 40 extends in an annular path, around a portion of the outer peripheral surface of each of the wheels 38 and 39 and has extends along a generally flat path for the length between the wheels 38 and 39. In other embodiments, the belt 40 may extend in an annular path around more than two wheels 38 and 39. In the illustrated embodiment, both wheels 38 and 39 are supported for rotation, while one of the wheels 38 is operatively connected to a drive device for driving the belt 40 around its annular path. In other embodiments, only one wheel (the drive wheel 38 that operatively connects to a drive device) may be supported for rotation, while the other wheel 39 may be non-rotating and provide a guide surface over which the belt 40 may slide, as the belt is driven.

The belt 40 has at least one (preferably a plurality) of pads or rollers 42 extending from the outer perimeter of the annular path of the belt. The pads or rollers 42 may comprise projections or nubs, rotatable wheel structures or the like on the outer peripheral surface of the belt. The wheels 38 and 39 are positioned on the durable housing portion, such that a generally flat length of the belt 40 extending between the wheels 38 and 39 is supported adjacent the length 33 of the conduit 32 and in a proximity that allows the pads or rollers 42 to contact and compress conduit 32 along the length 33, when the durable housing portion 22 is engaged with the disposable housing portion 20 and the belt 40 is driven around its annular path.

Figure 2:
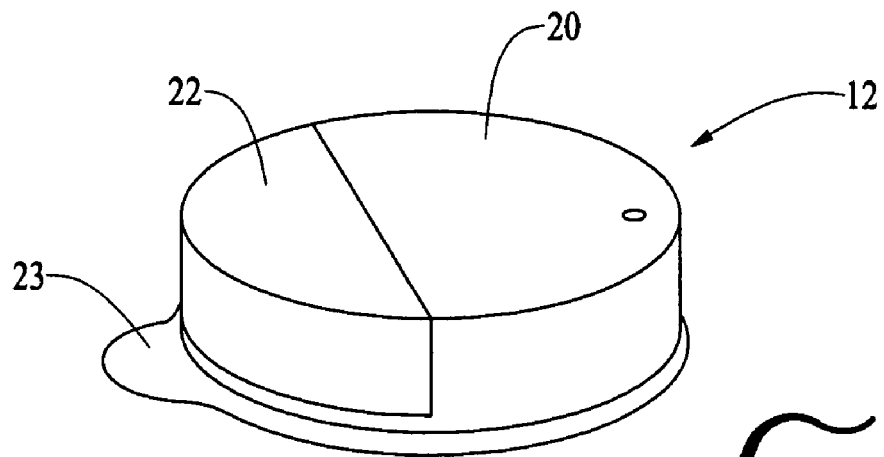
FIG. 2 is a perspective view of a delivery device according to an embodiment of the invention.

The durable housing portion 22 has a side or wall 44 (FIG. 3) that faces the disposable housing portion 20, when the durable housing portion 22 is engaged with the disposable housing portion 20 as shown in FIG. 2. The side or wall 44 defines a recess in which the wheels 38 and 39 are located. The recess in the side or wall 44 is open on the side facing the disposable housing portion for the pads or rollers 42 of the belt 40 to extend (and/or for a portion of the belt to extend, depending upon the location of the wheels 38 and 39 relative to the open side of the recess) for engaging the length 33 of the conduit 32, when the durable housing portion 22 is engaged with the disposable housing portion 20. The disposable housing portion 20 includes a side or wall 46 having an opening that faces the open side of the recess in the side or wall 44 of the durable housing portion 22, when the durable housing portion 22 is engaged with the disposable housing portion 20. The open side of the recess in the side or wall 44 is arranged to align with the open side or wall 46, to expose the length 33 of the conduit 32 and allow the pads or rollers 42 of the belt 40 to engage the length 33 of the conduit 32, when the durable housing portion 22 is engaged with the disposable housing portion 20.

A drive device 47 is supported in the durable housing portion 22 and is operatively connected to the drive wheel 38, to selectively rotate the drive wheel 38 around its central axis. The drive device 47 may comprise, for example, but not limited to a motor or other device for converting electrical power into rotational motion. Various examples of drive devices are described below. The drive device 47 may be operatively connected to the drive wheel 38, through any suitable gear, gear train, belt, shaft or other arrangement. Examples of suitable arrangements for operatively coupling an electronic motor to a rotatable drive member are described in U.S. patent application Ser. No. 11/211,095, filed Aug. 23, 2005, titled "Infusion Device And Method With Disposable Portion," which is incorporated herein by reference in its entirety.

The drive device 47 is connected to a control circuit 48 supported within the durable portion 22 of the delivery device, for controlling the operation of the drive device according to a desired infusion delivery program or profile. A delivery program or profile may be stored within a suitable electronic storage medium (not shown) located within the durable portion 22 and/or may be communicated to the delivery device 12 from other sources, such as a CCD 16 or a computer 18 (as shown in FIG. 1). In such embodiments, the delivery program or profile may be employed by the control circuit 48 to control the operation of the drive device 47 in accordance with the delivery program or profile. Alternatively or in addition, the control circuit 48 may control the drive device 47 to deliver one or more discrete volumes of the infusion medium in response to delivery demand control signals generated within the device 12 or communicated to the device 12 from other sources, such as a CCD 16 or a computer 18 (as shown in FIG. 1). Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

The durable portion 22 may contain additional electronic circuitry (not shown) for communication with external devices such as the CCD 16 or computer 18, for storage of sensor data or other data, for processing and control functions, or for other functions. The durable portion 22 may have a user interface (not shown) including one or more buttons, electronic display, or the like, and associated electronic interface circuitry to allow a user to access data and/or input data or instructions to control electronic circuitry within the durable portion 22.

The durable portion 22 may contain a battery, high energy capacitor or other electronic power source 50 for providing electrical power to the drive device 47, control circuit 48 and other electronic circuitry contained in the durable portion 22. In such embodiments, the battery, high energy capacitor or other electronic power source may be rechargeable through a recharge connector (not shown) provided on the durable portion 22. Alternatively, or in addition, the power source may be removable and replaceable with respect to the durable housing portion 22. In other embodiments, a battery, capacitor or other electronic power source (not shown) may be supported on the disposable portion 20 and connectable to the drive device 47, control circuit 48 and other electronic circuitry in the durable housing portion, through electrical connectors (not shown in FIG. 4) that make an electrical connection upon the durable portion 22 being coupled to the disposable portion 20, without additional manual manipulation. Such electrical connectors may include one or more pairs of conductive pads, where each pair of pads is connected to opposite poles of the power source and located on any suitable surface of the disposable portion 20 that engages a corresponding surface on the durable portion 22, when the durable portion 22 is engaged with the disposable portion 20. In such embodiments, the corresponding surface of the durable portion 22 includes one or more corresponding pairs of conductive pads that are electrically connected to the drive device 47, control circuit 48 and other electronic circuitry in the durable housing portion and are arranged to engage the conductive pads on the disposable portion, when the durable portion 22 is coupled to the disposable portion 20.

Figure 5:
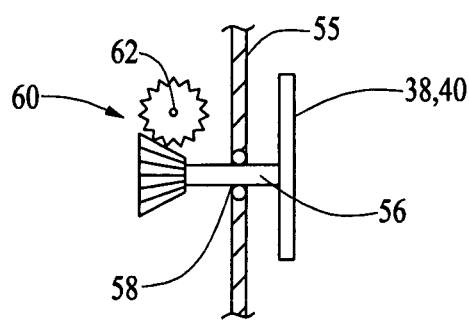
FIG. 5 is a schematic, cross-sectional view of part of a durable housing portion of the embodiment of FIG. 4.

The durable portion 22 may include an interior volume 54 that contains the drive device 47, control circuit 48, other electronic circuitry described above, gears or other linkage to operatively couple the drive device 47 to the drive wheel 38 and, in some embodiments, a power source 50. To protect those electrical and mechanical components from certain environmental conditions (such as, but not limited to, moisture, air, biological or medical fluids), the interior volume 54 of the durable portion 22 may be suitably sealed from the external environment by the housing structure 55 that forms the durable portion 22. In the embodiment in FIGS. 4 and 5, the wheels 38 and 39 and belt 40 may be supported by the durable portion 22, in a recess located outside of the interior volume 54. As shown in FIG. 5, a rotatable shaft 56 is axially connected to the drive wheel 38. The shaft 56 may extend through an aperture in a wall of the housing structure 55. One or more seals 58, such as, but not limited to, an o-ring seal may be arranged around the aperture. Accordingly, the housing structure of the durable portion 22 and the seal(s) 58 may form a suitable moisture-tight seal, air-tight seal and/or hermetic seal, to protect the electronic components located in the interior volume 54 and/or separate those components from environmental, medical or biological materials to which the disposable portion 20 is exposed during normal operation.

A linkage structure for operably coupling the drive device 47 to the shaft 56, to transfer rotational motion to the shaft 56 may be included in the sealed interior volume 54, to protect and/or separate those mechanical components from environmental or biological materials, as well. In FIG. 5, the linkage structure 60 comprises at least two engaged bevel gears or other suitable structure arranged to communicate rotational motion between a drive shaft 62 of the drive device 47 and the shaft 56, where the axes of rotation of the shafts 46 and 56 are non-parallel and may be orthogonal. Accordingly, as the drive device 47 is controlled to selectively rotate the drive shaft 62, rotational motion of the drive shaft 62 is communicated through the linkage structure 60 to provide rotational motion of the shaft 56 and, thus, rotational motion of the drive wheel 38 to selectively drive the belt 40 around its annular path.

As the belt 40 is driven around its annular path, the pads or rollers 42 engage and press against the length 33 of the conduit 32, when the durable housing portion 22 is engaged with the disposable housing portion 20. As described above, the spacing between the first and second wheels 38 and 39 provides a generally straight or flat portion of the annular path of the belt adjacent the length 33 of the conduit 32. Accordingly, as the belt 40 is selectively driven around its annular path, the pads or rollers 42 on the belt engage and slide or roll along the length 33 of the conduit 32 for at least the distance between the first and second wheels 38 and 39. The reservoir 26 (or other structural in or of the disposable housing portion) provides a generally flat surface 27 for supporting the length 33 of the conduit 32 against the pressure applied by the pads or rollers 42 of the belt 40, to compress the conduit 32 between each pad or roller 42 and the generally flat surface, as the pad or roller 42 is moved along the length 33 of the conduit 32.

Another rotor 36 and reservoir 26 configuration that may be used in a delivery device of FIGS. 2-5 is shown in FIG. 6. The rotor 36 in FIG. 6 has a plurality of pads or rollers 42 that are supported on a single rotary wheel 70. In FIG. 6, the wheel 70 comprises a structure of spokes extending from a central hub, where each spoke has an end on which a pad or roller 42 is disposed. The central hub of the wheel 70 may be coupled to a rotatable shaft similar to the rotatable shaft 56 that is coupled to the drive wheel 38 in FIG. 5. Accordingly, the wheel 70 may be selectively driven by the drive device 47 in a manner similar to the manner described above for driving the drive wheel 38 in FIG. 5.

The wheel 70 in FIG. 6 is supported for rotation about a central axis 72 at a location on the durable housing portion 22 at which the pads or rollers 42 will engage the length 33 of the conduit 32, when the durable housing portion 22 is engaged with the disposable housing portion 20. In the embodiment of FIG. 6, the length 33 of the conduit 32 is supported on a concave-curved support surface 27 of the reservoir 26 (or other structure in or of the disposable housing portion 20). The concave curvature and location of the support surface 27 in FIG. 6 may be selected to be about the same radius (or a slightly greater radius) as the radial distance of the outer surface of the pads or rollers 42 from the axis 72 of the rotary wheel 70, when the durable housing portion 22 is engaged with the disposable housing portion 20. As the rotary wheel 70 is selectively driven by the drive device 47, the pads or rollers 42 are moved around an annular, circumferential path and contact and slide or roll along the curved length 33 of the conduit 32. The pads or rollers compress the conduit 32 during their motion along the curved length 33, to provide a peristaltic pumping action (a pressure differential in the conduit 32 across the rotor 36) sufficient to draw infusion fluid from the reservoir 26, through the conduit 32 and to the injection site 35. The curvature of the support surface 27 in FIG. 6 can help maximize the length 33 of the engageable portion of the conduit 32, to improve the peristaltic pumping action. The rotor 36 configuration of FIG. 6, thus, does not require multiple wheels and does not require a belt structure as described with respect to FIG. 4. In yet further embodiments, the rotor 36 of FIG. 4 or 6 may be supported on the disposable housing portion 20 and connectable to a rotary drive device supported on the durable housing portion 22. Suitable structure for connecting a rotary drive device in one housing portion to a rotor in another housing portion is disclosed in U.S. patent application Ser. No. 11/211,095, filed Aug. 23, 2005, titled "Infusion Device And Method With Disposable Portion," which is incorporated herein by reference in its entirety.

Another peristaltic drive configuration in a delivery device 112 is shown in FIGS. 7-12. The embodiment in FIGS. 7-12 may employ a two-part housing structure, as described above, including a disposable housing portion 120 and a durable housing portion 122 that may function to engage and disengage similarly to the disposable and durable housing portions 20 and 22 described above. The two housing portions 120 and 122 are shown in an engaged orientation, in FIG. 7. The durable housing portion 122 is shown in a top-down view in FIG. 8 and in a side view in FIG. 9. The disposable portion 120 is shown in a bottom-up view in FIG. 10 and a side view in FIG. 11. Another side view of the two housing portions 120 and 122 is shown in FIG. 12, with the disposable housing portion 120 oriented to be engaged with the durable housing portion 122, but located above and separated from the durable housing portion 122.

The disposable housing portion 120 supports a reservoir 126 having an interior volume for containing a fluidic infusion medium. The reservoir 126 may be similar in structure and function to the reservoir 26 described above.

The reservoir 126 has an outlet port 130, through which the infusion medium contained within the interior of the reservoir 126 may be communicated out of the reservoir. The outlet port 130 is open to the interior volume of the reservoir 126 and may include suitable tube-connection structure. A tube-shaped conduit 132 having an internal fluid flow path is connected, at a first end, in fluid-flow communication with the outlet port 130. The conduit 132 may be made of any suitable material, including, but not limited to silicone or other plastic, metal, ceramic or composite material. At least a portion 133 of the length of the conduit 132 is made of a resilient, flexible material, such as, but not limited to a silicone or other plastic material suitable for repeated contact with pads or rollers of a peristaltic rotor, as described below, to repeatedly compress and return the fluid flow path within the length portion 133 of the conduit 132. In some embodiments, the entire length of the conduit 132 is made of the resilient, flexible material.

A second end of the conduit 132 is connected in fluid flow communication with an injection site 135 located on the disposable housing portion 120. The injection site 135 may be similar to the injection site 35 described above. For example, the injection site 135 may include a needle inserter device for inserting a hollow needle or cannula into a patient-user's skin, when the delivery device 112 is secured to a patient-user's skin. Examples of needle inserter devices that may be used for moving a hollow needle or cannula into a patient-user and connecting the hollow needle or cannula in fluid flow communication with a reservoir are described in U.S. patent application Ser. No. 11/211,095, filed Aug. 23, 2005, and U.S. Patent Application No. 60/839,840, titled "Infusion Medium Delivery System, Device And Method With Needle Inserter And Needle Inserter Device Method", filed Aug. 23, 2006, each of which is incorporated herein by reference. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. In further embodiments, other suitable needle or cannula inserter devices may be employed. In yet further embodiments, a set of micro-needles may be employed, instead f a hollow needle or cannula.

In the embodiment shown in FIGS. 8-12, the length portion 133 of the conduit 132 is supported on a surface 127 of the disposable housing portion 120, at a location arranged to be contacted and compressed by one or more pads or rollers of a peristaltic rotor, when the durable housing portion 122 is engaged with the disposable housing portion 120. The length portion 133 may extend in a circular path around at least a portion of the circumference of a circle (as shown in FIG. 10) having a radius about the same as the radius at which one or more wheels or pads of a rotor of a peristaltic pumping arrangement (described below) are located. As shown in FIG. 11, the conduit support surface 127 may be located within a recessed portion, such as an annular groove, provided on a side of the disposable housing portion 120 that faces and engages an opposite-facing side of the durable housing portion 122, when the disposable housing portion 120 and the durable housing portion 122 are engaged in the manner shown in FIG. 7. In such embodiments, the annular groove may have a radius and width sufficient to receive one or more wheels or pads of a rotor of a peristaltic pumping arrangement (described below). The location of the conduit 132 in an annular groove may help to avoid damage to the conduit during use, storage or shipping.

The durable housing portion supports a rotor 136 of a peristaltic pumping arrangement. The rotor 136 comprises a rotor wheel 137 that supports at least one roller or pad 142, and preferably, a plurality of rollers or pads 142 located at spaced intervals around the perimeter of the rotor wheel 137. The rollers or pads 142 may comprise rotatable wheels, projections, nubs or the like. In embodiments in which the rollers or pads 142 are rotatable wheels, each wheel is supported for rotation on a respective spoke of the rotor wheel 137, where the axis of rotation of each wheel is orthogonal to (and may be perpendicular to) the axis of rotation of the rotor wheel 137.

That arrangement allows the rollers or pads 142 to readily align with and operatively engage the flexible portion 133 of the conduit 132, when the durable housing portion 122 is engaged with the disposable housing portion 120. In the embodiment of FIG. 8, the rotor 136 includes three rollers or pads 142. In other embodiments, any suitable number rollers or pads 142 may be employed. The rollers or pads 142 are located at a radial distance from the axis 147 of the rotor 136 that is about the same as the radius of the circle circumscribed by the flexible portion 133 of the conduit 132 and the radius of the annular groove for the support surface 127 on the disposable housing portion 120.

The rotor 136 is operatively coupled to a drive device 146, for selective rotation about the rotor axis 147 by the drive device 146. The drive device 146 is connected to a control circuit 148 supported within the durable portion 122 of the delivery device, for controlling the operation of the drive device according to a desired infusion delivery program or profile. A delivery program or profile may be stored within a suitable electronic storage medium (not shown) located within the durable portion 122 and/or may be communicated to the delivery device 12 from other sources, such as a CCD 16 or a computer 18 (as shown in FIG. 1). In such embodiments, the delivery program or profile may be employed by the control circuit 148 to control the operation of the drive device 146 in accordance with the delivery program or profile. Alternatively or in addition, the control circuit 148 may control the drive device 146 to deliver one or more discrete volumes of the infusion medium in response to delivery demand control signals generated within the device 12 or communicated to the device 12 from other sources, such as a CCD 16 or a computer 18 (as shown in FIG. 1). Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

The durable portion 122 may contain additional electronic circuitry (not shown) for communication with external devices such as the CCD 16 or computer 18, for storage of sensor data or other data, for processing and control functions, or for other functions as described above with respect to the circuitry in durable housing portion 22. The durable portion 122 may have a user interface (not shown) including one or more buttons, electronic display, or the like, and electronic interface circuitry to allow a user to access data and/or input data or instructions to control electronic circuitry within the durable portion 122.

The durable portion 122 may contain a battery, high energy capacitor or other electronic power source 150 for providing electrical power to the drive device 146, control circuit 148 and other electronic circuitry contained in the durable portion 122. In such embodiments, the battery, high energy capacitor or other electronic power source may be rechargeable through a recharge connector (not shown) provided on the durable portion 122. Alternatively, or in addition, the power source may be removable and replaceable with respect to the durable housing portion 122.

In other embodiments, such as shown in FIG. 13, a battery, capacitor or other electronic power source 150' may be supported on the disposable portion 120'. More specifically, in the embodiment of FIG. 13, a disposable housing portion 120' and a durable housing portion 122' function in a manner similar to the disposable housing portion 120 and durable housing portion 122 described above. However, in FIG. 13, the power source 150' is electrically connectable, through connectors 151' and 152', to a drive device 146', a control circuit 148' and other electronic circuitry in the durable housing portion 122' (similar to the drive device 146, control circuit 148 and other electronic circuitry in the durable housing portion 122 described above). The electrical connectors 151' and 152' may comprise any suitable structure that makes an electrical connection upon the durable portion 122' being coupled to the disposable portion 120', without additional manual manipulation.

In the embodiment shown in FIG. 13, the electrical connector 151' comprises a pair of electrical leads extending from the positive and negative poles of the power source 150', with a conductive pad on an exposed end of each lead. The electrical connector 152' comprises a pair of electrical conductors connected to one or more of the control circuit 148', the drive device 146' and other electronic circuitry in the durable housing portion 122'. The embodiment of FIG. 13 includes a reservoir 126', conduit 132' and a rotor 136' (similar to the reservoir 126, conduit 132 and rotor 136 described above).

In the embodiments of FIGS. 8-13, the durable portion 122, 122' may include an interior volume 154, 154' that contains the drive device 146, 146' control circuit 148, 148' and other electronic circuitry as described above. In addition, the interior volume 154, 154' may contain gears or other linkage structure 160, 160' (similar to the linkage structure 60 described above) to operatively couple the drive device 146, 146' to a rotatable rotor shaft 156, 156'. To protect those electrical and mechanical components from certain environmental conditions (such as, but not limited to, moisture, air, biological or medical fluids), the interior volume 154, 154' of the durable portion 122, 122' may be suitably sealed from the external environment by the housing structure 155, 155' that forms the durable portion 122, 122'.

In the embodiments in FIGS. 8-13, the rotor 136, 136' may be supported by the durable portion 122, 122', outside of the interior volume 154, 154'. The rotatable shaft 156, 156' is axially connected to the rotor 136, 136'. The shaft 156, 156' may extend through an aperture in a wall of the housing structure 155, 155'. One or more seals 158, 158', such as, but not limited to, an o-ring seal may be arranged around the aperture. Accordingly, the housing structure of the durable portion 122, 122' and the seal(s) 158, 158' may form a suitable moisture-tight seal, air-tight seal and/or hermetic seal, to protect the electronic components located in the interior volume 154, 154' and/or separate those components from environmental, medical or biological materials to which the disposable portion 120, 120' is exposed during normal operation.

Accordingly, as the drive device 146, 146' is controlled to selectively rotate the drive shaft 162, 162', rotational motion of the drive shaft 162, 162' is communicated through the linkage structure 160, 160' to provide rotational motion of the shaft 156, 156' and, thus, rotational motion of the rotor 136, 136' to selectively drive the rollers or pads on the rotor through an annular path.

As the rollers or pads on the rotor 136, 136' are driven in their annular path, the rollers or pads engage and compress the conduit 132, 132' during their motion along the annular path to provide a peristaltic pumping action (a pressure differential in the conduit 132, 132' across the rotor 136, 136')

sufficient to draw infusion fluid from the reservoir 126, 126', through the conduit 132, 132' and to the injection site 135, 135'.

Figure 14:
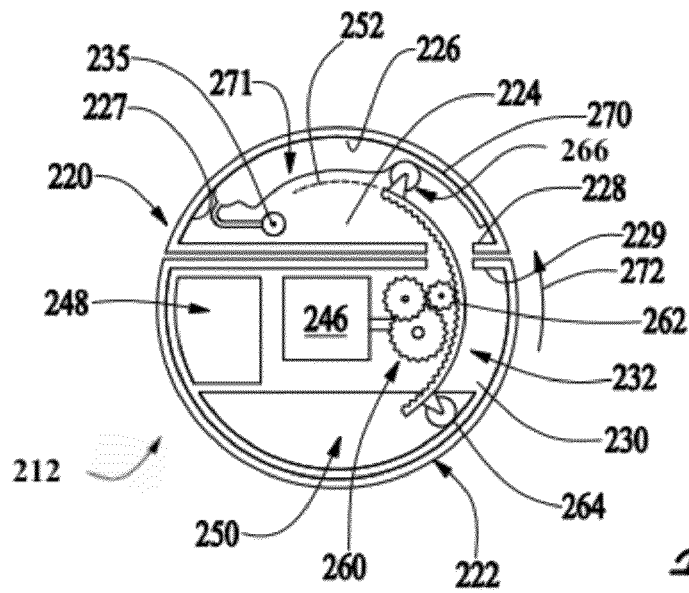
FIG. 14 is a schematic cross section view of a delivery device according to another embodiment of the invention.

In the embodiments of FIGS. 4-13, a compression structure comprising at least one roller or pad of a rotor 136, 136' is arranged to engage and compress a portion of the conduit 132, 132' that extends from the infusion medium reservoir 126, 126'. According to a further embodiment, a compression structure, such as at least one roller or pad, is arranged to compress the infusion medium reservoir, itself. For example, an embodiment of a delivery device 212 as shown in FIG. 14 includes a disposable housing portion 220 and a durable housing portion 222, similar in structure and function to the disposable and durable housing portions 20 and 22, respectively, discussed above. The disposable housing portion 220 and the durable housing portion 222 are configured to be engaged, as shown in FIG. 14, for operation, yet be separable (as described above with respect to the disposable and durable housing portions 20 and 22).

The disposable housing portion 220 has an interior volume 224 that contains a reservoir 226. The reservoir 226 is arranged to abut against a rigid surface 227 within the disposable housing portion 220. In the embodiment shown in FIG. 14, the reservoir 226 abuts against the inner surface 227 of the outer wall of the structure that forms the disposable housing portion 220. Also in the embodiment shown in FIG. 14, the inner surface 227 is curved, corresponding to the curvature of the outer wall of the structure that forms the disposable housing portion 220. In other embodiments, the rigid surface 227 against which the reservoir 226 abuts may be a surface of another wall (not shown) of the disposable housing portion 220 or the surface of another structure (not shown) located within the interior volume 224 of the disposable housing portion 220.

The reservoir 226 may comprise a flexible bag-like container, a tube-like structure or other container structure having at least one flexible wall for receiving compression pressure from a track roller, as described below. The reservoir 226 includes an interior volume for containing an infusion medium. In one example embodiment, the reservoir 226 comprises a flexible bag-like container made of a flexible plastic, metal or composite material, suitably compatible with the infusion medium. A conduit having an internal fluid flow path is coupled in fluid flow communication with the interior of the reservoir 226 and an injection site 235, for providing a fluid flow path from the reservoir to the injection site. The injection site 235 may be similar to the injection site 35 or 135 described above.

The housing structure of the disposable housing portion 220 has a wall 228 that faces an opposite-facing wall 229 of the durable housing portion 222, when the disposable housing portion 220 and the durable housing portion 222 are engaged as shown in FIG. 14. The wall 228 of the disposable housing portion 220 is provided with an opening that aligns with a corresponding opening of the wall 229 of the durable housing portion, when the disposable housing portion 220 and the durable housing portion 222 are engaged as shown in FIG. 14.

The durable housing portion has an interior volume 230 that contains a movable track 232 (such as a rack of a rack and pinion arrangement), a drive device 246, drive control electronics 248, other electronics (not shown), a power source 250 and linkage gears or other linkage structure 260 for operatively coupling the drive device 246 to the track 232, to move the track 232 along an arched path. The drive device 246 may comprise a drive device as described above with respect to drive device 47. Similarly, the drive control electronics 248, other electronics (not shown) and power source 250 may comprise drive electronics 48, other electronics and a power source 50 as described above with respect to the embodiment of FIGS. 2-5.

In the embodiment of FIG. 14, the track 232 is curved to correspond (approximate) the curvature of the inner surface 227 in the disposable housing portion 220. The track 232 is supported to move in an arched path 252 that extends along the direction of curvature of the track 232. The track 232 has a surface provided with serrations or teeth configured for engaging corresponding serrations or teeth on an engagement gear 262 (such as a pinion gear of a rack and pinion arrangement) of the linkage 260. The engagement gear 262 is operatively coupled through the rest of the linkage 260 to be selectively, rotatably driven by the drive device 246, for example, but not limited to the linkage 60 that operatively couples the drive device 47 to selectively, rotatably drive the wheel 38 described above. In the embodiment of FIG. 14, the track 232 is provided with serrations or teeth the curved surface of the track that forms a concave shape. However, in other embodiments, the track 232 may be provided with serrations or teeth along its convex curved side or on the surface facing out of the page or the surface facing into the page (relative to the orientation shown in FIG. 14), for engaging an engagement gear 262 suitably located adjacent the serrated or toothed surface of the track 232.

The track 232 is configured to extend through the aperture in the wall 229 of the durable housing portion 222, such that a portion of the curved length of the track 232 is located inside of the internal volume of the durable housing portion 222 and a further portion of the curved length of the track 232 extends out of the aperture in the wall 229. When the disposable housing portion 220 and the durable housing portion 222 are engaged, as shown in FIG. 14, the portion of the track 232 that extends out of the aperture in the wall 229 of the durable housing portion 222 is arranged to extend into the aperture in the wall 228 of the disposable housing portion 220.

The track 232 may be supported for movement along the arcuate path 252 by a combination of the engagement gear 262 and one or more of a further gear (not shown) engaging the convex side of the curved track 232 or one or more support rollers or pads 264 connected to the track 232 and arranged to slide or roll along a curved surface such as the interior surface of the structure that forms the outer wall of the durable housing portion 222. Alternatively, or in addition, such support rollers or pads 264 may be arranged to roll along another curved surface of or within the durable housing portion 222. Alternatively, or in addition, the track 232 may be guided within one or more grooves, channels or other guide structures (not shown) formed on one or both of the durable housing portion 222 and disposable housing portion 220, for engaging the track 232 and maintaining the track 232 along the arcuate path 252.

A compression mechanism comprising t least one compression pad or roller 266 is supported on the portion of the track 232 that extends into the interior of the disposable housing portion, when the disposable housing portion 220 and the durable housing portion 222 are engaged as shown in FIG. 14. The compression pad(s) or roller(s) 266 may be arranged to impart a compression force on a flexible wall of the reservoir 226, when the disposable housing portion 220 and the durable housing portion 222 are engaged as shown in FIG. 14.

In particular, the compression pad(s) or roller(s) 266 may engage a flexible wall of the reservoir 226 and impart a compression force directed toward the surface 227 against which the reservoir 226 is abutted. The compression force imparted by the compression pad(s) or roller(s) 266 is sufficient to compress the portion of the reservoir 226 that is located between the compression pad(s) or roller(s) 266 and the surface 227. The width dimension (in the direction into and out of the page in the orientation shown in FIG. 14) of the compression pad(s) or roller(s) 266 is at least as great as the width dimension (in the direction into and out of the page in the orientation shown in FIG. 14) of the reservoir 226. The compression pad(s) or roller(s) 266 are arranged to slide or roll along the reservoir 226 and compress the reservoir, as the track 232 is moved in the arcuate path 252, in the direction of arrow 272. Accordingly, as the compression pad(s) or roller(s) 266 compress a portion 270 of the reservoir 226, as shown in FIG. 14, the internal volume of an infusion-medium-containing portion 271 of the reservoir 226 reduces and the pressure within the infusion-medium-containing portion of the reservoir 226 increases to cause infusion medium to be forced out of the reservoir 226, toward the injection site 235.

Figure 15:
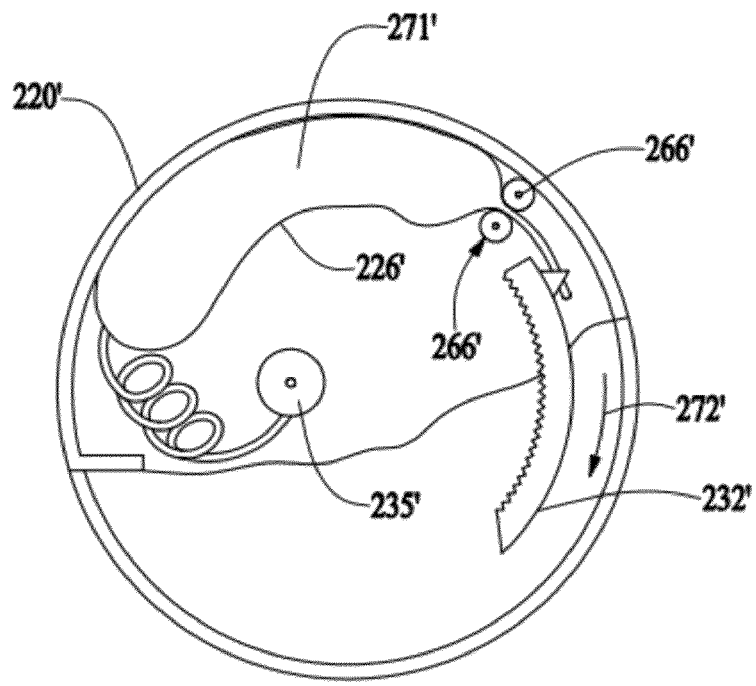
FIG. 15 is a schematic, cross section view of part of another disposable housing portion for a delivery device of FIG. 14, that may be used in place of the disposable housing portion shown in FIG. 14.

While the compression pad(s) or roller(s) 266 in FIG. 14 are coupled to the moveable track 232, in other embodiments, one or more compression pad(s) or rotatable roller(s) may be supported in a fixed relation (with roller axis in a fixed location) relative to the disposable housing portion 220, while the reservoir may be coupled to the moveable track. For example, FIG. 15 shows an embodiment in which a pair of compression pads or rollers 266' are arranged adjacent each other and secured to the disposable housing portion 220 in a fixed location (although they may be rotatable) with respect to the disposable housing portion 220. The width dimension (in the direction into and out of the page in the orientation shown in FIG. 15) of the compression pads or rollers 266' is at least as great as the width dimension (in the direction into and out of the page in the orientation shown in FIG. 15) of the reservoir 226'.

The embodiment of FIG. 15 includes a reservoir 226' and a moveable track 232', which may be similar to the reservoir 226 and track 232 described above with respect to FIG. 14. However, in FIG. 15, the reservoir 226' is secured to the portion of the track 232' that extends into the disposable housing portion, when the disposable housing portion 220' and the durable housing portion 222' are engaged (in a manner similar to that shown in FIG. 14). Also, in the embodiment of FIG. 15, the drive device and linkage (246 and 260 in FIG. 14) are configured to selectively move the track 232' in the direction of arrow 272' (opposite to the direction of arrow 272 in FIG. 14), to selectively pull a portion of the reservoir 226' through a space between the compression pads or rollers 266'.

The spacing between the compression pads or rollers 266' is selected to allow the compression pads or rollers 266' to compress the portion of the reservoir 226' located between the pads or rollers, to substantially deplete infusion medium from that portion of the reservoir and reduce the infusion-medium-containing portion of the reservoir 226', as the reservoir is pulled through the space between the compression pads or rollers 266' by movement of the track 232' in the direction of arrow 272'. Accordingly, as the reservoir 226' is compressed by the compression pad(s) or roller(s) 266', the internal volume of an infusion-medium-containing portion 271' of the reservoir 226' reduces and the pressure within the infusion-medium-containing portion of the reservoir 226' increases to cause infusion medium to be forced out of the reservoir 226', toward the injection site 235'. The reservoir 226' and moveable track 232' of FIG. 15 may be used in place of the reservoir 226 and moveable track 232 of FIG. 14.

In further embodiments, a reservoir 226' may extend between (and be compressed by) a pair of compression rollers or pads 266' similar to the arrangement shown in FIG. 15. However, in further embodiments, the compression pads or rollers 266' comprise at least one (and, preferably, two) rotatable roller members, and where one or both of the roller members is (are) operatively coupled to a drive device for rotation of the roller member(s). By rotatably driving the roller member(s) 266' with a drive device, the depleted portion 271' of the reservoir 226' may be driven through the space between the roller member(s) 266', to further reduce the internal volume of an infusion-medium-containing portion 271' of the reservoir 226' and, thus, increase the pressure within the infusion-medium-containing portion of the reservoir 226' to cause infusion medium to be forced out of the reservoir 226', toward the injection site 235'. Also, while embodiments shown in FIGS. 14 and 15 employ a track 232 having a curved shape, to accommodate the circular shape of the interior of the disposable housing portion 220 and minimize space usage, other embodiments may employ a track 232 having a generally straight length along its serrated or toothed side.

Figure 16:
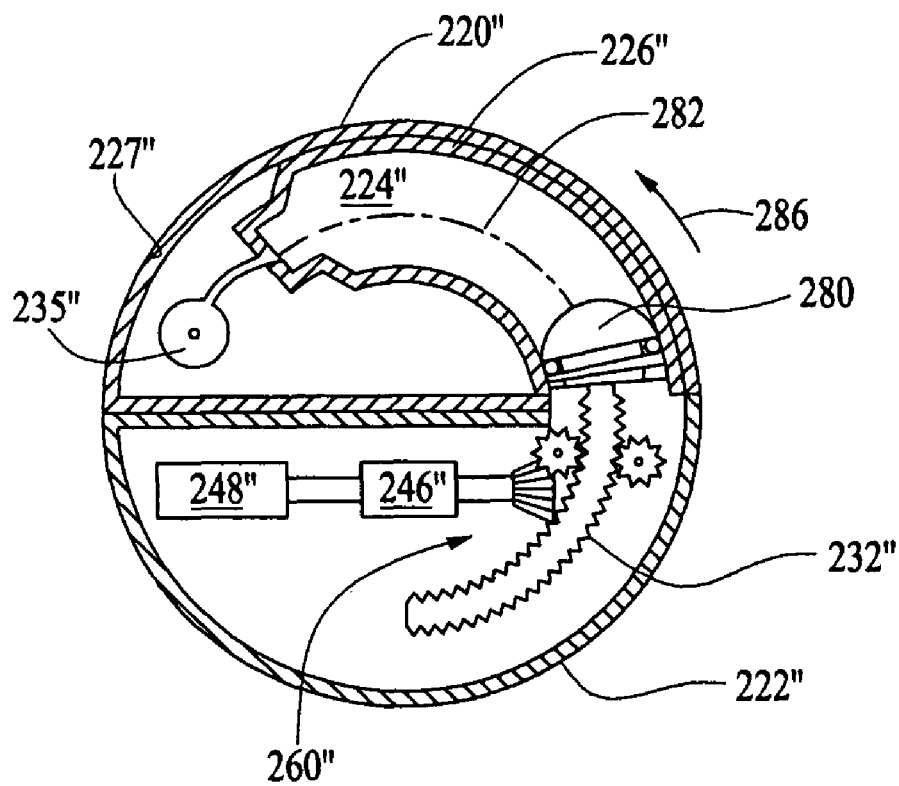
FIG. 16 is a schematic cross section view of a delivery device according to another embodiment of the invention.
Figure 17:
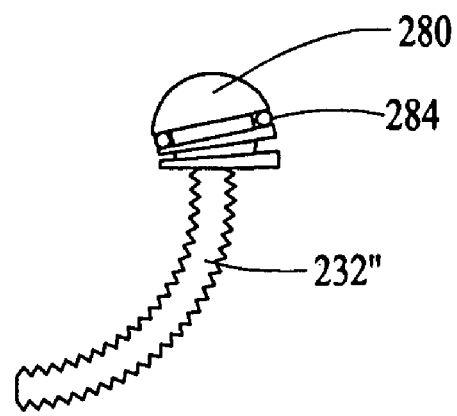
FIG. 17 is a side view of a plunger head and moveable track for a delivery device of FIG. 16.

A further embodiment of a delivery device 212" in FIGS. 16 and 17 is similar in various structural and functional features as the delivery device 212 described above, in that the delivery device 212" includes a disposable housing portion 220" and a durable housing portion 222" (similar to the disposable housing portion 220 or 220' and durable housing portion 222 or 222' described above). In FIGS. 16 and 17, a track 232" (similar to the track 232 or 232' discussed above) operates with a plunger head 280 attached to or engaged with the end of the track portion that extends into the disposable housing portion 220". The track 232" may be operatively coupled to a drive device 246", through suitable linkage structure 260", as described above with respect to the tack 232, drive device 246 and linkage structure 260 in FIG. 14.

A reservoir 226" is located in the disposable housing portion 220" and has an interior volume for containing an infusion medium. The reservoir 226" may comprise a rigid, tubular structure or channel having a curved interior volume, where the curved interior volume extends along a curved longitudinal direction and has a radius of curvature about the same as the radius of curvature of the track 232". The interior volume of the reservoir 226" maybe connected to an injection site 235". For example, the reservoir 226" may comprise structure and functionality similar to the reservoirs described in co-pending U.S. Patent Application Ser. No. 60/839,822, filed Aug. 23, 2006, titled "Infusion Medium Delivery Device And Method For Driving Plunger In Reservoir.", but having a curved interior volume. In one embodiment, a plunger head 280 may be disposed within the reservoir, such that one end of the track 232" is arranged to abut (engage) the plunger head 280, when the durable housing portion 222" is engaged with the disposable housing portion 220", as shown in FIG. 16, yet separate (disengage) from the plunger head 280 when the durable housing portion 222" is separated from the disposable housing portion 220". In another embodiment, the plunger head 280 may be fixed to one end of the track 232" and may be inserted into the reservoir 226", when the durable housing portion 222" is engaged with the disposable housing portion 220", as shown in FIG. 16, and may be withdrawn from the reservoir 226" when the durable housing portion 222" is separated from the disposable housing portion 220".

In the embodiment shown in FIG. 16, the reservoir 226" comprises a curved tubular structure having a curved central axis 282 extending in the longitudinal direction of the tubular structure. The curved tubular structure of the reservoir 226" in FIG. 16 has an outer radius of curvature approximately equal to the radius of curvature of the inner wall surface 227" of the disposable housing portion 220". The curvature of the reservoir 226", thus, may be selected to help maximize the efficient use of the interior volume 224" of the disposable housing portion 220", by minimizing unused, open space within the interior volume 224" without reducing the interior volume of the reservoir. Accordingly, a curved reservoir may be employed to help minimize certain dimensions of the delivery device 12", without reducing the reservoir capacity.

The plunger head 280 in FIGS. 16 and 17 has a suitable shape and dimension to be moveable within the interior volume of the reservoir 226". The plunger head 280 may include one or more seals 284, such as, but not limited to o-ring seals, to provide a fluid seal between the outer peripheral surface of the plunger head and the inner surface of the reservoir 226". When engaged with the end of the track 232", the plunger head 280 is moveable in the direction of arrow 286, upon the track 232" being driven by the drive device 246" in the direction of arrow 286. As the plunger head 280 is moved within the reservoir 226" in the direction of arrow 284, the infusion-medium-containing volume of the reservoir 226" is reduced and the pressure within the infusion-medium-containing portion of the reservoir 226" is correspondingly increased, to cause infusion medium to be forced out of the reservoir 226", toward the injection site 235".

Figure 18:
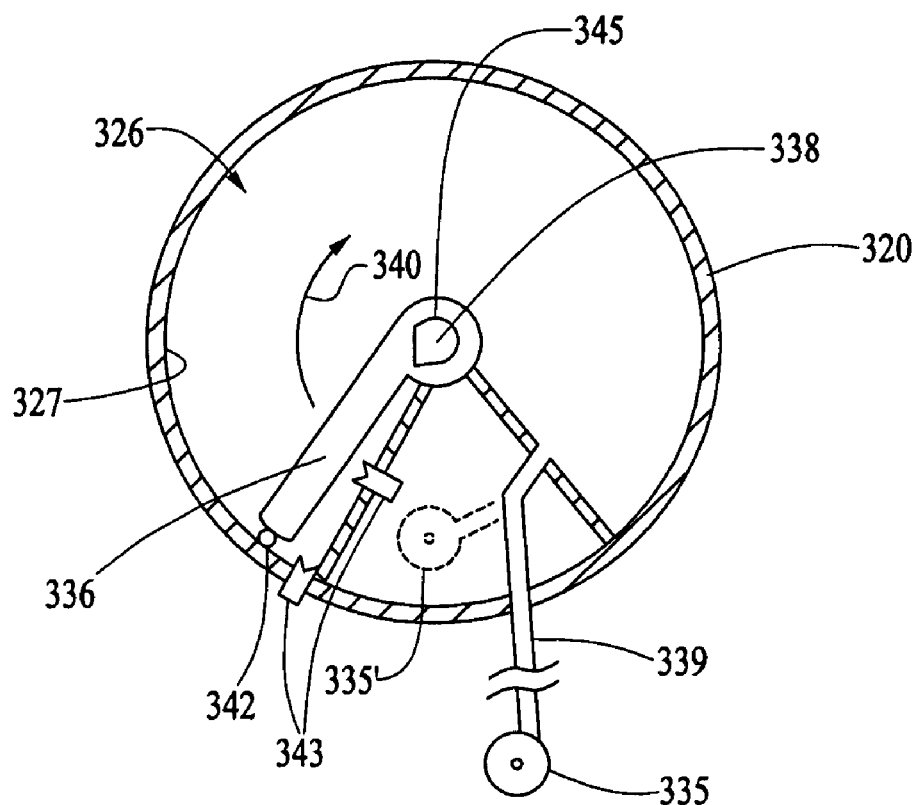
FIG. 18 is a schematic cross section view of a disposable portion of a delivery device according to another embodiment of the present invention.

A delivery device 312 according to a further embodiment of the present invention includes a reservoir having a generally disk-like shape with a circular or elliptical cross-section, or other smooth cross-sectional shape, to accommodate sealing between a reservoir plunger and the inner surface of the reservoir. In the embodiment of FIG. 18, a disposable housing portion 320 comprises a reservoir 326 that has an enclosed interior volume with a generally circular cross-sectional shape (forming a partial circle), such that the inner wall surface of the reservoir has a radius of curvature that forms at least a partial circle. The disposable housing portion 320 may be formed of any suitable material, such as described above with respect to the disposable housing portion 20.

In FIG. 18, the inner wall surface 327 of the reservoir 326 is (or has the same shape and similar dimension as) the outer peripheral wall of the reservoir 326. Accordingly, the volume of the reservoir 326 may be maximized for a given outer dimension of the disposable housing portion 320.

A plunger in the form of a rotor arm 336 is supported for rotation within the reservoir 326. In FIG. 18, the rotor arm 336 is supported at one end on a rotation axis 338, about which the arm 336 may rotate in the direction of arrow 340. The rotor arm 336 has a width dimension (extending into and out of the page, in the orientation shown in FIG. 18) about as great as the width dimension (into and out of the page, in the orientation shown in FIG. 18) of the reservoir 326, such that the rotor arm spans the full width (into and out of the page, in the orientation shown in FIG. 18) of the reservoir 326. The rotor arm 336 may be made of any suitably rigid material, including, but not limited to a metal, plastic, ceramic or composite material, or combinations thereof.

In the embodiment of FIG. 18, the rotor arm axis 338 is coaxial with the axis of the circular shape of the inner wall surface of the reservoir (which may be the same surface as, or coaxial with, the inner wall surface 327 of the disposable housing portion 320). The arm 336 extends from the rotation axis 338, radially outward a distance about equal to (or slightly less than) the radius of the inner wall surface of the reservoir 326, toward the inner wall surface of the reservoir. One or more seals 342 may be secured to the second end of the arm 336, to provide a fluid seal between the inner wall surface of the reservoir and the arm 336. One or more seals (not shown) may be provided on the surfaces of the arm 336 facing into and out of the page in the orientation shown in FIG. 18, to provide a fluid seal between the arm 336 and the bottom and top surfaces of the reservoir 326 (with respect to the orientation shown in FIG. 18). One or more air passages 343 may be provided between the interior of the reservoir 326 and an external environment, to equalize pressure within the reservoir 326, as the infusion medium is driven out of the reservoir or filled or re-filled into the reservoir. The air passages may be covered with an air-permeable material that inhibits the passage of infusion media, but allows the passage of air. Examples of structures that permit air-flow, but that inhibit fluids can be found in U.S. patent application Ser. No. 10/328, 393 filed Dec. 22, 2003, and entitled "Reservoir Connector," and U.S. patent application Ser. No. 10/699,429 filed Oct. 31, 2003, and entitled "External Infusion Device with a Vented Housing," both of which are incorporated herein by reference in their entirety.

An outlet 341 is provided in fluid flow communication with the interior volume of the reservoir 326 and couples to a conduit 339 that is in fluid flow communication with an injection site 335. The injection site 335 may be similar to the injection site 35, 135 and 235 described above. As the arm 336 is selectively driven in the direction of arrow 340, the pressure of the infusion medium within the interior of the reservoir 326 increases and the infusion medium is forced out of the outlet 341 and through the conduit 339 to the injection site 335. In the embodiment shown in FIG. 18, the conduit 339 extends out from the disposable housing portion, to an injection site 335 that is external to the disposable housing portion. In further embodiments, the injection site 335 may be located within the disposable housing portion, for example, as shown in broken lines at 335' in FIG. 18.

Figure 19:
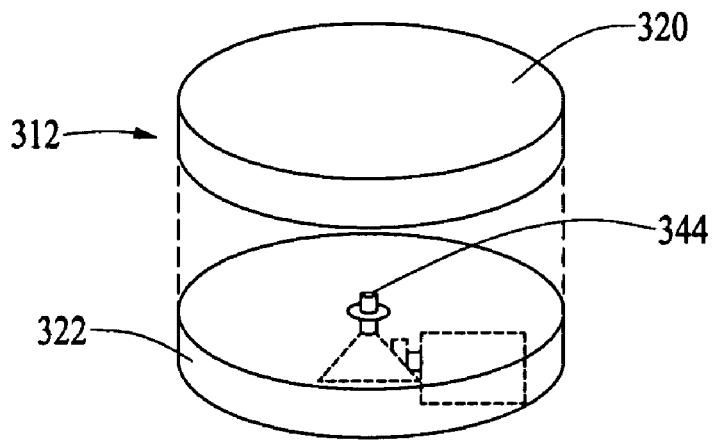
FIG. 19 is a perspective view of a delivery device including a disposable portion of FIG. 18 and a durable portion in a separated relation.

A durable housing portion 322 shown in FIG. 19 is configured to engage and operatively couple to the disposable housing portion 320 in FIG. 18. The durable housing portion 322 may include an enclosed interior volume that contains a drive device, drive control electronics, other electronics, a power source and linkage structure, as described above with respect to the durable housing portion 22 of FIG. 4.

In the embodiment of FIG. 19, the drive device within the durable housing portion is operatively coupled, through suitable linkage structure as described above, to rotatably drive a rotatable shaft 344. The rotatable shaft 344 is supported for rotation by the durable housing portion 322 and extends through an aperture in a wall of the durable housing portion 322. One or more seals, such as, but not limited to o-ring seals, may be disposed around the aperture in the durable housing portion wall through which the shaft 344 extends.

The end of the shaft 344 that extends outside of the durable housing portion 322 may include a mating connector, for engaging and operatively mating with a corresponding mating connector coupled to the rotor arm 336. For example, the shaft 344 may have a non-circular cross-section (cross-section in the plane perpendicular to the longitudinal axis of the shaft 344) that mates with an axial-directed aperture 335 in the arm 336. The aperture 335 has a non-circular cross-section shape that corresponds to the cross-section shape of the shaft 344 to allow the shaft 344 to be inserted into the aperture 335 and to rotate the arm 336 with rotation of the shaft 344. In the embodiment of FIGS. 18 and 19, the non-circular cross-sectional shape of the shaft 344 and the aperture 335 is generally a "D" shape. However, other embodiments may employ other suitable, non-circular shapes, including, but not limited to, oval, elliptical, polygonal, star, cross shapes or the like.

Figure 20:
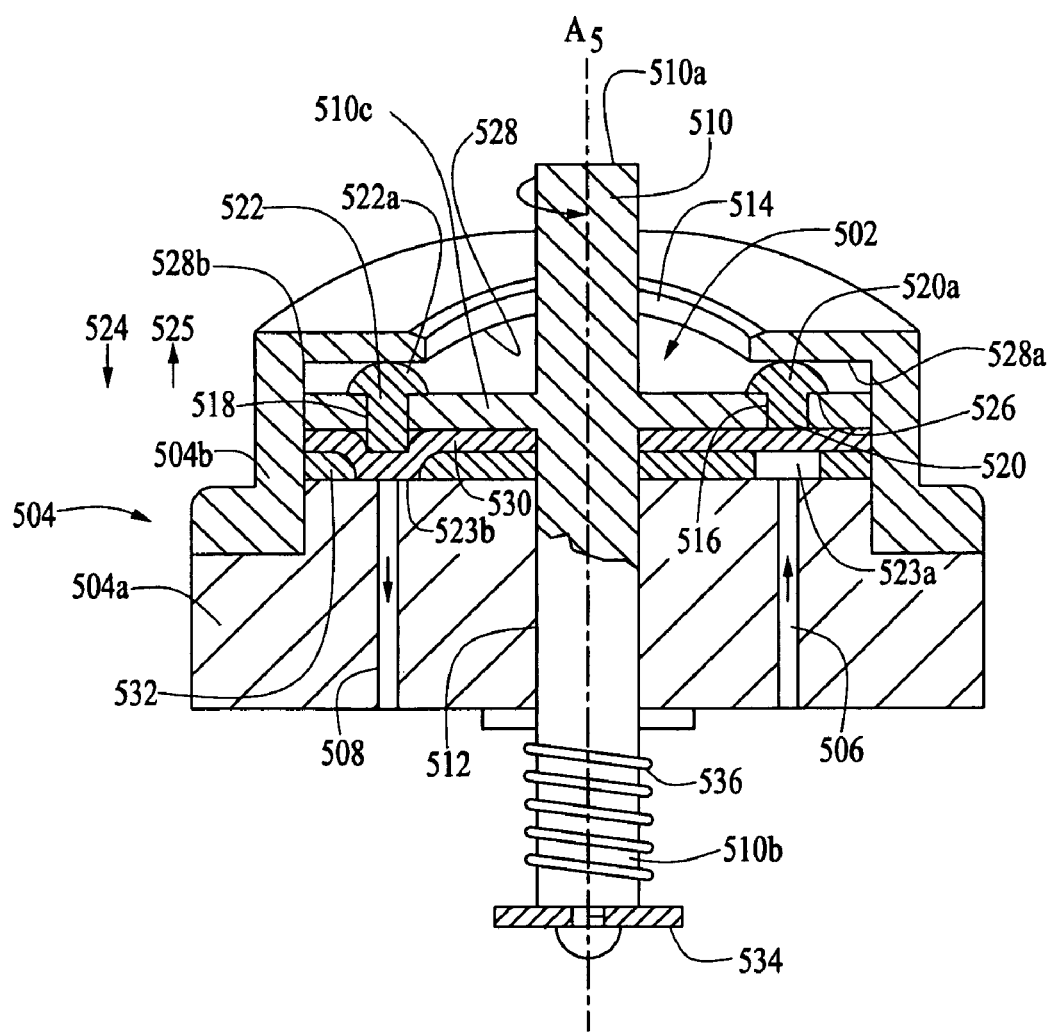
FIG. 20 is a cross-sectional view of a portion of a delivery device according to a further embodiment of the invention.
Figure 23:
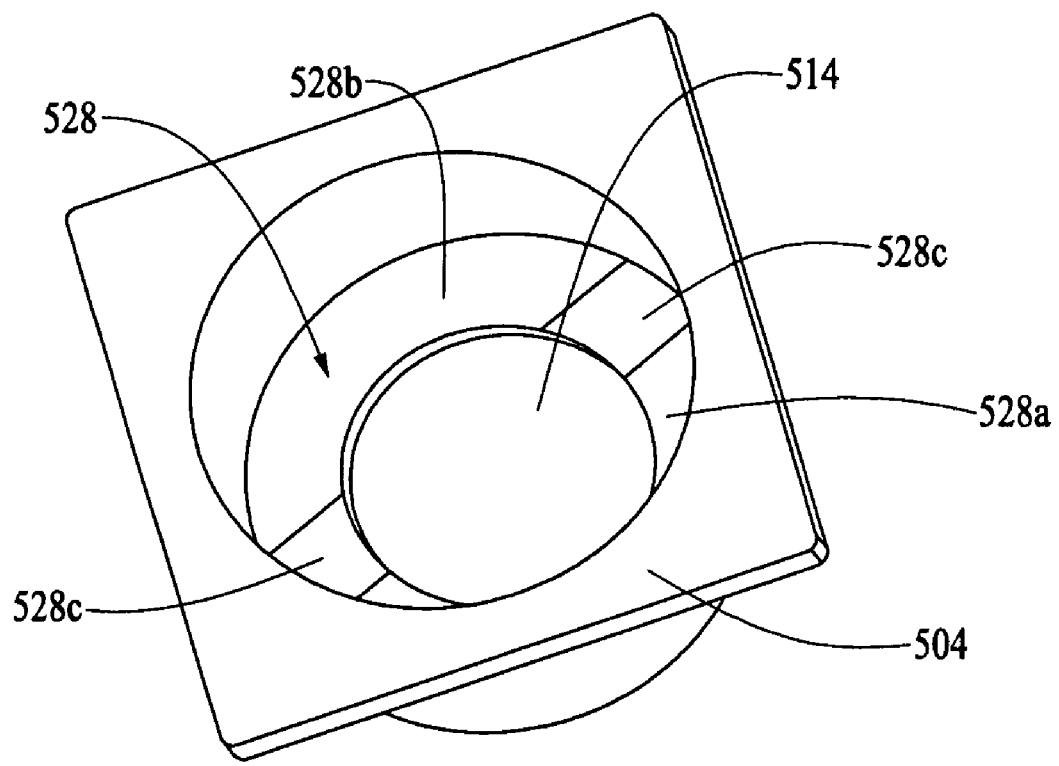
FIG. 23 is a perspective view of a cam housing according to the embodiment of FIG. 20.

Accordingly, in the embodiment of FIGS. 18 and 19, the drive device within the durable housing portion is operatively coupled, through suitable linkage structure, to rotatably drive a rotatable shaft 344. FIG. 20 shows another embodiment in which a similar drive device within a similar durable housing portion may be operatively coupled, through suitable linkage structure, to rotatably drive a rotary shaft to selectively drive fluid from a reservoir.

The structure in FIG. 20 includes a rotor 502 supported for rotation relative to a housing 504, about an axis $A_5$. The housing 504 may be located within the disposable housing portion 20 and/or may be a section of the disposable housing portion 20 described above with respect to FIGS. 2 and 3. The housing 504 may be selectively engaged with and disengaged from a durable housing portion that contains a drive device, as described above with respect to the drive device 47.

In the embodiment of FIG. 20, the housing 504 has a base portion 504a and a cover portion 504b. The base portion 504a and cover portion 504b may be separate elements that are connected together or may be formed as a unitary structure. In embodiments in which the base portion 504a and cover portion 504b are separate elements that are connected together, one or more seals, such as, but not limited to, o-ring or annular, flat gasket seals, may be provided between the base portion 504a and the cover portion 504b, to inhibit leakage of fluid (such as an infusion medium) between those elements, when they are connected together.

First and second channels 506 and 508 extend through the base portion 504a of the housing 504, in a spaced relation relative to each other and to the axis $A_5$ of the rotor 502. In the embodiment of FIG. 20, the channels 506 and 508 are located at 180 degrees around the axis $A_5$, relative to each other. However, in other embodiments, the channels may be located at other suitable spacing around the axis $A_5$, relative to each other.

The first and second channels 506 and 508 in the base portion 504a of the housing 504 form fluid inlet and outlet channels, respectively, as described below. The cover portion 504b of the housing 504 has an interior volume and a cam surface 528 that includes a cam lobe 528b for contacting cams, a non-camming surface portion 528a that does not move the cams and a ramp portion 528c connecting the non-camming surface with the cam lobe. One end of each of the first and second channels 506 and 508 is open to the interior volume of the housing 504.

The rotor includes a shaft 510 that extends through a channel 512 in the base portion 504a and through an opening 514 in the cover portion 504b of the housing 504. The rotor shaft 510 has one end segment 510a that extends through the opening 514 and out of the housing 504 and is arranged for operable connection with a drive device, either directly or through suitable linkage structure, for example, as described above with respect to the connection of the rotary shaft 344 with the drive device arm 336, when the disposable housing portion 20 and the durable housing portion 22 are engaged. For example, the rotor shaft 510 may include a non-circular cross-sectional shape that mates with a correspondingly shaped aperture in an end of a rotatable shaft that is operatively connected to the drive device (similar to the non-circular, cross-section shaped mating elements of the shaft 344 and aperture 335 in FIGS. 18 and 19. In FIG. 20, The rotor shaft has a second end segment 510b that extends through the channel 512 in the base portion 504a and out of the housing 504. The rotor also includes a disk-shaped body 510c, located between the two end segments 510a and 510b. The end segments 510a and 510b and the disk-shaped body 510c of the rotor 510 may be formed as multiple separate elements connected together, or may be formed as a single, unitary structure in the configuration shown in FIG. 20.

The rotor body 510c is located within the interior volume of the cover portion 504a of the housing 504. The rotor body 510 includes at least two cam-follower channels 516 and 518, located in a spaced relation relative to each other and to the axis $A_5$ of the rotor 502, corresponding to the spaced relation of the first and second channels 506 and 508 in the base portion 504a of the housing 504. The corresponding spaced relation allows the two cam-follower channels 516 and 518 in the rotor body 510c of the rotor 510 to simultaneously align with the first and second channels 506 and 508 in the base portion 504a of the housing 504. In the embodiment of FIG. 20, the cam follower channels 516 and 518 are located at 180 degrees around the axis $A_5$, relative to each other. However, in other embodiments, the cam follower channels 516 and 518 may be located at other suitable spacing around the axis $A_5$, relative to each other. Also, while the embodiment in FIGS. 20-23 includes two cam follower channels and two associated cam followers, other embodiments may include no more than one cam follower channel and associated cam follower or more than two cam follower channels and associated cam followers.

A cam follower 520 is located in the cam follower channel 516 and a second cam follower 522 is located in the cam follower channel 518. The cam followers 520 and 522 are moveable within their respective cam follower channels 516 and 518, in the directions of arrows 524 and 525. In the illustrated embodiment, the cam follower channels 516 and 518 and the cam followers 520 and 522 are arranged such that the directions of movement 524 and 525 of the cam followers 520 and 522 are substantially parallel to the axis $A_5$ of the rotor 510. However, in other embodiments, the channels 516 and 518 and cam followers 520 and 522 may be arranged for movement in a direction transverse to the axis $A_5$ of the rotor 510.

The cam followers 520 and 522 may be made of any suitably rigid material, including, but not limited to, metal, plastic, ceramic, composite material or the like. The cam followers 520 and 522 have a shape that allows them to fit within the respective cam follower channels 516 and 518 and move in the directions of arrows 524 and 525, relative to the body 510c of the rotor 510. Each cam follower 520 and 522 includes a head portion 520a and 522a, respectively, on one end that is external to rotor body 510c. The head portions 520a and 522a have a size or shape that inhibits the head portions from passing through the respective cam follower channel 516 or 518. The cam followers 520 and 522 each have a length in the axial dimension $A_5$ sufficient to allow an end portion of each cam follower 520 and 522 opposite to the head portions 520a and 522a, to extend a distance out of the channels 516 and 518, when the respective cam follower 520 and 522 is moved to its full extent of motion in the direction of arrow 524.

A suitable bias member 526 may be associated with each cam follower 520 and 522 to urge the cam followers 520 and 522 in the direction of arrow 525, toward a cam surface 528 in the cover portion 504b of the housing 504. In the embodiment of FIG. 20, the bias members 526 each comprise a spring, such as, but not limited to a coil spring, bevel spring, or the like, located between the rotor body 510c and a respective head portion 520a or 522a of each cam follower 520 and 522. In other embodiments, the bias members 526 may comprise one or more magnets arranged to impart a magnetic force on a magnetic material of or within each cam follower 520 and 522.

In the embodiment of FIG. 20, the cam surface 528 comprises an interior-facing surface, having poritions 528a, 528b and 528c, discussed above, that surrounds the opening 514 in the cover portion 504b of the housing 504. The cam surface 528 extends around the circumference of the axis $A_5$ of the rotor 510 and has a first portion 528a aligned with the inlet channel 506 and a second portion 528b aligned with the outlet channel 508. The second portion 528b of the cam surface 528 is arranged closer to the rotor body 510c than the first portion 528a of the cam surface 528. For example, the second portion 528b of the cam surface 528 may be provided on a wide or thick wall segment of the cover portion 504b of the housing 504, relative to the wall width or thickness of the cover portion 504b at the first portion 528a of the cam surface 528. The cam surface 528 may be a smooth, continuous surface that extends from the first portion 528a to the second portion 528b and back to the first portion 528a, around the axis $A_5$.

A flexible membrane 530 is located adjacent the surface of the rotor body 510c that faces the base portion 504a of the housing 504. The flexible membrane 530 may comprise a disk-shaped sheet of flexible material, such as, but not limited to a silicone, rubber or other suitable material, secured to one surface (the surface facing the base portion 504a of the housing 504) of the rotor body 510c.

A sealing member 532 is secured to the flexible membrane 520 and rotor body 510c and is located between the flexible membrane 530 on the rotor body 510c and the base portion 504a of the housing 504. The sealing member 532 may be a disc-shaped plate of material that provides a suitable fluid seal and that allows rotational motion of the rotor body 510c, relative to the sealing member 530. The sealing member 532 may be made of polytetrafluoroethylene or other suitable material that provides a relatively low friction surface facing the base portion 504a of the housing 504. The sealing member 532 includes a first passage 532a arranged in alignment with one of the cam follower channels (channel 516 in FIG. 20). The sealing member 532 also includes a second passage 532b arranged in alignment with the other cam follower channel (channel 518 in FIG. 20). In embodiments in which the rotor body 510c includes more or less than two cam follower channels, the sealing member 532 includes a corresponding number of passages (e.g. passages 532a and 532b).

A clamp structure may be provided to provide a clamping force, for clamping the sealing member 532 between the flexible membrane 530 on rotor body 510c and the base portion 504a of the housing 504. In the embodiment of FIG. 20, the clamping structure comprises a plate 534 attached by a screw to the free end of the end segment 510b of the rotor shaft 510 (or otherwise secured to the end segment 510b of the rotor shaft 510) and a coil spring 536 arranged between the plate 534 and the base portion 504a of the housing 504. The coil spring 536 is provided with a suitable tension to urge the rotor in the direction of arrow 524, relative to the housing 504.

In operation, the rotor 502 is arranged such that the end segment 510a of the rotor shaft 510 is operatively engaged with a drive device located in a durable housing portion 22 (either directly, or through a suitable linkage structure), when the disposable housing portion 20 is engaged with the durable housing portion 22, as described above. When operatively engaged with the drive device, the rotor 502 (and the attached membrane 530 and sealing member 532) may be selectively rotated around the axis $A_5$ of the rotor 510, by selective activation of the drive device.

As the rotor 502 rotates, the cam followers 520 and 522 are moved along the cam surface 528. The bias members 526 urge the heads 520a and 522a of the respective cam followers 520 and 522 against the cam surface 528. When the rotor 502 is rotated to a position at which a cam follower is aligned with the inlet channel 506 (such as the cam follower 520 in FIGS. 20 and 21), the head of that cam follower (such as the head 520a of cam follower 520 in FIGS. 20 and 21) abuts against the first portion 528a of the cam surface 528. The first portion 528a of the cam surface 528 and the length of the cam followers 520 and 522 are selected to allow the end of the cam follower that faces the base portion 504a of the housing 504 to be separated from the base portion 504a by a distance sufficient to form an open volume 540 in the passage 532a of the sealing member 532, between the flexible membrane 530 and the base portion 504a of the housing 504, when the head of the cam follower abuts the first portion 528a of the cam surface 528.

Rotary motion of the rotor 502 causes the cam followers 520 and 522 to move along the cam surface 528 and, as a result, to move in the direction of arrow 525 as the cam follower moves from the second portion 528b, to the first portion 528a of the cam surface 528. As the cam follower (520 in FIGS. 20 and 21) is moved in the direction of arrow 525, a portion of the flexible membrane 530 that defines one side of the chamber 532a flexes away from the base portion 504a of the housing 504, to enlarge the volume of the chamber 532a. As the chamber 532a volume increases, the pressure within the chamber 532a decreases sufficient to draw a volume of fluid from a reservoir (not shown in FIGS. 20-22), through the inlet channel 506 and into the chamber 532a.

When the rotor 502 is rotated to a position at which a cam follower is aligned with the outlet channel 506 (such as the cam follower 522 in FIGS. 20 and 22), the head of that cam follower (such as the head 522a of cam follower 522 in FIGS. 20 and 22) abuts against the second portion 528b of the cam surface 528. The second portion 528b of the cam surface 528 and the length of the cam followers 520 and 522 are selected to allow the end of the cam follower that faces the base portion 504a of the housing 504 to be relatively close to the base portion 504a to flex a portion of the membrane toward the base portion 504a of the housing 504, to sufficiently close the volume in the passage 532b of the sealing member 532, when the head of the cam follower abuts the second portion 528b of the cam surface 528. As the chamber 532b volume decreases, the pressure within the chamber 532b increases to expel the volume of fluid from the chamber 532b through the outlet channel 508, to the injection site (not shown in FIGS. 20-23).

Accordingly, as the rotor 502 rotates, individual volumes of fluid are drawn in through the inlet channel 506 and into the volume of a chamber (such as chamber 532a in FIG. 20 and 21), moved with the rotation of the rotor 502 (and the membrane 530 and sealing member 532 attached to the rotor) to align with the outlet channel 508 and expelled through the outlet channel 508. The rotation of the rotor 502 may be controlled by controlling the drive device to selectively apply a rotational force to the rotor 502, when the durable housing portion 22 and the disposable housing portion 20 are engaged. In that manner, the drive device may be selectively driven to selectively draw volumes of fluid into the inlet channel 506 and expel volumes of fluid through the outlet channel 508.

In each of the above embodiments, the drive device and linkage structure may comprise any suitable drive motor or other drive device and linkage that converts electrical power to rotational motion to provide a rotary drive force for rotating a drive shaft and/or drive gear described above. Such drive devices may include, but are not limited to a DC motor, flat or pancake DC motor, servo motor, stepper motor, electronically commutated motor, rotary piezo-electrically actuated motor, and the like. In further embodiments, the drive device may comprise. a bender or linear actuator in combination with an escapement wheel arrangement, to rotatably drive the drive shaft and/or drive gear. For example, a drive device for rotatably driving the drive shafts or drive gears described above may comprise a piezo-electrically actuated bender and escapement wheel arrangement, a thermally actuated bender and escapement wheel arrangement, a shape memory alloy wire and escapement wheel arrangement, an electronically actuated solenoid and escapement wheel arrangement, or the like. Examples of shape memory alloy wire drive systems may be found in U.S. Pat. No. 6,375,638 issued Apr. 23, 2002, and entitled "Incremental Motion Pump Mechanisms Driven by Shape Memory Alloy Wire or the Like," and U.S. patent application Ser. No. 11/230,142 filed Sep. 19, 2005, and entitled "SMA Wire Driven Positive Displacement Micro-Pump With Pulsatile Output," both of which are incorporated herein by reference in their entirety.

Escapement wheel arrangements operable with bender or linear actuators in accordance with example embodiments of the present invention are described with reference to FIGS. 24a-24c. As shown in FIG. 24a, an escapement wheel 460 is supported for rotation around an axis $A_1$ (extending into the page), in the direction of arrow 462. The escapement wheel 460 has an outer peripheral edge provided with serrations or teeth 464. Each tooth 464 includes a sloped surface 466 arranged at an obtuse angle relative to an axial direction of the wheel 460 and a catch surface 465 in a substantially axial direction of the wheel. A drive pawl 468 is located adjacent the escapement wheel 460 and at least partially between two of the teeth on the escapement wheel. The drive pawl 468 is supported for movement in a generally linear direction, as represented by the double arrow 469, between a start position S and an end position E.

The drive pawl 468 has a drive surface 470 for engaging the catch surface 465 of an adjacent tooth 464 on the escapement wheel 460, when the drive pawl 468 is moved in a direction from the start position S to the end position E. The drive pawl 468 has a further surface 471 facing away from the drive surface 470 and configured for riding over the sloping surface 466 of a tooth 464 on the escapement wheel 460, when the drive pawl is moved in a return direction from the end position E to the start position S. The further surface 471 of the drive pawl 468 may be sloped at an angle relative to the radial direction of drive wheel, to assist the drive pawl 468 in riding over the sloping surface 466 of a tooth 464 of the escapement wheel.

As described in more detail below, the drive pawl 468 is coupled to a bender or linear motion actuator to selectively drive the drive pawl 468 from the start position S to the end position E. With each motion of the drive pawl 468 from the start position S to the end position E, the surface 470 engages the catch surface 465 of a tooth 464 on the escapement wheel and rotates the escapement wheel 460 a small distance. A bias member 472 is operably coupled to the drive pawl 468, to bias the drive pawl 468 in a return direction, to return the drive pawl 468 to the start position. The bias member 472 may comprise a spring as shown in FIG. 20a or other suitable mechanism for providing a bias force to return the drive pawl 468 to the start position, including, but not limited to a permanent magnet, electromagnet, electronic or thermal linear actuator, shaped memory alloy, or the like. In the illustrated embodiment, the bias member 472 comprises a coil spring having one end coupled to the drive pawl 468 and another end coupled to a fixed surface, for example, a fixed surface of a wall or other fixed structure of or within the durable portion of the delivery devices described above.

A further pawl 474 may be provided to inhibit back rotation of the escapement wheel 460 in the direction opposite to the direction of arrow 462. For example, the further pawl 474 may be located adjacent the escapement wheel 460 and at least partially between two of the teeth on the escapement wheel. The further pawl 474 has a surface 476 for engaging the catch surface 465 of an adjacent tooth 464 on the escapement wheel 460, to inhibit rotary motion of the escapement wheel 460 in the direction opposite to the direction of arrow 462.

The pawl 474 has a further surface 477 facing opposite to the surface 476, configured for riding over the sloping surface 466 of a tooth 464 on the escapement wheel 460, when the escapement wheel is driven in the rotary direction of arrow 462 by action of the drive pawl 468. The surface 477 of the pawl 474 may be angled relative to the radial direction of drive wheel, to assist the pawl 474 in riding over the sloping surface 466 of a tooth 464 of the escapement wheel. The pawl 474 may be supported for pivotal motion about a pivot point 478 in the direction of double arrow 479, to allow the surface 477 of the pawl 474 to pivot in a direction away from the escapement wheel, to further assist the pawl 474 in riding over the sloping surface 466 of a tooth 464 of the escapement wheel.

A bias member 480 may be arranged to bias the surface 476 of the pawl 474 toward the escapement wheel, to return the pawl 474 to a position in which the surface 476 engages the catch surface 465 of a tooth 464, after the pawl 474 has ridden over the sloping surface 466 of an adjacent tooth 464 of the escapement wheel. The bias member 480 may comprise a spring as shown in FIG. 24a or other suitable mechanism for providing a bias force to return the pawl 474 to the position in which the pawl surface 476 engages the catch surface 465 of a tooth 464, including, but not limited to a permanent magnet, electromagnet, electronic or thermal linear actuator, shaped memory alloy, or the like. In the illustrated embodiment, the bias member 480 comprises a coil spring having one end coupled to the pawl 474 and another end coupled to a fixed surface, for example, a fixed surface of a wall or other fixed structure of or within the durable portion of the delivery devices described above. In other embodiments, a spring may be located around or within the pivot point 478 of the pawl 474 for effecting the bias force described above.

As described above, the drive pawl 468 is coupled to a bender or linear motion actuator to selectively drive the drive pawl 468 and cause the escapement wheel to rotate a small distance with each motion of the drive pawl 468 from the start position S to the end position E. A bender or linear actuator may comprise a piezoelectric bender or piezoelectric actuator, a thermally actuated bender, a shape memory alloy wire, an electronically actuated solenoid, or the like. Such actuators for providing small, generally linear movements in response to the application of an electrical power signal are known. Examples of shape memory alloy wire drive systems may be found in U.S. Pat. No. 6,375,638 issued Apr. 23, 2002, and entitled "Incremental Motion Pump Mechanisms Driven by Shape Memory Alloy Wire or the Like," and U.S. patent application Ser. No. 11/230,142 filed Sep. 19, 2005, and entitled "SMA Wire Driven Positive Displacement Micro-Pump With Pulsatile Output," both of which are incorporated herein by reference in their entirety.

As shown in FIG. 24b, a bender actuator 482 may be configured to include a connector end 484 that is provided with a lateral motion represented by arrow 486 relative to a major axis $A_2$ of the actuator body, when a power signal is applied to the actuator. Alternatively, as shown in FIG. 24c, a linear actuator 488 may be configured to include a connector end 492 that is provided with a longitudinal motion represented by arrow 494 relative to a major axis $A_3$ of the actuator body, when a power signal is applied to the actuator. A bender actuator as shown in FIG. 24b, for providing lateral motion, may be coupled to the drive pawl 468 at a connection location 496. The connection location 496 for a bender actuator may be on a surface of the drive pawl 468 that is substantially perpendicular to the drive surface 470. Alternatively, a linear actuator as shown in FIG. 24*c*, for providing longitudinal motion, may be coupled to the drive pawl 468 at a connection location 498. The connection location 498 for a linear actuator may be on a surface of the drive pawl 468 that is substantially parallel to the drive surface 470. In that manner, a bender or a linear actuator as shown in FIGS. 24*b* and 24*c* may be employed to selectively move the drive pawl 468 from the start position S to the end position E and, thus drive the escapement wheel 460 in a rotary manner.

The escapement wheel 460 may be configured to rotate the rotary distance of one tooth for each movement of the drive pawl 468 from the start position S to the end position E. In further embodiments, the drive pawl 468 may be configured to cause the escapement wheel 460 to rotate a rotary distance of a pre-defined number of teeth greater than one tooth, for each movement of the drive pawl 468 from the start position S to the end position E. The escapement wheel 460 may be coupled to one of the drive shafts or drive gears described above, to rotate the drive shaft or drive gear with rotation of the escapement wheel 460. In one embodiment, the drive shaft may be connected in axial alignment directly to the escapement wheel 460, such that the rotary axis $A_1$ of escapement wheel is in alignment with the longitudinal axis of the drive shaft. In other embodiments, the escapement wheel 460 may be coupled, in axial alignment, with any one of the drive gears described above, to transfer rotary motion of the escapement wheel 460 to the drive gear. In yet further embodiments, other suitable gear and linkage arrangements may be employed for transferring rotary motion of the escapement wheel 460 to the drive shaft or drive gear.

The use of bender or linear actuators with escapement wheel arrangements as described above may provide certain advantages over electric motor and linkage arrangements, in that the bender or linear actuators can provide a repeatable, controlled, step-like response to an electrical power signal. In the context of driving a delivery device for delivering a medication to a patient-user, the ability to accurately control the drive response can provide significant advantages, for example, in administering accurate quantities, small quantities at accurate levels and accurate recording of delivered quantities of the medication. In addition, bender or linear actuators with escapement wheel arrangements can be made relatively small and flat and can, therefore, improve the ability to form the delivery device with a relatively small and flat shape. In addition, bender or linear actuators with escapement wheel arrangements can operate with relatively low power requirements, thus prolonging the operational life of the power source and allowing smaller power sources to be employed, thus, allowing further reductions in the size of the delivery device.

Other types of drive devices may be coupled to an escapement wheel 460, through a single tooth wheel 499, as shown in FIG. 24*d*, to provide a controlled, step-like response. For example, in the embodiment shown in FIG. 24*d*, the escapement wheel 460 may be coupled to the drive shafts or drive gears described above, while the single tooth wheel 499 may be coupled to be driven by any suitable rotary drive source, including, but not limited to a DC motor, flat or pancake DC motor, servo motor, stepper motor, electronically commutated motor, rotary piezo-electrically actuated motor, and the like. While the wheel 499 in FIG. 24*d* is provided with a single tooth to effect a rotation of the escapement wheel 460 a rotary distance of a single tooth for each complete rotation of the wheel 499, other embodiments may employ a wheel 499 having two teeth (or another pre-defined number of teeth) for effecting a rotation of the escapement wheel 460 a rotary distance of two teeth (or the pre-defined number of teeth) for each complete rotation of the wheel 499.

Figure 3:
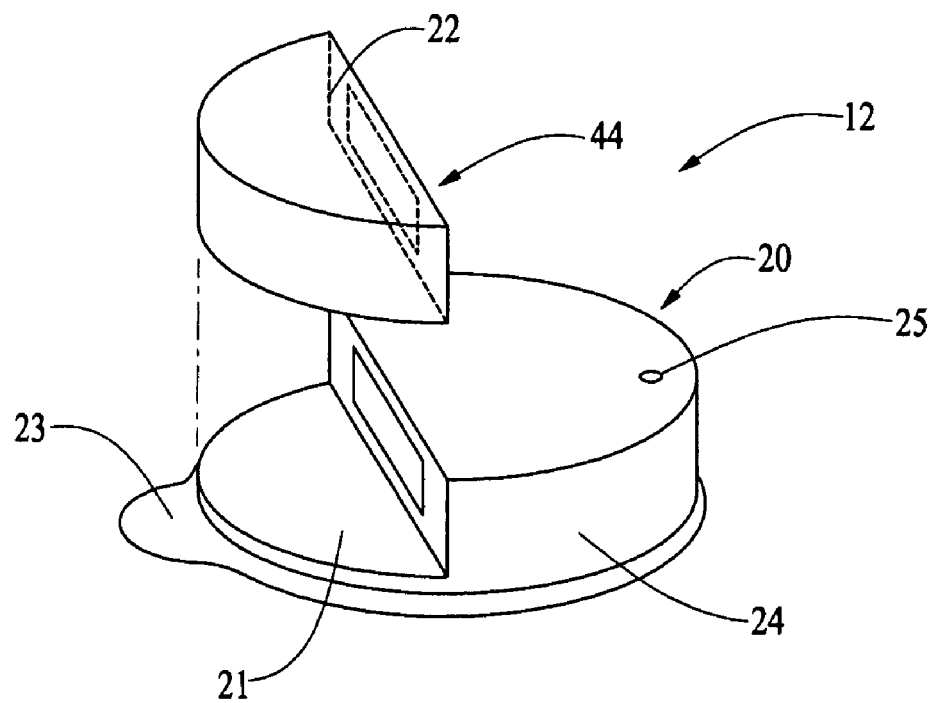
FIG. 3 is a perspective view of a durable portion and a disposable portion of the delivery device of FIG. 2, with the durable portion separated from the disposable portion.
Figure 25:
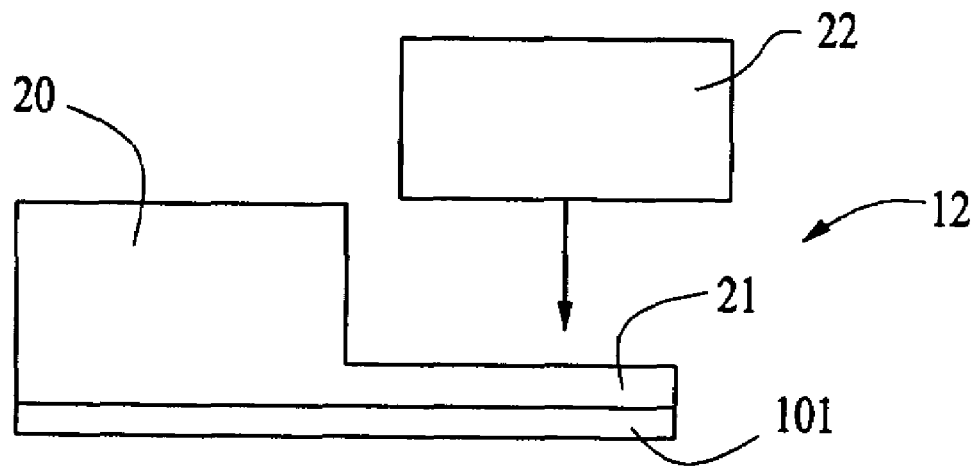
FIG. 25 shows a schematic side view of an arrangement of a durable housing portion and a disposable housing portion of a delivery system according to an embodiment of the invention consistent with the embodiment of FIG. 3.

In embodiments described above, the disposable housing portion (e.g., 20 in FIG. 3) is provided with a base portion 21 that may be secured to the patient-user's skin by, for example, but not limited to, an adhesive material provided on the bottom surface of the base portion 21. That arrangement is generally represented, in side view, in FIG. 25, wherein an adhesive material 101 is provided on the bottom surface (skin-facing surface) of the base 21 of the disposable housing portion 20. As shown in FIGS. 2, 3 and 25, the durable housing portion 22 may be configure to be arranged on the base 21 of the disposable housing portion 20 to engage and connect to the disposable housing portion 22. In such an arrangement, the base 21 may be disposed between the durable housing portion 22 and the patient-user's skin, during operation, such that only the base 21 of the disposable housing portion remains in contact with the patient-user's skin, during operation.

Figure 26:
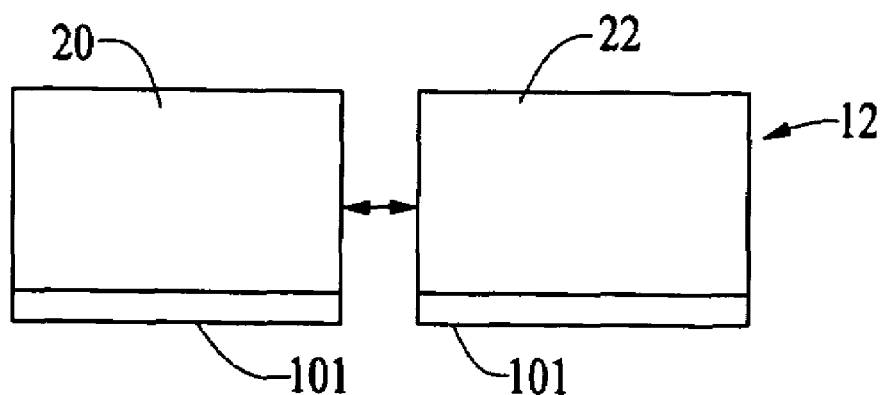
FIG. 26 shows a schematic side view of an arrangement of a durable housing portion and a disposable housing portion of a delivery system according to another embodiment of the invention.

However, in other embodiments, the durable housing portion 22 and the disposable housing portion 20 may be configured to engage each other in a side-by-side arrangement, for example, as represented in FIG. 26. In the side-by-side arrangement in FIG. 26, either one or both of the durable housing portion 22 and the disposable housing portion 20 may be provided with a base having an adhesive material 101 (and a peelable cover layer 23 as shown in FIG. 3).

Figure 27:
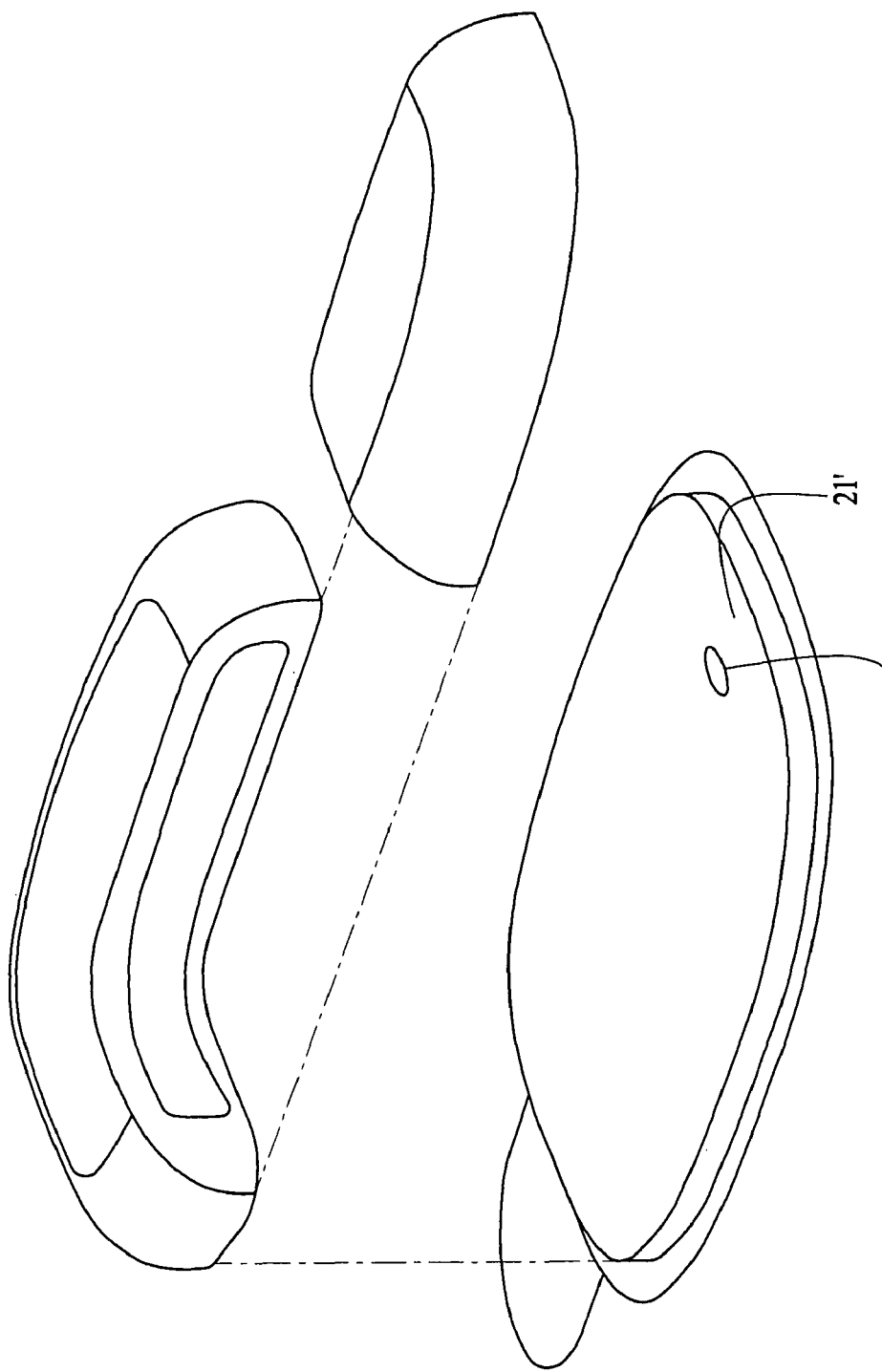
FIG. 27 shows a partially exploded view of a delivery device according to an embodiment of the invention.

In yet further embodiments, as represented by FIG. 27, one or both of the durable housing portion 22 nd the disposable housing portion 20 may be attachable and detachable from a separate base member 21'. Suitable connecting structure, such as described above for connecting the durable housing portion and the disposable housing portion together, may be employed for connecting the durable housing portion and the disposable housing portion to the base member 21'. The separate base member 21' may include a generally flat, plate-like structure made of any suitably rigid material including, but not limited to, plastic, metal, ceramic, composite material or the like. The base member 21' has a surface (the upper-facing surface in FIG. 25) to which the disposable housing portion 20 and the durable housing portion 22 may be attached. The base member 21' has a second surface (the lower-facing surface in FIG. 27) to which an adhesive material and a peelable cover film may be applied, as described above, to allow the base member 21' to be secured to a patient-user's skin.

The base member 21' may include a needle inserter device 25, as described above. Examples of suitable needle inserter devices are described in U.S. patent application Ser. No. 11/211,095, filed Aug. 23, 2005, and U.S. Patent Application No. 60/839,840, titled "Infusion Medium Delivery System, Device And Method With Needle Inserter And Needle Inserter Device Method", filed Aug. 23, 2006, each of which is incorporated herein by reference in its entirety. In such embodiments, the base member 21' may be secured to a patient-user's skin. Then, the needle inserter 25 may be activated to insert a hollow needle or cannula into the patient-user's skin. Then, after the hollow needle or cannula is inserted, the durable housing portion 22 and the disposable housing portion 20 may be attached to the base member 21', to connect the reservoir within the disposable housing portion 20 in fluid flow communication with the hollow needle or cannula. In one embodiment, the durable housing portion 22 and the disposable housing portion 20 may be connected together (for example, in the manner described above) before attaching those housing portions to the base member 21'. In a further embodiment, one of the durable and disposable housing portion is attached to the base member 21' before the durable and disposable housing portions are connected together. In such further embodiment, the needle inserter device may be activated to insert a hollow needle or cannula into the patient-user's skin after the disposable housing portion is attached to the base member 21' (either before or after the durable and disposable housing portions are connected together). Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Alternatively, reference number 25 may represent an opening in the base member 21' that aligns with a needle inserter device (or aligns with a further opening) located in the disposable housing portion 20, when the disposable housing portion 20 is attached to the base member 21'. In such embodiments, the base member 21' may be secured to the patient-user's skin. Then the disposable housing portion 20 is attached to the base member 21' (either before or after the durable and disposable housing portions are connected together). Once the disposable housing portion 20 is attached to the base member 21', the needle inserter device 25 may be activated to insert a hollow needle or cannula into a patient-user's skin (either before or after the durable and disposable housing portions are connected together).

Figure 28:
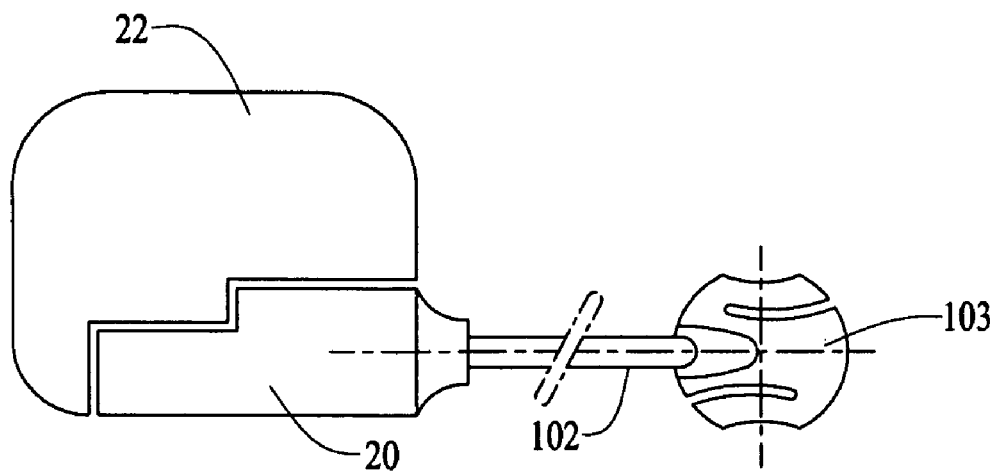
FIG. 28 shows a schematic top view of an arrangement of a durable housing portion and a disposable housing portion of a delivery system according to an embodiment of the invention.

Also, while embodiments described above may include an on-board needle or cannula injector device that may be activated through the operator or opening 25, other embodiments may employ an injection site module 103 that is external to the disposable housing portion 20, but connected to the disposable housing portion 20, through a suitable conduit 102, as shown in FIG. 28. The external injection site module 103 may include a needle or cannula injector device structure and an operator or opening (similar to the operator or opening 25 described above) through which the injector device may be activated. Alternatively or in addition, the external injection site module 103 may include an infusion set such as, but not limited to an infusion set as described or referenced in U.S. patent application Ser. No. 10/705,686, filed Nov. 10, 2003, titled "Subcutaneous Infusion Set" (Publication No. 2005/0101910) and/or U.S. patent application Ser. No. 11/004,594, filed Dec. 3, 2004, titled "Multi-Position Infusion Set Device And Process" (Publication No. 2006/0129090), each of which is assigned to the assignee of the present invention and each of which is incorporated herein by reference, in its entirety.

The conduit 102 that connects the module 103 with the disposable housing portion 20 may be any suitable tubing structure having a fluid flow passage, such as, but not limited to, a flexible tube made of plastic, silicone or the like. An adhesive material may be provided on the tubing structure (or between the tubing structure and the patient-user's skin) to secure the tubing to the patient-user's skin. By locating the injection site module 103 external to the disposable housing portion 20, the disposable housing portion 20 and the durable housing portion 22 may be clipped to a patient-user's clothing, belt, suspender or other article of apparel or may be held in a pocket of an article of apparel or carried in a purse or the like.

In one embodiment, the conduit 102 may be fixed at one end to the disposable housing portion 20, in fluid-flow communication with the reservoir within the disposable housing portion 20, and fixed at a second end to an external injection site module 103, for connection in fluid-flow communication with a hollow needle or cannula, as described above. In further embodiments, one or both of the ends of the conduit 102 may include suitable connection structures that allow the conduit ends to be selectively connected in fluid-flow communication with, and selectively disconnected from the disposable housing portion 20 and/or the injection site module 103. Such connectors may comprise a hollow needle and septum, a Luer connector, or other suitable fluid-communication connectors. In such embodiments, the disposable housing portion 20 and the durable housing portion 22 may be disconnected from the module 103, for example, by disconnecting one of the ends of the conduit 102 from the module 103 or the disposable housing portion 20, while leaving the module 103 in place (without requiring the patient-user to withdraw the needle or cannula and, later, insert a needle or cannula to resume operation). In this manner, a patient-user may readily disconnect and remove the disposable housing portion 20 and durable housing portion 22, for example, to allow the patient-user to shower, bath, swim or conduct other activities, yet also allow the patient-user to readily re-connect the disposable housing portion 20 to the module 103, for example, upon completion of such activities. Examples of connectors can be found in U.S. patent application Ser. No. 10/328,393 filed Dec. 22, 2003, and entitled "Reservoir Connector," and U.S. Pat. No. 5,545,152 issued Aug. 13, 1996, and entitled "Quick-Connect Coupling For A Medication Infusion System," both of which are incorporated herein by reference in their entirety. In other alternatives, different connectors such as Luer locks, or the like may be used.

Figure 29:
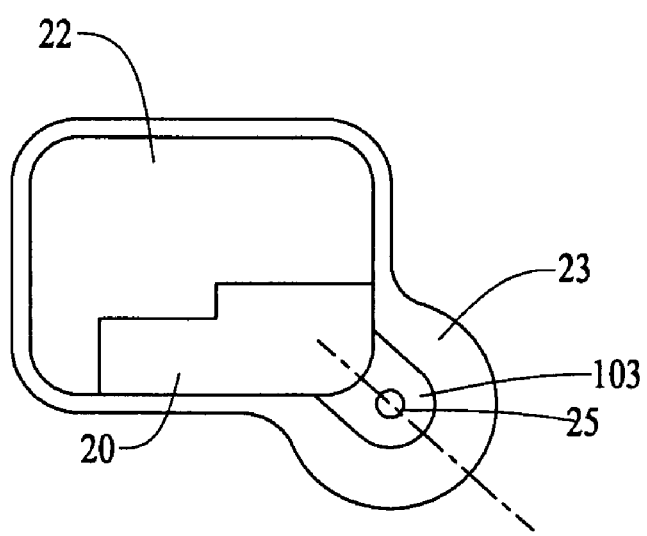
FIG. 29 shows a schematic top view of an arrangement of a durable housing portion and a disposable housing portion of a delivery system according to another embodiment of the invention.

In yet further embodiments, the conduit 102 may be eliminated and an injection site module 103 may be directly connected with the disposable housing portion 20, as shown in FIG. 29. In such an embodiment, one or more suitable fluid flow passages are provided through the disposable housing portion 20 and into the injection site module 103, for fluid-flow communication between the reservoir in the disposable housing portion 20 and a hollow needle or cannula, as described above. Also, in such embodiments, the injection site module 103 and the disposable housing portion 20 may include mating connection structures to allow the injection site module 103 and the disposable housing portion 20 to be selectively connected and disconnected from each other.

Figure 30:
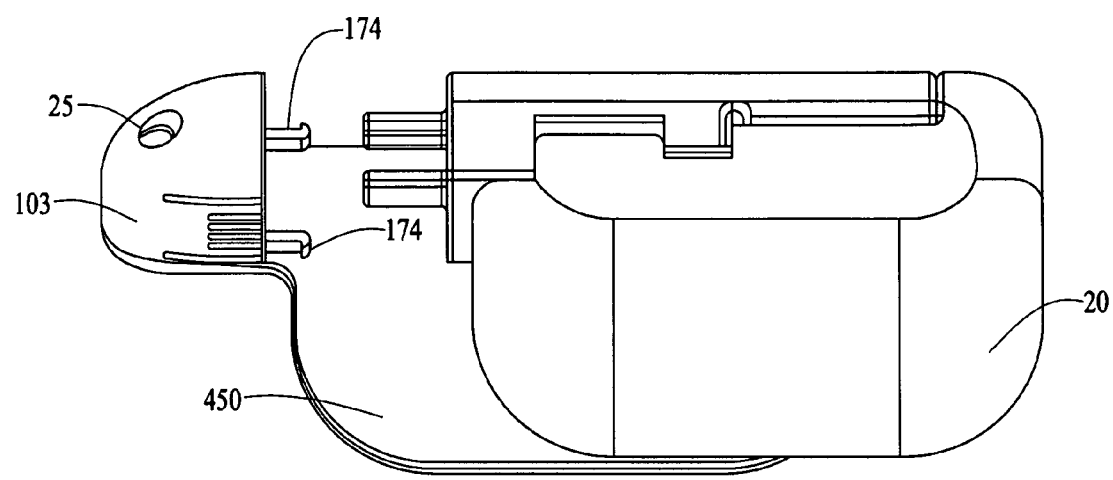
FIGS. 30-32 each show a perspective view of a connection arrangement for a disposable housing portion and an injection site module.
Figure 31:
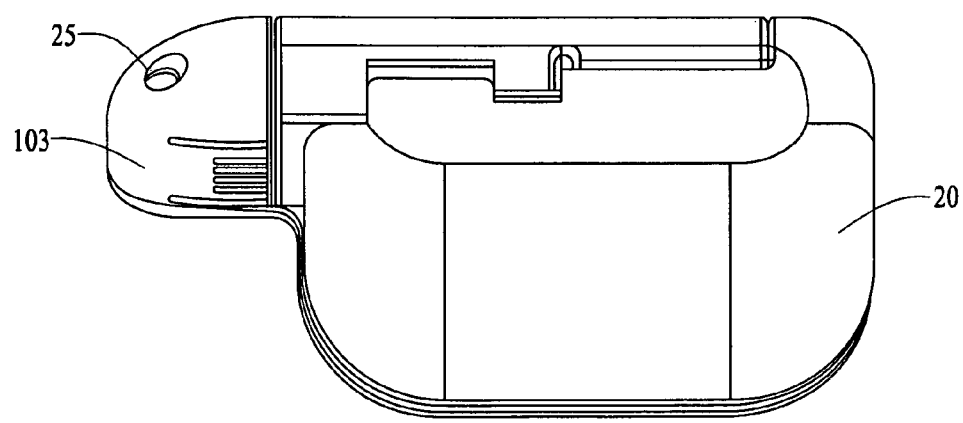
Figure 32:
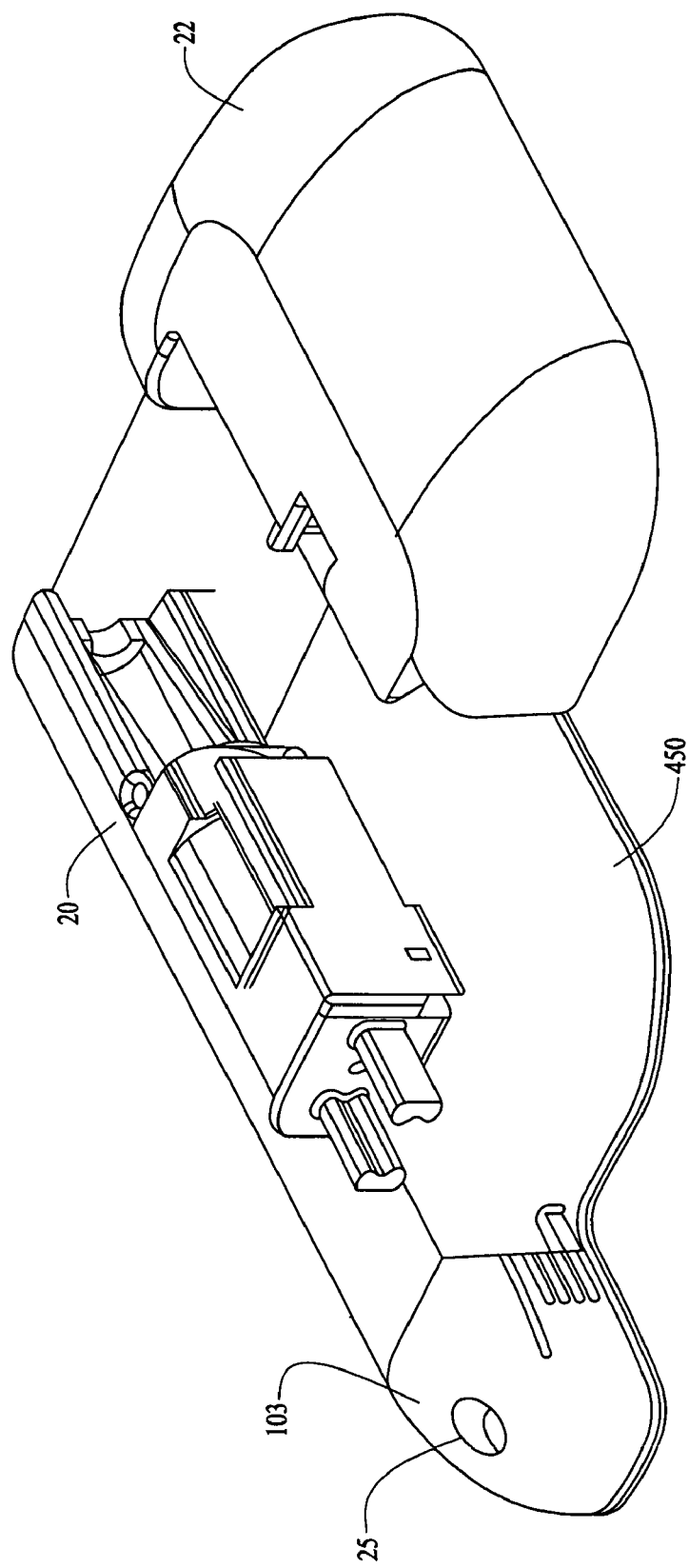

Various examples of mating arrangements, for directly connecting an injection site module 103 to a disposable housing portion are described with reference to FIGS. 30-37. FIGS. 30-32 show an example arrangement, in which an injection site module 103 includes at least one (two in FIG. 26) protruding engagement pawl 174 that are configured to be received in a corresponding number of receptacles on the disposable housing portion 20 (similar to the pawls 74 and receptacles 76 described in U.S. Patent Application No. 60/839,741, titled "Infusion Pumps And Methods And Delivery Devices And Methods With Same", filed Aug. 23, 2006, which has been incorporated herein by reference. In other embodiments, the pawl(s) 174 may be located on the disposable housing portion 20, while the corresponding receptacles may be located on the module 103. In yet other embodiments, each of the disposable housing portion 20 and the module 103 may include one or more pawls and one or more receptacles.

The pawls 174 and receptacles may be configured to allow a patient-user to manually slide the pawls into the receptacles as the disposable housing portion 20 and the module 103 are brought together. When the pawls 174 are received in the corresponding receptacles, the module 103 is secured to the disposable housing portion 20. The pawls 174 may include a shaped portion or head to provide a snap-fit with the receptacles, when the pawls 174 are fully received within the receptacles. The pawls 174 may be configured with sufficient flexibility to allow the patient-user to separate the disposable housing portion 20 from the module 103, by applying a sufficient force to pull those two parts away from each other and unsnap the pawls 174 from the receptacles. In the embodiment of FIGS. 30-32, the module 103 may be attached to or may include a base portion 450 that may be secured to a patient-user's skin during operation, in lieu of the extended base 21 of the disposable housing portion 20 described above. The base portion 450 may include an adhesive material as described herein with respect to the base 21 of the disposable housing portion 20.

As shown in FIG. 32, the embodiment of FIGS. 30-32 may be formed in three general parts, including the disposable housing portion 20, the durable housing portion 22 and the module 103 on the base portion 450. The durable housing portion 22 and the disposable housing portion 20 may be secured together (as shown in FIG. 28), and the combined, connected disposable and durable housing portions may be secured to the module 103 and base portion 450. In one embodiment, the base portion 450 may be secured to a patient-user's skin, before the combined, connected disposable and durable housing portions are secured to the module 103 and base portion 450. In a further embodiment, the combined, connected disposable and durable housing portions are secured to the module 103 and base portion 450, before the base portion 450 is secured to the patient-user's skin.

Figure 33:
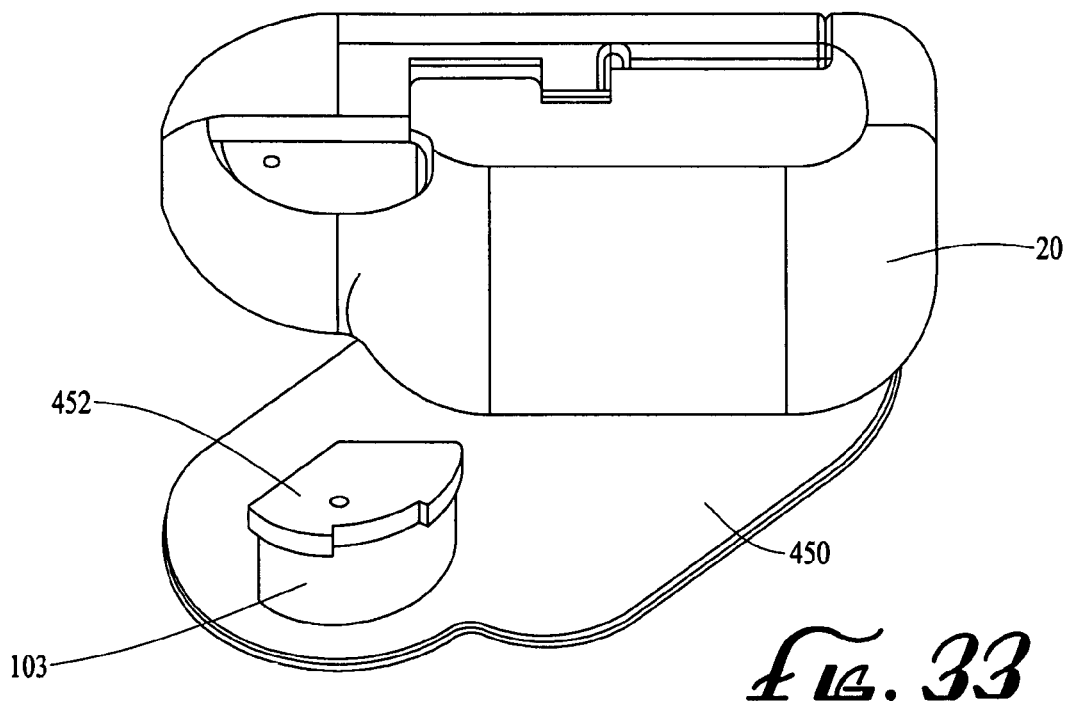
FIGS. 33 and 34 each show a perspective view of another connection arrangement for a disposable housing portion and an injection site module.
Figure 34:
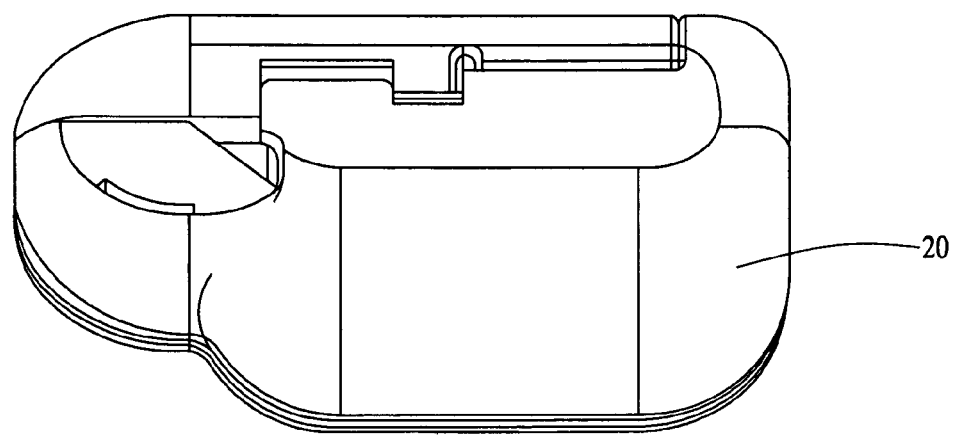

Another example of a connection structure is described with reference to FIGS. 33 and 34, wherein the module 103 includes a shaped head 452 configured to be received within a correspondingly shaped opening or receptacle in the disposable housing portion 20. The shaped head 452 may be configured with a shape that allows the head to be received in the receptacle when the disposable housing portion 20 is aligned relative to the module 103 in a first alignment position, as shown in FIG. 29, and further allows the disposable housing portion 20 to be rotated relative to the module 103 while the head 452 is received within the receptacle to a second alignment position as shown in FIG. 34. The receptacle in the disposable housing portion 20 may be shaped to allow the head 452 to be freely received or removed from the receptacle, when the disposable housing portion 20 is in the first alignment position (FIG. 33), yet abut the head 452 and inhibit separation of the head 452 from the receptacle (and, thus, inhibit separation of the disposable housing portion 20 from the module 103), when the disposable housing portion is in the second alignment position (FIG. 34).

Figure 35:
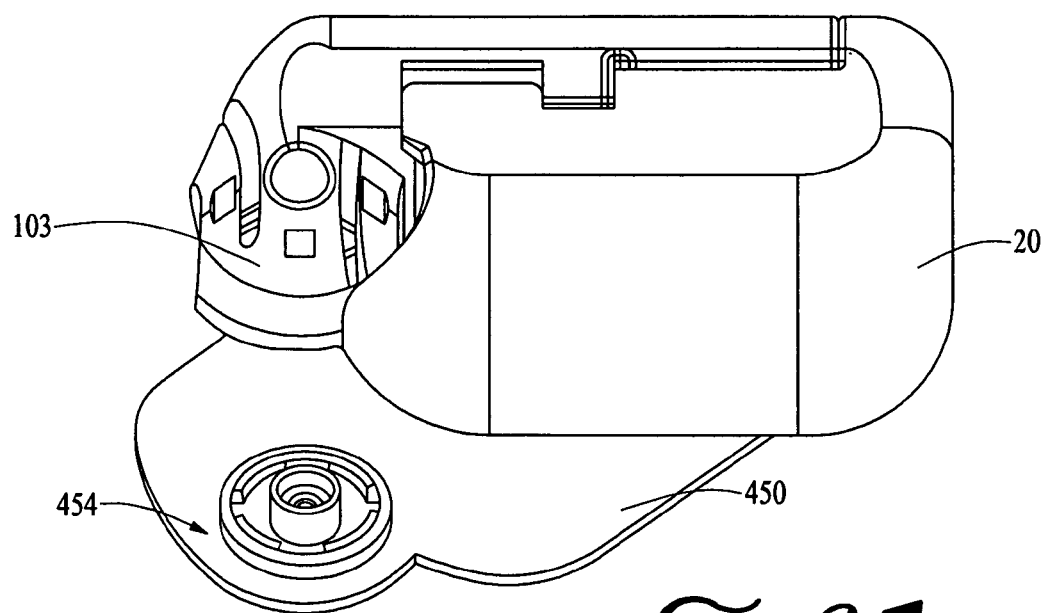
FIGS. 35-37 each show a perspective view of yet another connection arrangement for a disposable housing portion and an injection site module.
Figure 36:
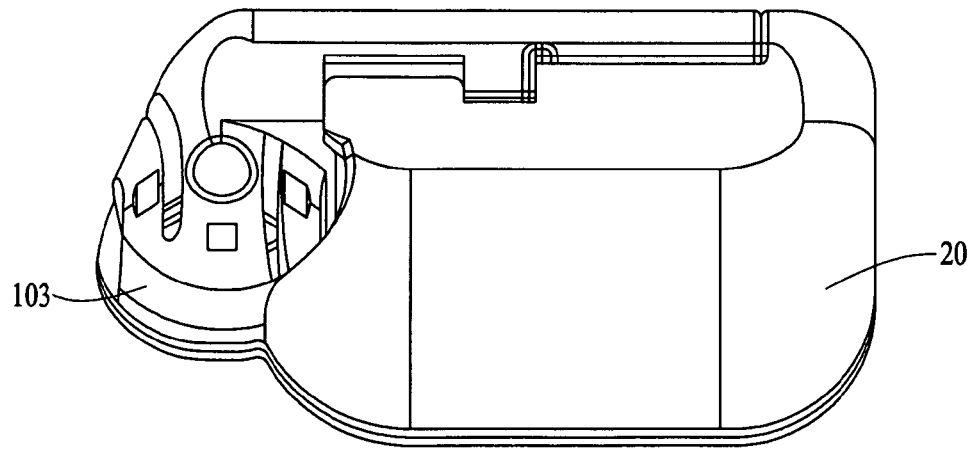
Figure 37:
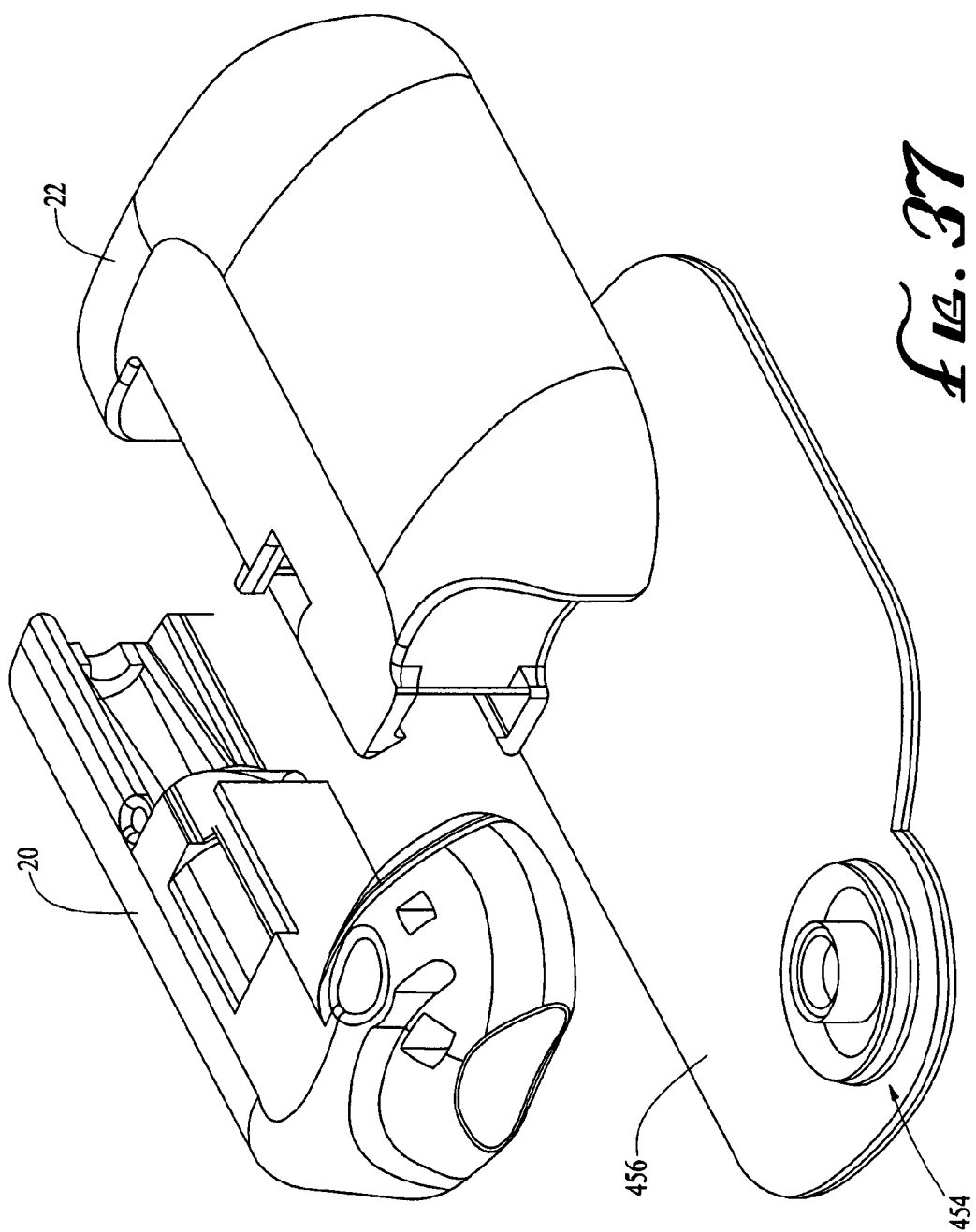

A further example of a connection structure is described with reference to FIGS. 35-37, wherein the module 103 includes a shaped receptacle 454 configured to receive a correspondingly shaped connector member in the disposable housing portion 20. In FIGS. 35-37, the module 103 is formed, integral with the disposable housing portion 20. The shaped receptacle 454 may be configured with a shape that allows the connector member of the disposable housing portion to be engaged with the receptacle 454 when the disposable housing portion 20 is aligned relative to the module 103 in a first alignment position, as shown in FIG. 35, and further allows the disposable housing portion 20 to be rotated relative to the module 103, while the receptacle 454 is engaged within the connector member, to a second alignment position as shown in FIG. 36. The receptacle 454 and the connector member in the disposable housing portion 20 may be shaped to allow the connector member to be freely engage the receptacle 454, when the disposable housing portion 20 is in the first alignment position (FIG. 35), yet lock with the receptacle 454 and inhibit separation of the connector member from the receptacle (and, thus, inhibit separation of the disposable housing portion 20 from the module 103), when the disposable housing portion is in the second alignment position (FIG. 36). The receptacle 454 and connection member may include any suitable known rotary connection structures for connecting two structures together upon engagement and relative rotation of the two structures in one direction, yet allow the two structures to be disengaged and separated from an engaged arrangement, by relative rotation of the two structures in the second, opposite direction.

As shown in FIG. 37, the embodiment of FIGS. 35-37 may be formed in three general parts, including the disposable housing portion 20, the durable housing portion 22 and the module 103 on the base portion 456. The durable housing portion 22 and the disposable housing portion 20 may be secured together (as shown in FIG. 35), and the combined, connected disposable and durable housing portions may be secured to the base portion 456. In one embodiment, the base portion 456 may be secured to a patient-user's skin, before the combined, connected disposable and durable housing portions are secured to the base portion 456. In a further embodiment, the combined, connected disposable and durable housing portions are secured to the base portion 456, before the base portion 456 is secured to the patient-user's skin.

In yet further embodiments, the injection site module may be formed as a unitary structure with the disposable housing portion 20. Also, in any of the embodiments described above, one or more sensors may be located in the disposable housing portion 20, the injection site module 103 or the durable housing portion 22, for sensing a biological condition, including, but not limited to, blood glucose level, level of infusion medium in the patient-user's blood and/or other conditions. Such sensor(s) may include a hollow needle or cannula and/or a set of micro-needles, as described above, for piercing the patient-user's skin to convey fluid from the patient to the sensor.

Various aspects of the multiple embodiments described above may be employed independently or in combinations thereof. Significant advantages can be obtained from various embodiments and combinations described herein, wherein an at-site delivery system may be made of two parts, including a disposable portion and a non-disposable portion. The disposable portion may contain all materials that are in direct contact with the infusion medium, such as reservoir body, reservoir piston, septum systems and injection needle. The non-disposable portion could contain substantially the materials that are not in contact with the medication including the drive system, pressure or force sensing system, battery, electronics, display, and non-disposable housing. The pump could be designed such that the disposable portion (user filled or pre-filled cartridge) is inserted into the non-disposable portion. By simplifying the manner in which the disposable portion of the delivery device can be replaced and by simplifying the manner in which the delivery device can be re-activated after replacing a disposable portion, a greater number of patient-users will be able to use and benefit from such delivery devices.

While particular embodiments of the present invention have been shown and described, it will be obvious to those skilled in the art that the invention is not limited to the particular embodiments shown and described and that changes and modifications may be made without departing from the spirit and scope of the claimed invention. For example, while embodiments described above may include an adhesive material and a cover film 23 (FIGS. 2 and 3), further embodiments may include a plurality of adhesive material layers alternating with a corresponding plurality of cover film layers 23, to allow the delivery device to be secured, removed and re-secured to the patient-user's skin one or more times.

In such embodiments, a first cover film layer located at the end of the stack of alternating layers of adhesive material and cover film, may be removed to expose a first layer of adhesive material. With the first layer of adhesive material exposed, the delivery device (or component thereof) may be adhered to a patient-user's skin, as described above. After a suitable period of usage, the delivery device (or component having the adhesive) may be removed from the patient-user's skin, for example, for servicing, re-filling, replacement of one or more components, or the like. After removal of the delivery device (or component) from the patient-user's skin, a second cover film layer on the delivery device (or component) may be removed to expose a second layer of adhesive material. With the second layer of adhesive material exposed, the delivery device (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while embodiments described above include an injection site located on the disposable housing portion 20 or in an external injection site module 103, other embodiments may employ an injection site located in the durable housing portion 22 and connected, through suitable fluid-flow passages, to the reservoir in the disposable housing portion 20, when the durable housing portion and disposable housing portion are engaged. Also, while embodiments are described above in the context of delivery devices for delivering an infusion medium from a reservoir to a patient-user, other embodiments may be operated to withdraw a fluidic medium from a patient-user (or other source) and transfer the fluidic medium to the reservoir. Such other embodiments may be operated by operating the drive device to selectively move the piston plunger away from the septum-end of the reservoir (to increase the fluid-retaining volume of the reservoir) to create a negative pressure sufficient to draw fluid from the patient-user (or other source) to which the hollow needle or cannula is secured.

What is claimed is:

1. A delivery device comprising:
    a first housing portion;
    a second housing portion configured to selectively engage with and disengage from the first housing portion, the first housing portion provided with a conduit support surface that faces the second housing portion when the second housing portion is engaged with the first housing portion, the conduit support surface having a recessed groove;
    a rotatable rotor carrying and supporting at least one pad or roller for movement in an annular path with the rotation of the rotor, the rotatable rotor and the at least one pad or roller being supported for rotation about an axis of rotation by the second housing portion when the first and second housing portions are engaged and when the first and second housing portions are disengaged;
    a conduit supported by the first housing portion when the first and second housing portions are engaged and when the first and second housing portions are disengaged, the conduit having a flexible portion arranged within the recessed groove and within at least a portion of the annular path of the at least one pad or roller to be engaged at locations along the annular path by the at least one roller or pad and to receive a force from the at least one roller or pad in a direction parallel to the axis of rotation of the rotor when the second housing portion and the first housing portion are engaged, the flexible portion of the conduit being resiliently collapsible at the locations of engagement of the at least one roller or pad to provide a pumping action as the rotor rotates the at least one roller or pad along the annular path while the second housing portion and first housing portion are engaged, the conduit being connectable in fluid flow communication with an injection site;
    a reservoir having an interior volume for containing a fluid, the interior volume of the reservoir being in fluid flow communication with the conduit; and
    a drive device supported by the second housing portion and operatively coupled to the rotor for selectively rotating the rotor;
    wherein the conduit support surface, reservoir and rotatable rotor are aligned along an axis parallel to the axis of rotation of the rotor when the second housing portion is engaged with the first housing portion, and wherein the recessed groove in the conduit support surface and the flexible portion of the conduit are located between the reservoir and the rotatable rotor when the second housing portion is engaged with the first housing portion; and
    wherein the at least one pad or roller is connected to the rotatable rotor and engages the flexible portion of the conduit when the second housing portion is engaged with the first housing portion and disengages from the flexible portion of the conduit when the second housing portion is disengaged from the first housing portion.

2. A delivery device according to claim 1, wherein:
    the second housing portion has a housing structure with an internal volume;
    the rotor is disposed outside of the internal volume; and
    the delivery device further comprising a rotor shaft having a longitudinal axis, the rotor shaft coupled to the rotor and extending into the internal volume of the second housing portion and operatively coupled to the drive device.

3. A delivery device according to claim 2, wherein the rotor shaft extends through an aperture in a wall of the second housing portion.

4. A delivery device according to claim 3, further comprising a seal disposed around the aperture in the wall of the second housing portion, the seal providing at least one of an air tight, moisture tight or hermetically sealed environment within the second housing portion.

5. A delivery device according to claim 1, wherein the rotor comprises a rotary wheel and wherein the at least one pad or roller is supported by the rotary wheel.

6. A delivery device according to claim 1, wherein the rotor comprises a rotary wheel supported for rotation about a first axis of rotation and wherein the at least one pad or roller comprises at least one rotatable roller supported for rotation on the rotary wheel about a second axis of rotation that is orthogonal to the first axis of rotation.

7. A delivery device according to claim 1, wherein the flexible portion of the conduit is supported on a flat support surface.

8. A delivery device according to claim 1, wherein the flexible portion of the conduit that is arranged within at least a portion of the annular path of the at least one pad or roller comprises a portion of the conduit arranged in at least a partial coil around a generally annular path.

9. A delivery device according to claim 8, wherein the rotor is rotatable about a first axis of rotation and wherein the at least one pad or roller comprises a plurality of rollers, each supported for rotation on the rotor about a respective axis of rotation that is transverse to the first axis of rotation and along a path that aligns with the annular path of the conduit, when the first and second housing portions are engaged.

10. A delivery device according to claim 1, wherein the rotor is rotatable about a first axis of rotation and wherein the at least one pad or roller comprises at least one roller supported for rotation on the rotor about an axis of rotation that is transverse to the first axis of rotation.

11. A delivery device according to claim 1, wherein the rotor is rotatable about a first axis of rotation and wherein the at least one pad or roller comprises a plurality of rollers, each roller supported for rotation on the rotor about an axis of rotation that is transverse to the first axis of rotation.

12. A delivery device according to claim 1, wherein the second housing portion is configured to selectively engage with the first housing portion when the first and second housing portions are moved from mutually separated locations into contact with each other along a linear path of motion that is parallel to the axis of rotation of the rotor.

13. A delivery device according to claim 12, wherein the at least one roller or pad is arranged to move toward and contact the flexible portion of the conduit along a linear path of motion that is parallel to the axis of rotation of rotor, when the first and second housing portions are moved from mutually separated locations into contact with each other.

14. A delivery device according to claim 12, wherein when the first and second housing portions are moved from mutually separated locations into contact with each other, the force received by the flexible portion of the conduit from the at least one roller or pad is in a direction parallel to the linear path of motion.

15. A delivery device according to claim 1, wherein when the second housing portion and the first housing portion are engaged, the force received by the flexible portion of the conduit from the at least one roller or pad is in a direction parallel to the linear path of motion.

16. A delivery device according to claim 1, wherein the rotatable rotor carries and supports the at least one pad or roller for movement in an annular path when the second housing portion and the first housing portion are engaged and when the second housing portion and the first housing portion are disengaged.

17. A delivery device according to claim 1, wherein the conduit support surface is perpendicular to the axis of rotation of the rotatable rotor when the second housing portion and the first housing portion are engaged.

18. A delivery device according to claim 1, further comprising:
  a power source carried by the first housing portion when the first and second housing portions are engaged and when the first and second housing portions are disengaged;
  a first electrical connector carried by the first housing portion when the first and second housing portions are engaged and when the first and second housing portions are disengaged, the first electrical connector being in electrical communication with the power source;
  a second electrical connector carried by the second housing portion when the first and second housing portions are engaged and when the first and second housing portions are disengaged, the second electrical connector being in electrical communication with the drive device;
  the first and second electrical connectors being arranged to be in electrical communication with each other when the first and second housing portions are engaged and to be out of electrical communication with each other when the first and second housing portions are disengaged;
  wherein, the first and second electrical connectors are electrically coupled to electrically couple the power source to the drive device when the first and second housing portions are engaged, and the first and second electrical connectors are electrically de-coupled to electrically decouple the power source and the drive device when the first and second housing portions are disengaged.

19. A delivery device according to claim 1, further comprising a rotor shaft mechanically coupled to the drive device to be selectively rotated by the drive device, wherein the second housing portion has an enclosed interior in which the drive device is located, the second housing portion has an outer wall provided with an opening through which the rotor shaft extends from the interior of the second housing portion to a location external to the second housing portion, and the second housing portion includes a seal that provides an hermetic seal in opening through which the rotor shaft extends, wherein the enclosed interior of the second housing portion is hermetically sealed.

20. A method of making a delivery device, the method comprising:
  providing a first housing portion;
  providing a second housing portion configured to selectively engage with and disengage from the first housing portion;
  providing the first housing portion with a conduit support surface that faces the second housing portion when the second housing portion is engaged with the first housing portion, the conduit support surface having a recessed groove;
  supporting a rotatable rotor for rotation on the second housing portion about an axis of rotation, the rotor carrying and supporting at least one pad or roller for movement in an annular path with the rotation of the rotor when the first and second housing portions are engaged and when the first and second housing portions are disengaged;
  providing a conduit having a flexible portion;
  coupling an interior volume of a reservoir in fluid flow communication with the conduit, the interior volume of the reservoir for containing a fluid;
  supporting the flexible portion of the conduit on the first housing portion when the first and second housing portions are engaged and when the first and second housing portions are disengaged, and arranging the flexible portion of the conduit within the recessed groove and within at least a portion of the annular path of the at least one pad or roller to be engaged at locations along the annular path by the at least one pad or roller and to receive a force from the at least one pad or roller in a direction parallel to the axis of rotation of the rotor when the second housing portion and the first housing portion are engaged, the flexible portion of the conduit being resiliently collapsible at the locations of engagement of the at least one pad or roller to provide a pumping action as the rotor rotates while the first and second housing portions are engaged, the conduit being connectable in fluid flow communication with an injection site;
  supporting a drive device on the second housing portion; and
  operatively coupling the drive device to the rotor for selectively rotating the rotor to provide the pumping action while the first and second housing portions are engaged;
  wherein providing the first housing portion with a conduit support surface and supporting the flexible portion of the conduit comprises, aligning the conduit support surface, reservoir and rotatable rotor along an axis parallel to the axis of rotation of the rotor when the second housing portion is engaged with the first housing portion, and providing the recessed groove of the conduit support surface and the flexible portion of the conduit at a location that is between the reservoir and the rotatable rotor when the second housing portion is engaged with the first housing portion; and wherein supporting a rotatable rotor comprises connecting the at least one pad or roller to the rotatable rotor in a position to engage the flexible portion of the conduit when the second housing portion is engaged with the first housing portion and to disengage from the flexible portion of the conduit when the second housing portion is disengaged from the first housing portion.

21. A method according to claim 20, wherein:
providing a second housing portion comprises providing a housing structure with an internal volume;
supporting a rotatable rotor comprises supporting a rotor on the second housing portion, outside of the internal volume; and
operatively coupling the drive device to the rotor comprises extending a rotor shaft having a longitudinal axis into the interior volume of the second housing portion, operatively coupling the rotor shaft to the rotor and to the drive device to transfer drive force from the drive device to the rotor.

22. A method according to claim 21, wherein extending a rotor shaft comprises extending the rotor shaft through an aperture in a wall of the second housing portion.

23. A method according to claim 22, further comprising arranging a seal around the aperture in the wall of the second housing portion.

24. A method according to claim 20, wherein supporting a rotatable rotor comprises supporting a rotary wheel and wherein the at least one pad or roller is supported by the rotary wheel.

25. A method according to claim 20, wherein supporting a rotatable rotor comprises supporting a rotary wheel for rotation about a first axis of rotation and wherein the at least one pad or roller comprises at least one rotatable roller supported for rotation on the rotary wheel about a second axis of rotation that is orthogonal to the first axis of rotation.

26. A method according to claim 25, wherein supporting the flexible portion of the conduit comprises supporting the flexible portion of the conduit on a flat support surface.

27. A method according to claim 20, wherein supporting the flexible portion of the conduit comprises supporting the flexible portion of the conduit on a flat support surface.

28. A method according to claim 20, wherein arranging the flexible portion of the conduit that is arranged within at least a portion of the annular path of the at least one pad or roller comprises arranging a portion of the conduit in at least a partial coil around a generally annular path.

29. A method according to claim 28, wherein supporting a rotatable rotor comprises supporting a rotor for rotation about a first axis, wherein the at least one pad or roller comprises a plurality of rollers, each supported for rotation on the rotor about a respective axis of rotation that is transverse to the first axis of rotation and along a path that aligns with the annular path of the conduit, when the first and second housing portions are engaged.

30. A method according to claim 20, wherein supporting a rotatable rotor comprises supporting a rotor for rotation about a first axis and wherein the at least one pad or roller comprises at least one roller supported for rotation on the rotor about an axis of rotation that is transverse to the first axis of rotation.

31. A method according to claim 20, wherein supporting a rotatable rotor comprises supporting a rotor for rotation about a first axis of rotation and wherein the at least one pad or roller comprises a plurality of rollers, each roller supported for rotation on the rotor about an axis of rotation that is transverse to the first axis of rotation.

32. A method according to claim 20, wherein the conduit support surface is perpendicular to the axis of rotation of the rotatable rotor when the second housing portion and the first housing portion are engaged.

33. A method according to claim 20, further comprising:
supporting a power source on the first housing portion when the first and second housing portions are engaged and when the first and second housing portions are disengaged;
supporting a first electrical connector on the first housing portion when the first and second housing portions are engaged and when the first and second housing portions are disengaged, and coupling the first electrical connector in electrical communication with the power source;
supporting a second electrical connector on the second housing portion when the first and second housing portions are engaged and when the first and second housing portions are disengaged, and coupling the second electrical connector in electrical communication with the drive device;
arranging the first and second electrical connectors at locations to be in electrical communication with each other when the first and second housing portions are engaged and to be out of electrical communication with each other when the first and second housing portions are disengaged;
wherein, the first and second electrical connectors are electrically coupled to electrically couple the power source to the drive device when the first and second housing portions are engaged, and the first and second electrical connectors are electrically de-coupled to electrically decouple the power source and the drive device when the first and second housing portions are disengaged.

34. A delivery device comprising:
a first housing portion having a conduit support surface;
a second housing portion configured to selectively engage with and disengage from the first housing portion;
a rotatable rotor carrying at least one pad or roller for movement in a path with rotation of the rotor, the rotatable rotor and the at least one pad or roller being supported for rotation about an axis of rotation by the second housing portion when the first and second housing portions are engaged and when the first and second housing portions are disengaged;
a conduit supported by the first housing portion when the first and second housing portions are engaged and when the first and second housing portions are disengaged, the conduit having a flexible portion arranged within the path of the at least one pad or roller to be engaged at locations along the path by the at least one roller or pad and to receive a force from the at least one roller or pad when the second housing portion and the first housing portion are engaged, the flexible portion of the conduit being resiliently collapsible at the locations of engagement of the at least one roller or pad to allow fluid to flow through the conduit as the rotor rotates the at least one roller or pad along the annular path while the second housing portion and first housing portion are engaged; and a reservoir having an interior volume for containing a fluid, the interior volume of the reservoir being in fluid flow communication with the conduit;

wherein the conduit support surface, reservoir and rotatable rotor are aligned along an axis parallel to the axis of rotation of the rotor when the second housing portion is engaged with the first housing portion, and wherein the conduit support surface and the flexible portion of the conduit are located between the reservoir and the rotatable rotor when the second housing portion is engaged with the first housing portion; and wherein the at least one pad or roller is connected to the rotatable rotor and engages the flexible portion of the conduit when the second housing portion is engaged with the first housing portion and disengages from the flexible portion of the conduit when the second housing portion is disengaged from the first housing portion.

* * * * *